US010366793B2

(12) United States Patent
Apte et al.

(10) Patent No.: US 10,366,793 B2
(45) Date of Patent: *Jul. 30, 2019

(54) METHOD AND SYSTEM FOR CHARACTERIZING MICROORGANISM-RELATED CONDITIONS

(71) Applicant: uBiome, Inc., San Francisco, CA (US)

(72) Inventors: Zachary Apte, San Francisco, CA (US); Jessica Richman, San Francisco, CA (US); Daniel Almonacid, San Francisco, CA (US); Catalina Valdivia, San Francisco, CA (US); Rodrigo Ortiz, San Francisco, CA (US); Inti Pedroso, San Francisco, CA (US); Victoria Dumas, San Francisco, CA (US); Paz Tapia, San Francisco, CA (US); Eduardo Morales, San Francisco, CA (US)

(73) Assignee: uBiome, Inc., San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/845,190

(22) Filed: Dec. 18, 2017

(65) Prior Publication Data

US 2018/0122511 A1     May 3, 2018

Related U.S. Application Data

(63) Continuation-in-part of application No. 15/606,743, filed on May 26, 2017, which is a continuation of application No. 14/919,614, filed on Oct. 21, 2015, now Pat. No. 9,703,929.

(60) Provisional application No. 62/066,369, filed on Oct. 21, 2014, provisional application No. 62/087,551, filed on Dec. 4, 2014, provisional application No. 62/092,999, filed on Dec. 17, 2014, provisional application No. 62/147,376, filed on Apr. 14, 2015, provisional application No. 62/147,212, filed on Apr. 14, 2015, provisional application No. 62/147,362, filed on Apr. 14, 2015, provisional application No. 62/146,855, filed on Apr. 13, 2015, provisional application No. 62/206,654, filed on Aug. 18, 2015, provisional application No. 62/435,167, filed on Dec. 16, 2016, provisional application No. 62/435,170, filed on Dec. 16, 2016, provisional application No. 62/435,178, filed on Dec. 16, 2016, provisional application No. 62/435,184, filed on Dec. 16, 2016, provisional application No. 62/435,246, filed on Dec. 16, 2016, provisional application No. 62/435,263, filed on Dec. 16, 2016, provisional application No. 62/435,299, filed on Dec. 16, 2016, provisional application No. 62/435,316, filed on Dec. 16, 2016, provisional application No. 62/435,332, filed on Dec. 16, 2016, provisional application No. 62/522,293, filed on Jun. 20, 2017, provisional application No. 62/555,782, filed on Sep. 8, 2017, provisional application No. 62/558,489, filed on Sep. 14, 2017, (Continued)

(51) Int. Cl.
| | |
|---|---|
| G01N 33/48 | (2006.01) |
| G16H 50/20 | (2018.01) |
| G16H 10/40 | (2018.01) |
| G16B 50/00 | (2019.01) |
| G16B 20/00 | (2019.01) |
| G06G 7/58 | (2006.01) |
| G16B 40/00 | (2019.01) |

(52) U.S. Cl.
CPC ............. *G16H 50/20* (2018.01); *G16B 20/00* (2019.02); *G16B 50/00* (2019.02); *G16H 10/40* (2018.01); *G16B 40/00* (2019.02)

(58) Field of Classification Search
None
See application file for complete search history.

(56) References Cited

U.S. PATENT DOCUMENTS

| | | | |
|---|---|---|---|
| 6,033,864 | A | 3/2000 | Braun et al. |
| 6,309,643 | B1 | 10/2001 | Braun et al. |

(Continued)

FOREIGN PATENT DOCUMENTS

| | | |
|---|---|---|
| CN | 105407728 | 3/2015 |
| EP | 2631240 | 8/2013 |

(Continued)

OTHER PUBLICATIONS

"K03100: IepB: signal peptidase I," KEGG, Aug. 7, 2012 (Aug. 7, 2012), p. 1 of 1. Retrieved from the Internet: on Jun. 12, 2016 (Jun. 12, 2016).

(Continued)

*Primary Examiner* — Eric S Dejong
(74) *Attorney, Agent, or Firm* — Kilpatrick Townsend & Stockton LLP

(57) ABSTRACT

Embodiments of a method and/or system for characterizing a microorganism-related condition (e.g., human behavior condition, disease-related condition, etc.) for a user can include one or more of: generating a microbiome dataset for each of an aggregate set of biological samples associated with a population of subjects, based on sample processing of the biological samples; processing a supplementary dataset associated with one or more microorganism-related conditions for the set of users; and performing a microorganism-related characterization (e.g., human behavior characterization, disease-related characterization, etc.) process for the one or more microorganism-related conditions, based on the supplementary dataset and/or microbiome features extracted from the microbiome dataset.

22 Claims, 12 Drawing Sheets

Related U.S. Application Data provisional application No. 62/582,191, filed on Nov. 6, 2017, provisional application No. 62/582,162, filed on Nov. 6, 2017, provisional application No. 62/582,172, filed on Nov. 6, 2017.

(56) References Cited

U.S. PATENT DOCUMENTS

| | | | |
|---|---|---|---|
| 6,632,641 | B1 | 10/2003 | Brennan et al. |
| 6,861,053 | B1 | 3/2005 | Lin et al. |
| D521,843 | S | 5/2006 | Hung |
| 7,048,906 | B2 | 5/2006 | Lin et al. |
| 7,176,002 | B2 | 2/2007 | Lao et al. |
| 8,478,544 | B2 | 7/2013 | Colwell et al. |
| 8,598,203 | B2 | 12/2013 | Tarcic et al. |
| 8,883,264 | B2 | 11/2014 | Yang et al. |
| 9,028,841 | B2 | 5/2015 | Henn et al. |
| 9,149,473 | B2 | 10/2015 | Ecker et al. |
| 9,433,651 | B2 | 9/2016 | Jones et al. |
| 9,447,195 | B2 | 9/2016 | Cordova et al. |
| 9,506,109 | B2 | 11/2016 | Savelkoul et al. |
| 9,663,831 | B2 | 5/2017 | Apte et al. |
| 9,710,606 | B2 | 7/2017 | Apte et al. |
| 10,242,160 | B2 | 3/2019 | Apte et al. |
| 2002/0012926 | A1 | 1/2002 | Quake et al. |
| 2003/0190314 | A1 | 10/2003 | Campbell et al. |
| 2005/0196785 | A1 | 9/2005 | Quake et al. |
| 2006/0073501 | A1 | 4/2006 | Van Den Boom et al. |
| 2006/0089310 | A1 | 4/2006 | Goldstein et al. |
| 2007/0134652 | A1 | 6/2007 | Slepnev et al. |
| 2007/0259337 | A1 | 11/2007 | Hully et al. |
| 2008/0131556 | A1 | 6/2008 | De Simone et al. |
| 2010/0035232 | A1 | 2/2010 | Ecker et al. |
| 2010/0129816 | A1 | 5/2010 | Savelkoul et al. |
| 2010/0172874 | A1 | 7/2010 | Turnbaugh et al. |
| 2011/0027219 | A1 | 2/2011 | Tarcic et al. |
| 2011/0177976 | A1 | 7/2011 | Gordon et al. |
| 2012/0045771 | A1 | 2/2012 | Beier et al. |
| 2012/0129794 | A1 | 5/2012 | Dowd et al. |
| 2012/0149584 | A1 | 6/2012 | Olle et al. |
| 2012/0252775 | A1 | 10/2012 | Finegold et al. |
| 2013/0017999 | A1 | 1/2013 | Fremont et al. |
| 2013/0045874 | A1 | 2/2013 | Ehrlich |
| 2013/0108598 | A1 | 5/2013 | Oresic et al. |
| 2013/0121968 | A1 | 5/2013 | Quay |
| 2013/0184302 | A1 | 7/2013 | Bortey et al. |
| 2014/0093478 | A1 | 4/2014 | Turnbaugh et al. |
| 2014/0136120 | A1 | 5/2014 | Colwell et al. |
| 2014/0179726 | A1 | 6/2014 | Bajaj et al. |
| 2014/0199281 | A1 | 7/2014 | Henn et al. |
| 2014/0315929 | A1 | 10/2014 | Chiosis |
| 2014/0341853 | A1 | 11/2014 | Hovanky |
| 2014/0363399 | A1 | 12/2014 | Jones et al. |
| 2015/0050245 | A1 | 2/2015 | Herman et al. |
| 2015/0211055 | A1 | 7/2015 | Apte et al. |
| 2015/0211078 | A1 | 7/2015 | Apte et al. |
| 2015/0213193 | A1 | 7/2015 | Apte et al. |
| 2015/0259728 | A1 | 9/2015 | Cutliffe et al. |
| 2015/0374761 | A1 | 12/2015 | Sadowsky et al. |
| 2016/0032363 | A1 | 2/2016 | Stintzi et al. |
| 2016/0040216 | A1 | 2/2016 | Akins et al. |
| 2016/0110515 | A1 | 4/2016 | Apte et al. |
| 2016/0138089 | A1 | 5/2016 | Harris et al. |
| 2016/0228003 | A1 | 8/2016 | Apte et al. |
| 2016/0232313 | A1 | 8/2016 | Apte et al. |
| 2016/0263166 | A1 | 9/2016 | Elinav et al. |
| 2017/0039347 | A1 | 2/2017 | Apte et al. |
| 2017/0262608 | A1 | 9/2017 | Apte et al. |
| 2017/0268045 | A1 | 9/2017 | Apte et al. |
| 2017/0268046 | A1 | 9/2017 | Apte et al. |
| 2017/0270268 | A1 | 9/2017 | Apte et al. |
| 2017/0270269 | A1 | 9/2017 | Apte et al. |
| 2017/0270270 | A1 | 9/2017 | Apte et al. |
| 2017/0270271 | A1 | 9/2017 | Apte et al. |
| 2017/0270272 | A1 | 9/2017 | Apte et al. |
| 2017/0286619 | A1 | 10/2017 | Apte et al. |
| 2017/0286620 | A1 | 10/2017 | Apte et al. |
| 2017/0327864 | A1 | 11/2017 | Apte et al. |
| 2017/0344719 | A1 | 11/2017 | Apte et al. |
| 2018/0070827 | A1 | 3/2018 | Apte et al. |
| 2018/0102187 | A1 | 4/2018 | Apte et al. |
| 2019/0085396 | A1 | 3/2019 | Apte et al. |

FOREIGN PATENT DOCUMENTS

| | | |
|---|---|---|
| EP | 2994756 | 3/2016 |
| WO | 050513 | 4/2012 |
| WO | 121298 | 8/2014 |
| WO | 138999 | 9/2014 |
| WO | 144092 | 9/2014 |
| WO | 145958 | 9/2014 |
| WO | 013214 | 1/2015 |
| WO | 2015/095241 A2 | 6/2015 |
| WO | 085326 | 6/2015 |
| WO | 095241 | 6/2015 |
| WO | 103165 | 7/2015 |
| WO | 112352 | 7/2015 |
| WO | 170979 | 11/2015 |
| WO | 2016/065075 A1 | 4/2016 |
| WO | 2015/112352 A8 | 6/2016 |
| WO | 138337 | 9/2016 |
| WO | 172643 | 10/2016 |
| WO | 2016/172643 A3 | 2/2017 |
| WO | 2017/044885 A1 | 3/2017 |
| WO | 044902 | 3/2017 |

OTHER PUBLICATIONS

"KEGG: Aminoacyl-tRNA biosynthesis—Reference pathway," Jul. 20, 2013 (Jul. 20, 2013). Retrieved from the internet: <http://web:archive.org/web/20130720015616/http:www.genome.jp/kegg-bin/show_pathway?map=map00970&show_description=show. on Jun. 20, 2016, (Jun. 20, 2016).

Avila, Maria et al., The Oral Microbiota: Living with a Permanent Guest, DNA and Cell Biology, Nov. 8, 2009, vol. 28, No. 8.

Carroll et al. "Alterations in composition and diversity of the intestinal microbiota in patients with diarrhea-predominant irritable bowel syndrome," Feb. 20, 2012 (Feb. 29, 2012), vol. 24, pp. 1-19 [Original pp. 5215-5230] entire document.

Cho et al. "The Human Microbiome: at the Interface of Health and Disease," Nature Reviews Genetics, Apr. 1, 2012 (Apr. 1, 2012), vol. 13, pp. 260-270.

Dewhirst, Floyd et al., The Human Oral Microbiome, Journal of Bacteriology, Oct. 2010, vol. 192, No. 19, pp. 5002-5017.

Evans, Morgan, Prosthetic valve endocarditis due to *Neisseria elongata* subsp. elongata in a patient with Klinefelter's syndrome, Journal of Medical Microbiology, Jun. 1, 2007, vol. 56, No. 6, pp. 860-862.

Greenblum et al. "Metagenomic Systems Biology of the Human Gut Microbiome Reveals Topological Shifts Associated with Obesity and Inflammatory Bowel Disease," Proceeding of the National Academy of Sciences, Dec. 19, 2011 (Dec. 19, 2011), vol. 109, pp. 594-599.

Kanehisa et al. "KEGG: Kyoto encyclopedia of genes and genomes,"Nucleic Acids Research, Jan. 1, 2000 (Jan. 1, 2000), vol. 28, No. 1, pp. 27-30.

Mak et al. "MetaboLyzer: A Novel Statistical Workflow for Analyzing Post Processed LC/MS Metabolomics Data," Anal Chem, Jan. 7, 2014 (Jan. 7, 2014), vol. 86, pp. 506-513.

Morgan et al. "Dysfunction of the intestinal microbiome in inflammatory bowel disease and treatment," Genome Biol. Apr. 16, 2012 (Apr. 16, 2012), vol. 13(9):R79, pp. 1-18. entire document.

Mutlu et al. "A Compositional Look at the Human Gastrointestinal Microbiome and Immune Activation Parameters in HIV Infected Subjects," PLoS Pathogens, Feb. 20, 2014 (Feb. 20, 2014), vol. 10, pp. 1-18.

Nakayama et al. "Aberrant Structures of Fecal Bacterial Community in Allergic Infants Profiled by 16S rRNA Gene Pyrosequenc-

(56) References Cited

OTHER PUBLICATIONS ing," FEMS Immunology & Medical Microbiology, Dec. 1, 2011 (Dec. 1, 2011), vol. 63, pp. 397-406.
Ponnusamy et al. "Microbial community and metabolomic comparison of irritable bowel syndrome faeces," Feb. 17, 2011 (Feb. 17, 2011), vol. 60, pp. 817-827. entire document.
Benedict, et al., "Gut Microbiota and Glucometabolic Alterations in Response to Recurrent Partial Sleep Deprivation in Normal-Weight Young Individuals", Molecular Metabolism, vol. 5, 2016, pp. 1175-1186.
Canadian Application No. 2,962,466, Examination Report dated Mar. 23, 2018, 4 pages.
European Application No. 15852829.9, Extended European Search Report dated May 14, 2018, 8 pages.
International Application No. PCT/US2015/056767, International Preliminary Report on Patentability dated May 4, 2017, 9 pages.
International Application No. PCT/US2015/056767, International Search Report and Written Opinion dated Jan. 11, 2016, 10 pages.
International Application No. PCT/US2017/067003, International Search Report and Written Opinion dated Apr. 26, 2018, 17 pages.
International Application No. PCT/US2018/035912, International Search Report and Written Opinion dated Sep. 12, 2018, 17 pages.
Kinross, et al., "Gut Microbiome-host Interactions in Health and Disease", Genome Medicine, vol. 3, No. 14, 2011, pp. 1-12.
Morgan, et al., "Biodiversity and Functional Genomics in the Human Microbiome", Trends Genet., vol. 29, No. 1, Jan. 2013, pp. 51-58.
Nagy-Szakal, et al., "Fecal Metagenomic Profiles in Subgroups of Patients with Myalgic Encephalomyelitis/Chronic Fatigue Syndrome", Microbiome, vol. 5, No. 44, 2017, pp. 1-17.
U.S. Appl. No. 14/919,614, Non-Final Office Action dated Jul. 14, 2016, 10 pages.
U.S. Appl. No. 14/919,614, Notice of Allowance dated May 19, 2017, 10 pages.
U.S. Appl. No. 15/606,743, Non-Final Office Action dated Dec. 19, 2017, 10 pages.
U.S. Appl. No. 15/606,743, Notice of Allowance dated Sep. 20, 2018, 5 pages.
U.S. Appl. No. 15/606,824, Final Office Action dated Sep. 20, 2018, 8 pages.
U.S. Appl. No. 15/606,824, Non-Final Office Action dated Jan. 16, 2018, 10 pages.
U.S. Appl. No. 15/606,874, Final Office Action dated Aug. 31, 2018, 8 pages.
U.S. Appl. No. 15/606,874, Non-Final Office Action dated Feb. 9, 2018, 10 pages.
U.S. Appl. No. 15/606,874, Notice of Allowance dated Jan. 17, 2019, 5 pages.
U.S. Appl. No. 15/606,909, Final Office Action dated Sep. 20, 2018, 8 pages.
U.S. Appl. No. 15/606,909, Non-Final Office Action dated Mar. 9, 2018, 10 pages.
U.S. Appl. No. 15/606,909, Notice of Allowance dated Feb. 20, 2019, 5 pages.
U.S. Appl. No. 15/606,943, Final Office Action dated Nov. 1, 2018, 7 pages.
U.S. Appl. No. 15/606,943, Non-Final Office Action dated Apr. 10, 2018, 10 pages.
U.S. Appl. No. 15/606,943, Notice of Allowance dated Mar. 8, 2019, 5 pages.
U.S. Appl. No. 15/606,975, Final Office Action dated Jun. 14, 2018, 8 pages.
U.S. Appl. No. 15/606,975, Non-Final Office Action dated Sep. 25, 2017, 10 pages.
U.S. Appl. No. 15/606,975, Notice of Allowance dated Oct. 19, 2018, 5 pages.
U.S. Appl. No. 15/621,144, Final Office Action dated Nov. 1, 2018, 7 pages.
U.S. Appl. No. 15/621,144, Non-Final Office Action dated Apr. 10, 2018, 10 pages.
U.S. Appl. No. 15/621,144, Notice of Allowance dated Mar. 8, 2019, 6 pages.
U.S. Appl. No. 15/621,152, Final Office Action dated Nov. 1, 2018, 7 pages.
U.S. Appl. No. 15/621,152, Non-Final Office Action dated Apr. 10, 2018, 10 pages.
U.S. Appl. No. 15/621,152, Notice of Allowance dated Mar. 8, 2019, 6 pages.
U.S. Appl. No. 15/997,654, Non-Final Office Action dated Nov. 1, 2018, 13 pages.
U.S. Appl. No. 15/606,824, "Notice of Allowance", dated Mar. 26, 2019, 5 pages.
U.S. Appl. No. 15/606,975, "Notice of Allowance", dated Apr. 3, 2019, 5 pages.
U.S. Appl. No. 15/997,654, "Notice of Allowance", dated Apr. 4, 2019, 6 pages.

METHOD AND SYSTEM FOR CHARACTERIZING MICROORGANISM-RELATED CONDITIONS

CROSS-REFERENCE TO RELATED APPLICATIONS

This application is continuation-in-part of U.S. application Ser. No. 15/606,743, filed 26 May 2017, which is a continuation of U.S. application Ser. No. 14/919,614, filed 21 Oct. 2015, which claims the benefit of U.S. Provisional Application Ser. No. 62/066,369 filed 21 Oct. 2014, U.S. Provisional Application Ser. No. 62/087,551 filed 4 Dec. 2014, U.S. Provisional Application Ser. No. 62/092,999 filed 17 Dec. 2014, U.S. Provisional Application Ser. No. 62/147,376 filed 14 Apr. 2015, U.S. Provisional Application Ser. No. 62/147,212 filed 14 Apr. 2015, U.S. Provisional Application Ser. No. 62/147,362 filed 14 Apr. 2015, U.S. Provisional Application Ser. No. 62/146,855 filed 13 Apr. 2015, and U.S. Provisional Application Ser. No. 62/206,654 filed 18 Aug. 2015, which are each incorporated in its entirety herein by this reference.

This application additionally claims the benefit of U.S. Provisional Application Ser. No. 62/435,167 filed 16 Dec. 2016, U.S. Provisional Application Ser. No. 62/435,170 filed 16 Dec. 2016, U.S. Provisional Application Ser. No. 62/435,178 filed 16 Dec. 2016, U.S. Provisional Application Ser. No. 62/435,184 filed 16 Dec. 2016, U.S. Provisional Application Ser. No. 62/435,246 filed 16 Dec. 2016, U.S. Provisional Application Ser. No. 62/435,263 filed 16 Dec. 2016, U.S. Provisional Application Ser. No. 62/435,299 filed 16 Dec. 2016, U.S. Provisional Application Ser. No. 62/435,316 filed 16 Dec. 2016, and U.S. Provisional Application Ser. No. 62/435,332 filed 16 Dec. 2016, each of which are incorporated in its entirety by this reference.

This application also claims the benefit of U.S. Provisional Application Ser. No. 62/522,293 filed 20 Jun. 2017, U.S. Provisional Application Ser. No. 62/555,782 filed 8 Sep. 2017, U.S. Provisional Application Ser. No. 62/558,489 filed 14 Sep. 2017, U.S. Provisional Application Ser. No. 62/582,172 filed 6 Nov. 2017, U.S. Provisional Application Ser. No. 62/582,191 filed 6 Nov. 2017, and U.S. Provisional Application Ser. No. 62/582,162 filed 6 Nov. 2017, which are each herein incorporated in their entireties by this reference.

TECHNICAL FIELD

This invention relates generally to the field of microbiology and more specifically to a new and useful method and system for characterizing and/or treating microorganism-related conditions.

BACKGROUND

A microbiome is an ecological community of commensal, symbiotic, and pathogenic microorganisms that are associated with an organism. The human microbiome includes over 10 times more microbial cells than human cells, but characterization of the human microbiome is still in nascent stages due to limitations in sample processing techniques, genetic analysis techniques, and resources for processing large amounts of data. Nonetheless, the microbiome is suspected to play at least a partial role in a number of health/disease-related states (e.g., preparation for childbirth, diabetes, auto-immune disorders, gastrointestinal disorders, rheumatoid disorders, neurological disorders, etc.). Given the profound implications of the microbiome in affecting a subject's health, efforts related to the characterization of the microbiome, the generation of insights from the characterization, and the generation of therapeutics configured to rectify states of dysbiosis should be pursued. Current methods and systems for analyzing the microbiomes of humans and providing therapeutic measures based on gained insights have, however, left many questions unanswered. In particular, methods for characterizing certain health conditions and therapies (e.g., probiotic therapies) tailored to specific subjects based upon microbiome composition and/or functional features have not been viable due to limitations in current technologies.

As such, there is a need in the field of microbiology for a new and useful method and system for characterizing health conditions in an individualized and population-wide manner. This invention creates such a new and useful method and system.

DESCRIPTION OF THE EMBODIMENTS

The following description of the embodiments of the invention is not intended to limit the invention to these embodiments, but rather to enable any person skilled in the art to make and use this invention.

1. Overview

Figure 1A:
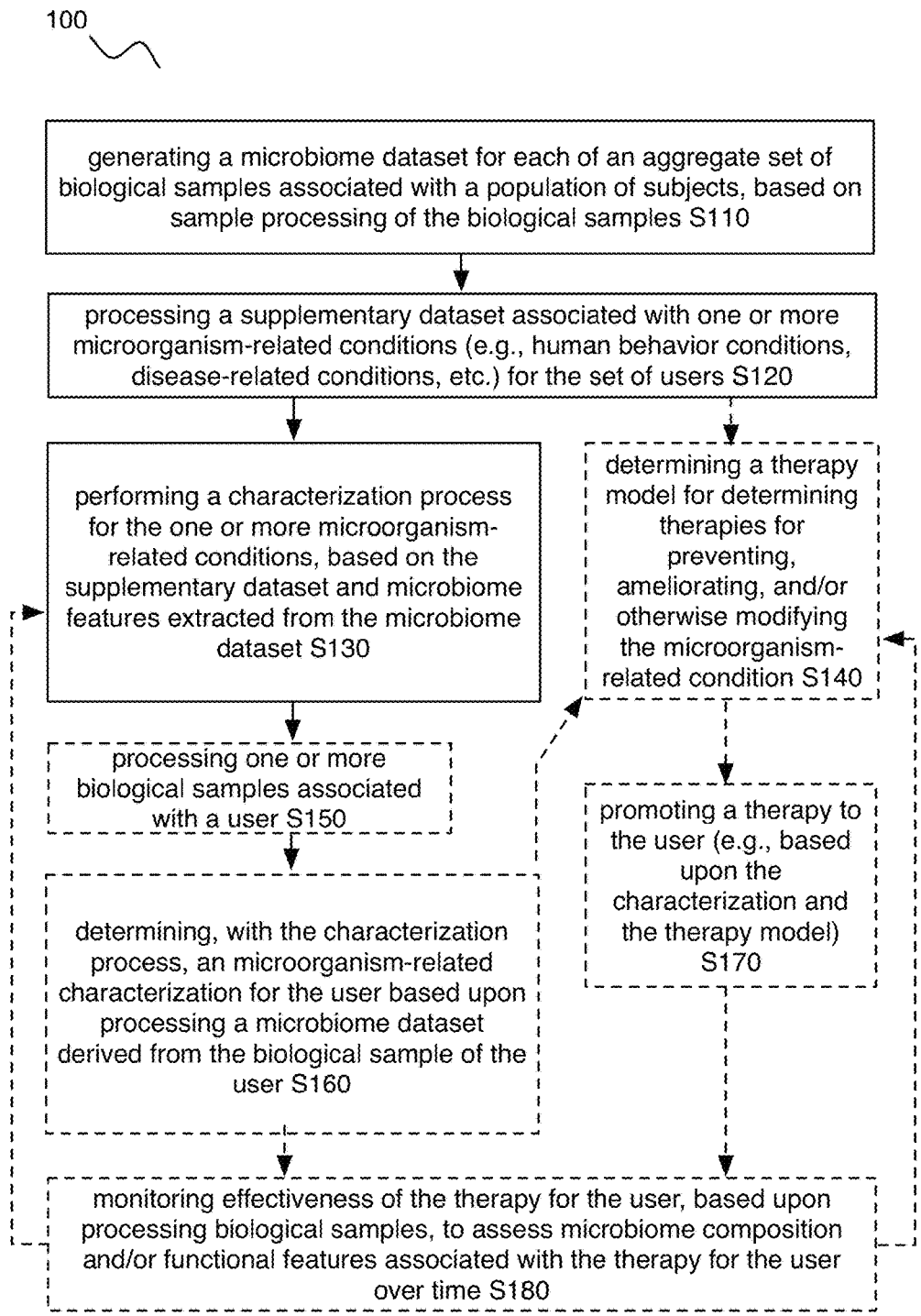
FIGS. 1A-1B are flowchart representations of variations of an embodiment of a method.
Figure 1B:
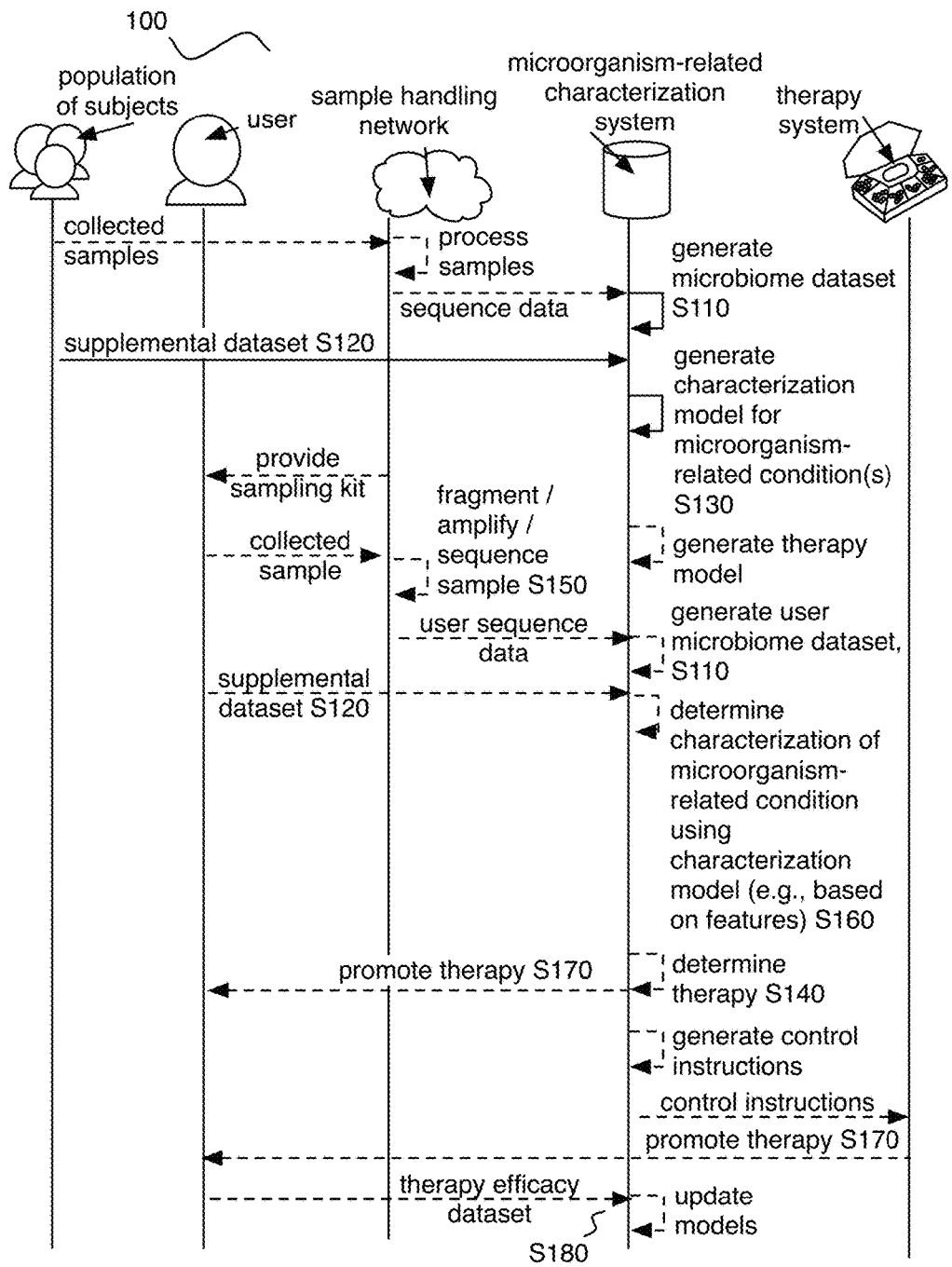

As shown in FIGS. 1A-1B, embodiments of a method 100 for characterizing one or more microorganism-related conditions (e.g., human behavior conditions, disease-related conditions, etc.) associated with microorganisms can include: generating a microbiome dataset (e.g., microorganism sequence dataset, microbiome composition diversity dataset such as based upon a microorganism sequence dataset, microbiome functional diversity dataset such as based upon a microorganism sequence dataset, etc.) for each of an aggregate set of biological samples associated with a population of subjects, based on sample processing of the biological samples S110; processing a supplementary dataset associated with (e.g., informative of; describing; indicative of; correlated with, etc.) one or more microorganism-related conditions (e.g., human behavior conditions, disease-related conditions, etc.) for the set of users S120; and performing a characterization process for the one or more microorganism-related conditions (e.g., human behavior conditions, disease-related conditions, etc.), based on the supplementary dataset and microbiome features (e.g., microbiome composition features such as microbiome composition diversity features; microbiome functional features such as microbiome functional diversity features; microbiome pharmacogenomics features; etc.) extracted from the microbiome dataset S130.

Embodiments of the method 100 can additionally or alternatively include one or more of: determining a therapy model for determining therapies for preventing, ameliorating, and/or otherwise modifying one or more microorganism-related conditions (e.g., human behavior conditions, disease-related conditions, etc.) S140; processing one or more biological samples associated with a user (e.g., subject, human, animal, patient, etc.) S150; determining, with the characterization process, a microorganism-related characterization (e.g., human behavior characterization, disease-related characterization, etc.) for the user based upon processing a user microbiome dataset (e.g., user microorganism sequence dataset, user microbiome composition dataset, user microbiome function dataset, etc.) derived from the biological sample of the user S160; promoting a therapy for the microorganism-related condition to the user (e.g., based upon the microorganism-related characterization and/or a therapy model; etc.) S170; monitoring effectiveness of the therapy for the user, based upon processing biological samples, to assess microbiome composition and/or functional features associated with the therapy for the user over time S180; and/or any other suitable operations.

Embodiments of the method 100 and/or system 200 can function to characterize (e.g., assess, evaluate, diagnose, etc.) and/or treat users in relation to microorganism-related conditions (e.g., human behavior conditions, disease-related conditions, etc.) associated with one or more of: caffeine consumption, alcohol consumption, physical exercise (e.g., extreme physical exercise, moderate physical exercise), menopause, probiotics, habit, diet, Lyme disease, cancer, anemia, and/or other suitable conditions related to microorganisms, such as based on at least one of user microbiome composition (e.g., microbiome composition diversity, etc.), microbiome function (e.g., microbiome functional diversity, etc.), and/or other suitable microbiome-related aspects. Additionally or alternatively, embodiments can function to determine microorganism-related characterizations and/or promote associated therapies in relation to specific physiological sites (e.g., gut, healthy gut, skin, nose, mouth, genitals, other suitable physiological sites, other sample collection sites, etc.). Additionally or alternatively, embodiments can function to generate models (e.g., microorganism-related characterization models such as behavior characterization models and/or disease characterization models; therapy models; etc.) that can be used to characterize and/or diagnose subjects according to at least one of their microbiome composition and functional features (e.g., as a clinical diagnostic, as a companion diagnostic, etc.), and/or provide therapeutic measures (e.g., probiotic-based therapeutic measures, phage-based therapeutic measures, small-molecule-based therapeutic measures, clinical measures, etc.) to subjects in relation to one or more microorganism-related conditions (e.g., human behavior conditions, disease-related conditions, etc.). Additionally or alternatively, embodiments can perform any suitable functionality described herein.

As such, data from a population of subjects can be used to characterize subjects according to their microbiome composition and/or functional features, indicate states of health and areas of improvement based upon the characterization(s), and promote one or more therapies that can modulate the composition of a subject's microbiome toward one or more of a set of desired equilibrium states (e.g., correlated with improved health states associated with one or more microorganism-related conditions; etc.). Variations of the method 100 can further facilitate monitoring and/or adjusting of therapies provided to a subject, for instance, through reception, processing, and analysis of additional samples from a subject over time (e.g., throughout the course of a therapy regimen, through the extent of a user's experiences with microorganism-related conditions; etc.), which can facilitate therapy efficacy monitoring and/or therapy adjustment, microbiome characterization and/or related therapies over time, and/or performance of any suitable portion of the method 100 (e.g., over time, etc.).

Embodiments of the method 100 and/or system 200 can preferably generate and/or promote (e.g., provide) characterizations and/or therapies for one or more microorganism-related conditions (e.g., human behavior conditions, disease-related conditions, etc.), which can include one or more of: behaviors (e.g., caffeine consumption, habits, diets, etc.), symptoms, causes (e.g., triggers, etc.), diseases, disorders, associated risk, associated severity, and/or any other suitable aspects associated with microorganism-related conditions. Microorganism-related conditions can include one or more human behavior conditions which can include any one or more of: caffeine consumption, alcohol consumption, other food item consumption, dietary supplement consumption, probiotic-related behaviors (e.g., consumption, avoidance, etc.), other dietary behaviors, habituary behaviors (e.g., smoking; exercise conditions such as low, moderate, and/or extreme exercise conditions; etc.), menopause, other biological processes, social behavior, other behaviors, and/or any other suitable human behavior conditions. Additionally or alternatively, microorganism-related conditions can include one or more disease-related conditions, which can include any one or more of: cancer conditions (e.g., lymphoma; leukemia; blastoma; germ cell tumor; carcinoma; sarcoma; breast cancer; prostate cancer; basal cell cancer; skin cancer; colon cancer; lung cancer; cancer conditions associated with any suitable physiological region; etc.), anemia conditions (e.g., thalassemia; sickle cell; pernicious; fanconi; haemolyitic; aplastic; iron deficiency; etc.), Lyme disease conditions, psychiatric and behavioral conditions, communication-related conditions, sleep-related conditions, a cardiovascular-related condition, metabolic-related conditions, rheumatoid-related conditions, weight-related conditions, pain-related conditions, endocrine-related conditions, genetic-related conditions, chronic disease, and/or any other suitable type of disease-related conditions.

Embodiments of the method 100 and/or system 200 can be implemented for a single user for whom microbiome characterization and/or microbiome modulation with therapeutics is of interest, and/or can additionally or alternatively be implemented for a population of subjects (e.g., including the user, excluding the users), where the population of subjects can include other users dissimilar to and/or similar to the user (e.g., in health condition, in dietary needs, in demographic features, in behavior, in microbiome composition and/or function, etc.); for a subgroup of users (e.g., sharing characteristics, such as characteristics affecting microbiome characterization and/or therapy determination; etc.). Thus, information derived from a set of users (e.g., population of subjects, set of subjects, subgroup of users, etc.) can be used to provide additional insight into connections between behaviors of a subject and effects on the patient's microbiome, due to aggregation of data from the set of users. In a variation, an aggregate set of biological samples is preferably received from a wide variety of users, collectively including users of one or more of: different demographics (e.g., genders, ages, marital statuses, ethnicities, nationalities, socioeconomic statuses, sexual orientations, etc.), different health conditions (e.g., health and disease states; different microorganism-related conditions; different genetic dispositions; etc.), different living situations (e.g., living alone, living with pets, living with a significant other, living with children, etc.), different dietary habits (e.g., omnivorous, vegetarian, vegan, sugar consumption, acid consumption, caffeine consumption, etc.), different behavioral tendencies (e.g., levels of physical activity, drug use, alcohol use, etc.), different levels of mobility (e.g., related to distance traveled within a given time period), and/or any other suitable trait (e.g., behaviors, such as human behavior conditions, etc.) associated with (e.g., has an effect on, etc.) microbiome composition and/or functional features. As such, as the number of users increases, the predictive power of processes implemented in portions of the method 100 can increase, such as in relation to characterizing a variety of users based upon their microbiomes. However, the method 100 can involve generation of characterization and therapies derived from biological sample data from any other suitable group of users.

Data described herein (e.g., sequence data, microbiome composition features, microbiome functional features, microorganism-related characterizations therapy determinations, etc.) can be associated with any suitable temporal indicators (e.g., seconds, minutes, hours, days, weeks, etc.) including one or more: temporal indicators indicating when the data was collected (e.g., temporal indicators indicating when a sample was collected; etc.), determined, transmitted, received, and/or otherwise processed; temporal indicators providing context to content described by the data (e.g., temporal indicators associated with microorganism-related characterizations, such as where the microorganism-related characterization describes the microorganism-related conditions and/or user microbiome status at a particular time; etc.); changes in temporal indicators (e.g., changes in microorganism-related characterizations over time, such as in response to receiving a therapy; latency between sample collection, sample analysis, provision of a microorganism-related characterization or therapy to a user, and/or other suitable portions of the method 100; etc.); and/or any other suitable indicators related to time.

Additionally or alternatively, parameters, metrics, inputs, outputs, and/or other suitable data can be associated with value types including: scores (e.g., microbiome diversity scores; aggregate microbiome scores based on individual microbiome scores for different collection sites; risk scores for microorganism-related conditions; severity scores for microorganism-related conditions; microbiome composition diversity scores; microbiome functional diversity scores; etc.), binary values (e.g., presence or absence of a microbiome feature; presence or absence of a microorganism-related condition; etc.), relative values (e.g., relative taxonomic group abundance, relative microbiome function abundance, relative feature abundance, etc.), classifications (e.g., microorganism-related condition classifications for different types of behaviors and/or diseases; demographic classifications; etc.), confidence levels (e.g., associated with microorganism sequence datasets; with microbiome diversity scores; with other microorganism-related characterizations; with other outputs; etc.), values along a spectrum, and/or any other suitable types of values. Any suitable types of data described herein can be used as inputs (e.g., for different models described herein), generated as outputs (e.g., of different models), and/or manipulated in any suitable manner for any suitable components associated with the method 100 and/or system 200.

One or more instances and/or portions of the method 100 and/or processes described herein can be performed asynchronously (e.g., sequentially), concurrently (e.g., multiplex sample processing, such as multiplex amplification of microorganism nucleic acid fragments corresponding to target sequences associated with microorganism-related conditions; performing sample processing and analysis for substantially concurrently evaluating a panel of microorganism-related conditions; computationally determining microbiome datasets, microbiome features, and/or microorganism-related conditions in parallel for a plurality of users, such as concurrently on different threads for parallel computing to improve system processing ability; etc.), in temporal relation (e.g., substantially concurrently with, in response to, serially, prior to, subsequent to, etc.) to a trigger event (e.g., performance of a portion of the method 100), and/or in any other suitable order at any suitable time and frequency by and/or using one or more instances of the system 200, components, and/or entities described herein. For example, the method 100 can include generating a microorganism sequence dataset based on processing microorganism nucleic acids of a biological sample with a bridge amplification substrate of a next generation sequencing platform of a sample handling system, and determining microbiome composition diversity features and microbiome functional diversity features at computing devices operable to communicate with the next generation sequencing platform.

Figure 2:
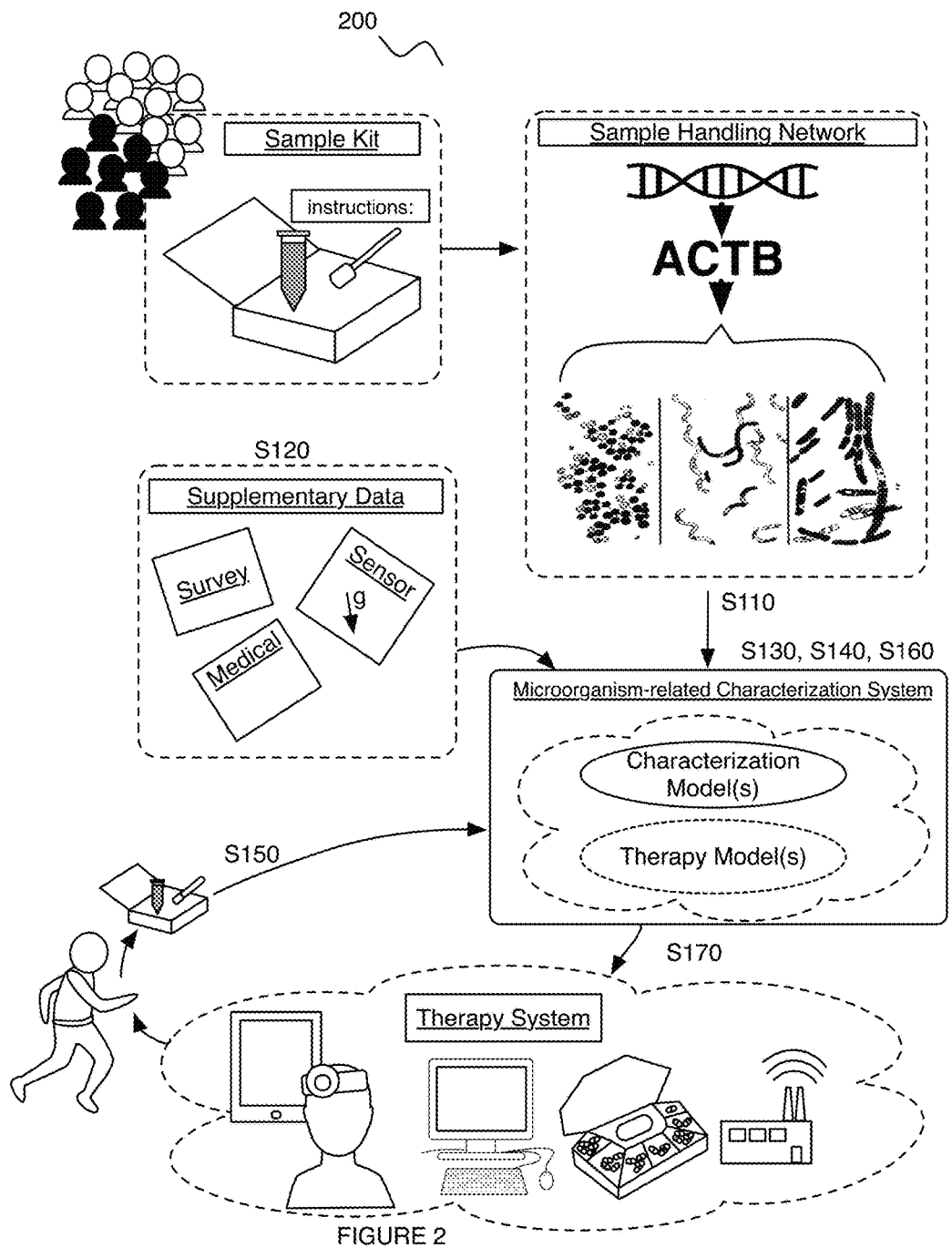
FIG. 2 depicts embodiments of a method and system.

As shown in FIG. 2, embodiments of the system 200 can include any one or more of: a handling system (e.g., a sample handling system, etc.) operable to collect biological samples (e.g., collected by users and included in containers including pre-processing reagents; etc.) from one or more users (e.g., a human subject, patient, animal subject, environmental ecosystem, care provider, etc.), the handling system including a sequencing platform (e.g., next-generation sequencing platform) operable to determine a microorganism sequence dataset for the one or more users from the biological samples; a microorganism-related characterization (e.g., human behavior characterization, disease-related characterization, etc.) system operable to: determine user microbiome features (e.g., microbiome composition features; microbiome functional features; diversity features; relative abundance ranges; etc.) based on the microorganism sequence dataset (and/or other suitable data described herein), and determine microorganism-related characterizations (e.g., human behavior characterizations, disease-related characterizations, based on the user microbiome features; etc.) and/or a treatment system operable to promote a therapy for one or more microorganism-related conditions based on the microorganism-related characterization. However, the method 100 and/or system 200 can be configured in any suitable manner.

2. Benefits

Microbiome analysis can enable accurate and/or efficient characterization and/or therapy provision (e.g., according to portions of the method 100, etc.) for microorganism-related conditions caused by and/or otherwise associated with microorganisms. The technology can overcome several challenges faced by conventional approaches in characterizing a user condition (e.g., microorganism-related condition) and/or promoting associated therapies. First, conventional approaches can require patients to visit one or more care providers to receive a characterization and/or a therapy recommendation for a microorganism-related condition (e.g., through diagnostic medical procedures such as blood testing; etc.), which can amount to inefficiencies and/or health-risks associated with the amount of time elapsed before diagnosis and/or treatment, with inconsistency in healthcare quality, and/or with other aspects of care provider visitation. Second, conventional genetic sequencing and analysis technologies for human genome sequencing can be incompatible and/or inefficient when applied to the microbiome (e.g., where the human microbiome can include over 10 times more microbial cells than human cells; where optimal sample processing techniques can differ, such as for reducing amplification bias; where different approaches to microorganism-related characterizations can be employed; where the types of conditions and correlations can differ; where sequence reference databases can differ; where the microbiome can vary across different body regions of the user; etc.). Third, the onset of sequencing technologies (e.g., next-generation sequencing) has given rise to technological issues (e.g., data processing and analysis issues for the plethora of generated sequence data; issues with processing a plurality of biological samples in a multiplex manner; information display issues; therapy prediction issues, therapy provision issues, etc.) that would not exist but for the unprecedented advances in speed and data generation associated with sequencing genetic material. Specific examples of the method 100 and/or system 200 can confer technologically-rooted solutions to at least the challenges described above.

First, the technology can transform entities (e.g., users, biological samples, treatment systems including medical devices, etc.) into different states or things. For example, the technology can transform a biological sample into components able to be sequenced and analyzed for characterizing users in relation to microorganism-related conditions (e.g., using next-generation sequencing systems; multiplex amplification operations; etc.). In another example, the technology can identify therapies (e.g., personalized therapies based on a microbiome characterization; etc.) to promote to a user to modify a microbiome composition (e.g., composition diversity), microbiome function (e.g., functional diversity) and/or other microbiome-related aspects to prevent and/or ameliorate one or more microorganism-related conditions, thereby transforming the microbiome and/or health of the patient (e.g., improving a health state associated with a microorganism-related condition; etc.). In another example, the technology can transform microbiome composition and/or function at one or more different physiological sites of a user, such as targeting and/or transforming microorganisms associated with a gut, nose, skin, mouth, and/or genitals microbiome. In another example, the technology can control treatment-related systems (e.g., automated medication dispensers; behavior modification systems; diagnostic systems; disease treatment systems; etc.) to promote therapies (e.g., by generating control instructions for the treatment system to execute; etc.), thereby transforming the treatment system.

Second, the technology can confer improvements in computer-related technology (e.g., modeling associated with characterizing and/or promoting therapies for microorganism-related conditions; improving computational efficiency in storing, retrieving, and/or processing microorganism-related data for microorganism-related conditions; computational processing associated with biological sample processing; etc.) by facilitating computer performance of functions not previously performable. For example, the technology can computationally generate microorganism-related characterizations and/or recommended therapies associated with microbiome analysis based on techniques (e.g., leveraging microorganism taxonomic databases, etc.) that are recently viable due to advances in sample processing techniques and/or sequencing technology.

Third, the technology can confer improvements in processing speed, microorganism-related characterization (e.g., human behavior characterization, disease-related characterization, etc.) accuracy, microbiome-related therapy determination and promotion, and/or other suitable aspects in relation to microorganism-related conditions. For example, the technology can generate and apply feature-selection rules (e.g., microbiome feature-selection rules for composition, function; for supplemental features extracted from supplementary datasets; etc.) to select an optimized subset of features (e.g., microbiome composition diversity features such as reference relative abundance features indicative of healthy, presence, absence, and/or other suitable ranges of taxonomic groups associated with microorganism-related conditions; user relative abundance features that can be compared to reference relative abundance features correlated with microorganism-related conditions and/or therapy responses; etc.) out of a vast potential pool of features (e.g., extractable from the plethora of microbiome data such as sequence data) for generating and/or applying characterization models and/or therapy models. The potential size of microbiomes (e.g., human microbiomes, animal microbiomes, etc.) can translate into a plethora of data, giving rise to questions of how to process and analyze the vast array of data to generate actionable microbiome insights in relation to microorganism-related conditions. However, the feature-selection rules and/or other suitable computer-implementable rules can enable one or more of: shorter generation and execution times (e.g., for generating and/or applying models; for determining microorganism-related characterizations and/or associated therapies; etc.); optimized sample processing techniques (e.g., improving transformation of microorganism nucleic acids from biological samples through using primer types, other biomolecules, and/or other sample processing components identified through computational analysis of taxonomic groups, sequences, and/or other suitable data associated with microorganism-related conditions, such as while optimizing for improving specificity, reducing amplification bias, and/or other suitable parameters; etc.); model simplification facilitating efficient interpretation of results; reduction in overfitting; network effects associated with generating, storing, and applying microbiome characterizations for a plurality of users over time in relation to microorganism-related conditions (e.g., through collecting and processing an increasing amount of microbiome-related data associated with an increasing number of users to improve predictive power of the microorganism-related characterizations and/or therapy determinations; etc.); improvements in data storage and retrieval (e.g., storing specific models such as in association with different users and/or sets of users; storing microbiome datasets in association with user accounts; storing therapy monitoring data in association with one or more therapies and/or users receiving the therapies; storing features, microorganism-related characterizations, and/or other suitable data in association with a user and/or set of users to improve delivery of personalized characterizations and/or treatments for the microorganism-related conditions, etc.), and/or other suitable improvements to technological areas.

Fourth, the technology can amount to an inventive distribution of functionality across a network including a sample handling system, a microorganism-related characterization (e.g., human behavior characterization, disease-related characterization, etc.) system, and a plurality of users, where the sample handling system can handle substantially concurrent processing of biological samples (e.g., in a multiplex manner) from the plurality of users, which can be leveraged by the microorganism-related characterization (e.g., human behavior characterization, disease-related characterization, etc.) system in generating personalized characterizations and/or therapies (e.g., customized to the user's microbiome such as in relation to the user's dietary behavior, probiotics-associated behavior, medical history, demographics, other behaviors, preferences, etc.) for microorganism-related conditions.

Fifth, the technology can improve the technical fields of at least microbiome-related digital medicine, digital medicine generally, genetic sequencing, modeling (e.g., of microorganism-related conditions such as human behavior conditions and disease-related conditions; etc.) and/or other relevant fields. Sixth, the technology can leverage specialized computing devices (e.g., devices associated with the sample handling system, such as next-generation sequencing platforms; microorganism-related characterization (e.g., human behavior characterization, disease-related characterization, etc.) systems; treatment systems; etc.) in determining and processing microbiome datasets in relation to microorganism-related characterization (e.g., human behavior characterization, disease-related characterization, etc.) and/or therapy provision. The technology can, however, provide any other suitable benefit(s) in the context of using non-generalized computer systems for microorganism-related characterization (e.g., human behavior characterization, disease-related characterization, etc.), microbiome modulation, and/or for performing other suitable portions of the method 100.

3.1 Generating a Microbiome Dataset.

Block S110 recites: generating a microbiome dataset (e.g., microorganism sequence dataset, microbiome composition diversity dataset, microbiome functional diversity dataset, etc.) for each of an aggregate set of biological samples associated with a population of users (e.g., subjects), based on sample processing of the biological samples. Block Silo functions to process each of an aggregate set of biological samples (e.g., associated with a population of subjects, a subpopulation of subjects, a subgroup of subjects sharing a demographic characteristic and/or other suitable characteristics, etc.), in order to determine compositional, functional, pharmacogenomics, and/or other suitable aspects associated with the microbiomes of the users, such as in relation to one or more microorganism-related conditions. Compositional and/or functional aspects can include one or more of aspects at the microorganism level (and/or other suitable granularity), including parameters related to distribution of microorganisms across different groups of kingdoms, phyla, classes, orders, families, genera, species, subspecies, strains, and/or any other suitable infraspecies taxon (e.g., as measured in total abundance of each group, relative abundance of each group, total number of groups represented, etc.). Compositional and/or functional aspects can also be represented in terms of operational taxonomic units (OTUs). Compositional and/or functional aspects can additionally or alternatively include compositional aspects at the genetic level (e.g., regions determined by multilocus sequence typing, 16S sequences, 18S sequences, ITS sequences, other genetic markers, other phylogenetic markers, etc.). Compositional and functional aspects can include the presence or absence or the quantity of genes associated with specific functions (e.g. enzyme activities, transport functions, immune activities, etc.). Outputs of Block S110 can thus be used to provide features of interest for the characterization process of Block S130 and/or other suitable portions of the method 100 (e.g., where Block S110 can lead to outputs of microbiome composition datasets, microbiome functional datasets, and/or other suitable microbiome datasets from which microbiome features can be extracted, etc.), where the features can be microorganism-based (e.g., presence of a genus of bacteria), genetic-based (e.g., based upon representation of specific genetic regions and/or sequences) and/or functional-based (e.g., presence of a specific catalytic activity).

In a variation, Block S110 can include assessment and/or processing based upon phylogenetic markers derived from bacteria and/or archaea in relation to gene families associated with one or more of: ribosomal protein S2, ribosomal protein S3, ribosomal protein S5, ribosomal protein S7, ribosomal protein S8, ribosomal protein S9, ribosomal protein S10, ribosomal protein S11, ribosomal protein S12/S23, ribosomal protein S13, ribosomal protein S15P/S13e, ribosomal protein S17, ribosomal protein S19, ribosomal protein L1, ribosomal protein L2, ribosomal protein L3, ribosomal protein L4/L1e, ribosomal protein L5, ribosomal protein L6, ribosomal protein L10, ribosomal protein L11, ribosomal protein L14b/L23e, ribosomal protein L15, ribosomal protein L16/L10E, ribosomal protein L18P/L5E, ribosomal protein L22, ribosomal protein L24, ribosomal protein L25/L23, ribosomal protein L29, translation elongation factor EF-2, translation initiation factor IF-2, metalloendopeptidase, ffh signal recognition particle protein, phenylalanyl-tRNA synthetase beta subunit, phenylalanyl-tRNA synthetase alpha subunit, tRNA pseudouridine synthase B, Porphobilinogen deaminase, ribosomal protein L13, phosphoribosylformylglycinamidine cyclo-ligase, and ribonuclease HII. Additionally or alternatively, markers can include target sequences (e.g., sequences associated with a microorganism taxonomic group; sequences associated with functional aspects; sequences correlated with microorganism-related conditions; sequences indicative of user responsiveness to different therapies; sequences that are invariant across a population and/or any suitable set of subjects, such as to facilitate multiplex amplification using a primer type sharing a primer sequence; conserved sequences; sequences including mutations, polymorphisms; nucleotide sequences; amino acid sequences; etc.), proteins (e.g., serum proteins, antibodies, etc.), peptides, carbohydrates, lipids, other nucleic acids, whole cells, metabolites, natural products, genetic predisposition biomarkers, diagnostic biomarkers, prognostic biomarkers, predictive biomarkers, other molecular biomarkers, gene expression markers, imaging biomarkers, and/or other suitable markers. However, markers can include any other suitable marker(s) associated with microbiome composition, microbiome functionality, and/or microorganism-related conditions.

Characterizing the microbiome composition and/or functional aspects for each of the aggregate set of biological samples thus preferably includes a combination of sample processing techniques (e.g., wet laboratory techniques), including, but not limited to, amplicon sequencing (i.e 16S, 18S, ITS), UMIs, 3 step PCR, Crispr, metagenomic approaches, metatranscriptomics, use of random primers, and computational techniques (e.g., utilizing tools of bioinformatics), to quantitatively and/or qualitatively characterize the microbiome and functional aspects associated with each biological sample from a subject or population of subjects.

In variations, sample processing in Block S110 can include any one or more of: lysing a biological sample, disrupting membranes in cells of a biological sample, separation of undesired elements (e.g., RNA, proteins) from the biological sample, purification of nucleic acids (e.g., DNA) in a biological sample, amplification of nucleic acids from the biological sample, further purification of amplified nucleic acids of the biological sample, and sequencing of amplified nucleic acids of the biological sample. In an example, Block S110 can include: collecting biological samples from a set of users (e.g., biological samples collected by the user with a sampling kit including a sample container, etc.), where the biological samples include microorganism nucleic acids associated with the microorganism-related condition (e.g., microorganism nucleic acids including target sequences correlated with a microorganism-related condition; etc.). In another example, Block S110 can include providing a set of sampling kits to a set of users, each sampling kit of the set of sampling kits including a sample container (e.g., including pre-processing reagents, such as lysing reagents; etc.) operable to receive a biological sample from a user of the set of users.

In variations, lysing a biological sample and/or disrupting membranes in cells of a biological sample preferably includes physical methods (e.g., bead beating, nitrogen decompression, homogenization, sonication), which omit certain reagents that produce bias in representation of certain bacterial groups upon sequencing. Additionally or alternatively, lysing or disrupting in Block S110 can involve chemical methods (e.g., using a detergent, using a solvent, using a surfactant, etc.). Additionally or alternatively, lysing or disrupting in Block S110 can involve biological methods. In variations, separation of undesired elements can include removal of RNA using RNases and/or removal of proteins using proteases. In variations, purification of nucleic acids can include one or more of: precipitation of nucleic acids from the biological samples (e.g., using alcohol-based precipitation methods), liquid-liquid based purification techniques (e.g., phenol-chloroform extraction), chromatography-based purification techniques (e.g., column adsorption), purification techniques involving use of binding moiety-bound particles (e.g., magnetic beads, buoyant beads, beads with size distributions, ultrasonically responsive beads, etc.) configured to bind nucleic acids and configured to release nucleic acids in the presence of an elution environment (e.g., having an elution solution, providing a pH shift, providing a temperature shift, etc.), and any other suitable purification techniques.

In variations, amplification of purified nucleic acids can include one or more of: polymerase chain reaction (PCR)-based techniques (e.g., solid-phase PCR, RT-PCR, qPCR, multiplex PCR, touchdown PCR, nanoPCR, nested PCR, hot start PCR, etc.), helicase-dependent amplification (HDA), loop mediated isothermal amplification (LAMP), self-sustained sequence replication (3SR), nucleic acid sequence based amplification (NASBA), strand displacement amplification (SDA), rolling circle amplification (RCA), ligase chain reaction (LCR), and any other suitable amplification technique. In amplification of purified nucleic acids, the primers used are preferably selected to prevent or minimize amplification bias, as well as configured to amplify nucleic acid regions/sequences (e.g., of the 16S region, the 18S region, the ITS region, etc.) that are informative taxonomically, phylogenetically, for diagnostics, for formulations (e.g., for probiotic formulations), and/or for any other suitable purpose. Thus, universal primers (e.g., a F27-R338 primer set for 16S RNA, a F515-R806 primer set for 16S RNA, etc.) configured to avoid amplification bias can be used in amplification. Additionally or alternatively include incorporated barcode sequences and/or UMIsspecific to biological samples, to users, to microorganism-related conditions, to taxa, to target sequences, and/or to any other suitable components, which can facilitate a post-sequencing identification process (e.g., for mapping sequence reads to microbiome composition and/or microbiome function aspects; etc.). Primers used in variations of Block S110 can additionally or alternatively include adaptor regions configured to cooperate with sequencing techniques involving complementary adaptors (e.g., Illumina Sequencing). Additionally or alternatively, Block S110 can implement any other step configured to facilitate processing (e.g., using a Nextera kit). In a specific example, performing amplification and/or sample processing operations can be in a multiplex manner (e.g., for a single biological sample, for a plurality of biological samples across multiple users; etc.). In another specific example, performing amplification can include normalization steps to balance libraries and detect all amplicons in a mixture independent of the amount of starting material, such as 3 step PCR, bead based normalization, etc.

In variations, sequencing of purified nucleic acids can include methods involving targeted amplicon sequencing, metatranscriptomic sequencing, and/or metagenomic sequencing, implementing techniques including one or more of: sequencing-by-synthesis techniques (e.g., Illumina sequencing), capillary sequencing techniques (e.g., Sanger sequencing), pyrosequencing techniques, and nanopore sequencing techniques (e.g., using an Oxford Nanopore technique).

In a specific example, amplification and sequencing of nucleic acids from biological samples of the set of biological samples includes: solid-phase PCR involving bridge amplification of DNA fragments of the biological samples on a substrate with oligo adapters, where amplification involves primers having a forward index sequence (e.g., corresponding to an Illumina forward index for MiSeq/NextSeq/HiSeq platforms), a forward barcode sequence, a transposase sequence (e.g., corresponding to a transposase binding site for MiSeq/NextSeq/HiSeq platforms), a linker (e.g., a zero, one, or two-base fragment configured to reduce homogeneity and improve sequence results), an additional random base, UMIs, a sequence for targeting a specific target region (e.g., 16S region, 18S region, ITS region), a reverse index sequence (e.g., corresponding to an Illumina reverse index for MiSeq/HiSeq platforms), and a reverse barcode sequence. In the specific example, sequencing can include Illumina sequencing (e.g., with a HiSeq platform, with a MiSeq platform, with a NextSeq platform, etc.) using a sequencing-by-synthesis technique. In another specific example, the method 100 can include: identifying one or more primer types compatible with one or more genetic targets associated with one or more microorganism-related conditions (e.g., human behavior conditions, disease-related conditions, etc.); generating a microorganism dataset (e.g., microorganism sequence dataset, etc.) for one or more users (e.g., set of subjects) based on the one or more primer types (e.g., and the microorganism nucleic acids included in collected biological samples, etc.), such as through fragmenting the microorganism nucleic acids, and and/or performing multiplex amplification with the fragmented microorganism nucleic acids based on the one or more identified primer types compatible with the genetic target associated with the human behavior condition; and/or promoting (e.g., providing), based on a microbiome characterization derived from the a microorganism dataset a therapy for the user condition (e.g., enabling selective modulation of a microbiome of the user in relation to at least one of a population size of a desired taxon and a desired microbiome function, etc.).

In variations, primers (e.g., of a primer type corresponding to a primer sequence; etc.) used in Block S110 and/or other suitable portions of the method 100 can include primers associated with protein genes (e.g., coding for conserved protein gene sequences across a plurality of taxa, such as to enable multiplex amplification for a plurality of targets and/or taxa; etc.). Primers can additionally or alternatively be associated with microorganism-related conditions (e.g., primers compatible with genetic targets including microorganism sequence biomarkers for microorganisms correlated with microorganism-related conditions such as human behavior conditions and/or disease-related conditions; etc.), microbiome composition features (e.g., identified primers compatible with a genetic target corresponding to microbiome composition features associated with a group of taxa correlated with a microorganism-related condition; genetic sequences from which relative abundance features are derived etc.), functional diversity features, supplementary features, and/or other suitable features and/or data. Primers (and/or other suitable molecules, markers, and/or biological material described herein) can possess any suitable size (e.g., sequence length, number of base pairs, conserved sequence length, variable region length, etc.). Additionally or alternatively, any suitable number of primers can be used in sample processing for performing characterizations (e.g., microorganism-related characterizations; etc.), improving sample processing (e.g., through reducing amplification bias, etc.), and/or for any suitable purposes. The primers can be associated with any suitable number of targets, sequences, taxa, conditions, and/or other suitable aspects. Primers used in Block S110 and/or other suitable portions of the method 100 can be selected through processes described in Block S110 (e.g., primer selection based on parameters used in generating the taxonomic database) and/or any other suitable portions of the method 100. In an example, Block S110 can include: identifying a primer type for a microorganism nucleic acid sequence associated with the microorganism-related condition (e.g., a primer type for a primer operable to amplify microorganism nucleic acid sequences correlated with a microorganism-related condition; etc.); and generating the microorganism sequence dataset based on the primer type and the microorganism nucleic acids (e.g., using primers of the primer type for amplification of microorganism nucleic acids; and sequencing the amplified nucleic acids to generate the microorganism sequence dataset; etc.). In a specific example, Block S110 can include: fragmenting the microorganism nucleic acids; and performing multiplex amplification with the fragmented microorganism nucleic acids based on the fragmented microorganism nucleic acids and the identified primer type associated with the microorganism-related condition. Additionally or alternatively, primers (and/or processes associated with primers) can include and/or be analogous to that described in U.S. application Ser. No. 14/919,614, filed 21 Oct. 2015, which is herein incorporated in its entirety by this reference. However, identification and/or usage of primers can be configured in any suitable manner.

Some variations of sample processing can include further purification of amplified nucleic acids (e.g., PCR products) prior to sequencing, which functions to remove excess amplification elements (e.g., primers, dNTPs, enzymes, salts, etc.). In examples, additional purification can be facilitated using any one or more of: purification kits, buffers, alcohols, pH indicators, chaotropic salts, nucleic acid binding filters, centrifugation, and/or any other suitable purification technique.

In variations, computational processing in Block S110 can include any one or more of: identification of microbiome-derived sequences (e.g., as opposed to subject sequences and contaminants), alignment and mapping of microbiome-derived sequences (e.g., alignment of fragmented sequences using one or more of single-ended alignment, ungapped alignment, gapped alignment, pairing), and generating features associated with (e.g., derived from) compositional and/or functional aspects of the microbiome associated with a biological sample.

Identification of microbiome-derived sequences can include mapping of sequence data from sample processing to a subject reference genome (e.g., provided by the Genome Reference Consortium), in order to remove subject genome-derived sequences. Unidentified sequences remaining after mapping of sequence data to the subject reference genome can then be further clustered into operational taxonomic units (OTUs) based upon sequence similarity and/or reference-based approaches (e.g., using VAMPS, using MG-RAST, using QIIME databases), aligned (e.g., using a genome hashing approach, using a Needleman-Wunsch algorithm, using a Smith-Waterman algorithm), and mapped to reference bacterial genomes (e.g., provided by the National Center for Biotechnology Information), using an alignment algorithm (e.g., Basic Local Alignment Search Tool, FPGA accelerated alignment tool, BWT-indexing with BWA, BWT-indexing with SOAP, BWT-indexing with Bowtie, etc.). Mapping of unidentified sequences can additionally or alternatively include mapping to reference archaeal genomes, viral genomes and/or eukaryotic genomes. Furthermore, mapping of taxons can be performed in relation to existing databases, and/or in relation to custom-generated databases.

Upon identification of represented groups of microorganisms of the microbiome associated with a biological sample, generating features associated with (e.g., derived from) compositional and functional aspects of the microbiome associated with a biological sample can be performed. In a variation, generating features can include generating features based upon multilocus sequence typing (MSLT), in order to identify markers useful for characterization in subsequent blocks of the method 100. Additionally or alternatively, generated features can include generating features that describe the presence or absence of certain taxonomic groups of microorganisms, and/or ratios between exhibited taxonomic groups of microorganisms. Additionally or alternatively, generating features can include generating features describing one or more of: quantities of represented taxonomic groups, networks of represented taxonomic groups, correlations in representation of different taxonomic groups, interactions between different taxonomic groups, products produced by different taxonomic groups, interactions between products produced by different taxonomic groups, ratios between dead and alive microorganisms (e.g., for different represented taxonomic groups, based upon analysis of RNAs), phylogenetic distance (e.g., in terms of Kantorovich-Rubinstein distances, Wasserstein distances etc.), any other suitable taxonomic group-related feature(s), any other suitable genetic or functional aspect(s).

Additionally or alternatively, generating features can include generating features describing relative abundance of different microorganism groups, for instance, using a sparCC approach, using Genome Relative Abundance and Average size (GAAS) approach and/or using a Genome Relative Abundance using Mixture Model theory (GRAMMy) approach that uses sequence-similarity data to perform a maximum likelihood estimation of the relative abundance of one or more groups of microorganisms. Additionally or alternatively, generating features can include generating statistical measures of taxonomic variation, as derived from abundance metrics. Additionally or alternatively, generating features can include generating features associated with (e.g., derived from) relative abundance factors (e.g., in relation to changes in abundance of a taxon, which affects abundance of other taxons). Additionally or alternatively, generating features can include generation of qualitative features describing presence of one or more taxonomic groups, in isolation and/or in combination. Additionally or alternatively, generating features can include generation of features related to genetic markers (e.g., representative 16S, 18S, and/or ITS sequences) characterizing microorganisms of the microbiome associated with a biological sample. Additionally or alternatively, generating features can include generation of features related to functional associations of specific genes and/or organisms having the specific genes. Additionally or alternatively, generating features can include generation of features related to pathogenicity of a taxon and/or products attributed to a taxon. Block S120 can, however, include generation of any other suitable feature(s) derived from sequencing and mapping of nucleic acids of a biological sample. For instance, the feature(s) can be combinatory (e.g. involving pairs, triplets), correlative (e.g., related to correlations between different features), and/or related to changes in features (e.g., temporal changes, changes across sample sites, etc., spatial changes, etc.). However, processing biological samples, generating a microbiome dataset, and/or other aspects associated with Block S110 can be performed in any suitable manner.

3.2 Processing a Supplementary Dataset.

Block S120 recites: processing (e.g., receiving, collecting, transforming, etc.) a supplementary dataset associated with (e.g., informative of; describing; indicative of; etc.) one or more microorganism-related conditions (e.g., human behavior condition such as associated with user behavior; disease related condition such as associated medical history, symptoms, medications; etc.) for the set of users. Block S120 can function to acquire data associated with one or more subjects of the set of subjects, which can be used to train, validate, apply, and/or otherwise inform the microorganism-related characterization (e.g., human behavior characterization, disease-related characterization, etc.) process (e.g., in Block S130). In Block S120, the supplementary dataset preferably includes survey-derived data, but can additionally or alternatively include any one or more of: contextual data derived from sensors (e.g., wearable device data, etc.), medical data (e.g., current and historical medical data; medical device-derived data; data associated with medical tests; etc.), social media data, mobile phone data (e.g., mobile phone application data, etc.), web application data, and/or any other suitable type of data. In variations of Block S120 including reception of survey-derived data, the survey-derived data preferably provides physiological, demographic, and behavioral information in association with a subject. Physiological information can include information related to physiological features (e.g., height, weight, body mass index, body fat percent, body hair level, etc.). Demographic information can include information related to demographic features (e.g., gender, age, ethnicity, marital status, number of siblings, socioeconomic status, sexual orientation, etc.). Behavioral information can include information related to one or more of: health conditions (e.g., health and disease states), living situations (e.g., living alone, living with pets, living with a significant other, living with children, etc.), dietary habits (e.g., alcohol consumption, caffeine consumption, omnivorous, vegetarian, vegan, sugar consumption, acid consumption, consumption of wheat, egg, soy, treenut, peanut, shellfish, and/or other suitable food items, etc.), behavioral tendencies (e.g., levels of physical activity, drug use, alcohol use, habit development, etc.), different levels of mobility (e.g., amount of exercise such as low, moderate, and/or extreme physical exercise activity; related to distance traveled within a given time period; indicated by mobility sensors such as motion and/or location sensors; etc.), different levels of sexual activity (e.g., related to numbers of partners and sexual orientation), and any other suitable behavioral information. Survey-derived data can include quantitative data and/or qualitative data that can be converted to quantitative data (e.g., using scales of severity, mapping of qualitative responses to quantified scores, etc.).

In facilitating reception of survey-derived data, Block S130 can include providing one or more surveys to a subject of the population of subjects, or to an entity associated with a subject of the population of subjects. Surveys can be provided in person (e.g., in coordination with sample provision and reception from a subject), electronically (e.g., during account setup by a subject, at an application executing at an electronic device of a subject, at a web application accessible through an internet connection, etc.), and/or in any other suitable manner.

Additionally or alternatively, portions of the supplementary dataset can be derived from sensors associated with the subject(s) (e.g., sensors of wearable computing devices, sensors of mobile devices, biometric sensors associated with the user, etc.). As such, Block S130 can include receiving one or more of: physical activity- or physical action-related data (e.g., accelerometer and gyroscope data from a mobile device or wearable electronic device of a subject), environmental data (e.g., temperature data, elevation data, climate data, light parameter data, etc.), patient nutrition or diet-related data (e.g., data from food establishment check-ins, data from spectrophotometric analysis, user-inputted data, nutrition data associated with probiotic and/or prebiotic food items, types of food consumed, amount of food consumed, diets, etc.), biometric data (e.g., data recorded through sensors within the patient's mobile computing device, data recorded through a wearable or other peripheral device in communication with the patient's mobile computing device), location data (e.g., using GPS elements), and any other suitable data. In variations, sensor data can include data sampled at one or more: optical sensors (e.g., image sensors, light sensors, etc.), audio sensors, temperature sensors, volatile compound sensors, weight sensors, humidity sensors, depth sensors, location sensors (GPS receivers; etc.), inertial sensors (e.g., accelerators, gyroscope, magnetometer, etc.), biometric sensors (e.g., heart rate sensors, fingerprint sensors, bio-impedance sensors, etc.), pressure sensors, flow sensors, power sensors (e.g., Hall effect sensors), and/or or any other suitable sensor.

Additionally or alternatively, portions of the supplementary dataset can be derived from medical record data and/or clinical data of the subject(s). As such, portions of the supplementary dataset can be derived from one or more electronic health records (EHRs) of the subject(s).

Additionally or alternatively, the supplementary dataset of Block S120 can include any other suitable diagnostic information (e.g., clinical diagnosis information), which can be combined with analyses derived from features to support characterization of subjects in subsequent blocks of the method 100. For instance, information derived from a colonoscopy, biopsy, blood test, diagnostic imaging, other suitable diagnostic procedures, survey-related information, and/or any other suitable test can be used to supplement (e.g., for any suitable portions of the method 100).

Additionally or alternatively, the supplementary dataset can include therapy-related data including one or more of: therapy regimens, types of therapies, recommended therapies, therapies used by the user, therapy adherence, etc. For example, the supplementary dataset can include user adherence (e.g., medication adherence, probiotic adherence, physical exercise adherence, dietary adherence, etc.) to a recommended therapy. However, processing supplementary datasets can be performed in any suitable manner.

3.3 Performing a Characterization Process.

Block S130 recites: performing a characterization process for the one or more microorganism-related conditions, based on the supplementary dataset and/or microbiome features (e.g., a set of microbiome composition diversity features; a set of microbiome functional diversity features; etc.) extracted from the microbiome dataset. Block S130 can function to identify, extract, and/or otherwise process features and/or feature combinations that can be used to characterize subjects or groups based upon their microbiome composition features (e.g., microbiome composition diversity features, etc.), functional features (e.g., microbiome functional diversity features, etc.), and/or other suitable microbiome features (e.g., such as through the generation and application of a characterization model for determining microorganism-related characterizations, etc.). As such, the characterization process can be used as a diagnostic tool that can characterize a subject (e.g., in terms of behavioral traits, in terms of medical conditions, in terms of demographic traits, etc.) based upon their microbiome composition and/or functional features, in relation to one or more of their health condition states (e.g., microorganism-related condition states), behavioral traits, medical conditions, demographic traits, and/or any other suitable traits. Such characterization can then be used to suggest and/or provide personalized therapies by way of the therapy model of Block S140.

In performing the characterization process, Block S130 can use computational methods (e.g., statistical methods, machine learning methods, artificial intelligence methods, bioinformatics methods, etc.) to characterize a subject as exhibiting features associated with one or more microorganism-related conditions (e.g., features characteristic of a set of users with the one or more microorganism-related conditions, etc.).

In a variation, characterization can be based upon features associated with (e.g., derived from) a statistical analysis (e.g., an analysis of probability distributions) of similarities and/or differences between a first group of subjects exhibiting a target state (e.g., a microorganism-related condition state) and a second group of subjects not exhibiting the target state (e.g., a "normal" state). In implementing this variation, one or more of a Kolmogorov-Smirnov (KS) test, a permutation test, a Cramér-von Mises test, and any other statistical test (e.g., t-test, z-test, chi-squared test, test associated with distributions, etc.) can be used. In particular, one or more such statistical hypothesis tests can be used to assess a set of features having varying degrees of abundance in a first group of subjects exhibiting a target state (e.g., a sick state) and a second group of subjects not exhibiting the target state (e.g., having a normal state). In more detail, the set of features assessed can be constrained based upon percent abundance and/or any other suitable parameter pertaining to diversity in association with the first group of subjects and the second group of subjects, in order to increase or decrease confidence in the characterization. In a specific implementation of this example, a feature can be derived from a taxon of bacteria that is abundant in a certain percentage of subjects of the first group and subjects of the second group, where a relative abundance of the taxon between the first group of subjects and the second group of subjects can be determined from the KS test, with an indication of significance (e.g., in terms of p-value). Thus, an output of Block S130 can include a normalized relative abundance value (e.g., 25% greater abundance of a taxon in subjects with a microorganism-related condition vs. subjects without the microorganism-related condition; in sick subjects vs. healthy subjects) with an indication of significance (e.g., a p-value of 0.0013). Variations of feature generation can additionally or alternatively implement or be derived from functional features or metadata features (e.g., non-bacterial markers). Additionally or alternatively, any suitable microbiome features can be derived based on statistical analyses (e.g., applied to a microorganism sequence dataset and/or other suitable microbiome dataset, etc.) including any one or more of: a prediction analysis, multi hypothesis testing, a random forest test, and/or principal component analysis.

In performing the characterization process, Block S130 can additionally or alternatively transform input data from at least one of the microbiome composition diversity dataset and microbiome functional diversity dataset into feature vectors that can be tested for efficacy in predicting characterizations of the population of subjects. Data from the supplementary dataset can be used to provide indication of one or more characterizations of a set of characterizations, where the characterization process is trained with a training dataset of candidate features and candidate classifications to identify features and/or feature combinations that have high degrees (or low degrees) of predictive power in accurately predicting a classification. As such, refinement of the characterization process with the training dataset identifies feature sets (e.g., of subject features, of combinations of features) having high correlation with specific classifications of subjects.

In variations, feature vectors (and/or any suitable set of features) effective in predicting classifications of the characterization process can include features related to one or more of: microbiome diversity metrics (e.g., in relation to distribution across taxonomic groups, in relation to distribution across archaeal, bacterial, viral, and/or eukaryotic groups), presence of taxonomic groups in one's microbiome, representation of specific genetic sequences (e.g., 16S sequences) in one's microbiome, relative abundance of taxonomic groups in one's microbiome, microbiome resilience metrics (e.g., in response to a perturbation determined from the supplementary dataset), abundance of genes that encode proteins or RNAs with given functions (enzymes, transporters, proteins from the immune system, hormones, interference RNAs, etc.) and any other suitable features associated with (e.g., derived from) the microbiome diversity dataset and/or the supplementary dataset. In variations, microbiome features can be associated with (e.g., include, correspond to, typify, etc.) at least one of: presence of a microbiome feature from the microbiome features (e.g., user microbiome features, etc.), absence of the microbiome features from the microbiome features, relative abundance of different taxonomic groups associated with the microorganism-related condition; a ratio between at least two microbiome features associated with the different taxonomic groups, interactions between the different taxonomic groups, and phylogenetic distance between the different taxonomic groups. In a specific example, microbiome features can include one or more relative abundance characteristics associated with at least one of the microbiome composition diversity features (e.g., relative abundance associated with different taxa, etc.) and the microbiome functional diversity features (e.g., relative abundance of sequences corresponding to different functional features; etc.). Relative abundance characteristics and/or other suitable microbiome features (and/or other suitable data described herein) can be extracted and/or otherwise determined based on: a normalization, a feature vector derived from at least one of linear latent variable analysis and non-linear latent variable analysis, linear regression, non-linear regression, a kernel method, a feature embedding method, a machine learning method, and a statistical inference method. Additionally or alternatively, combinations of features can be used in a feature vector, where features can be grouped and/or weighted in providing a combined feature as part of a feature set. For example, one feature or feature set can include a weighted composite of the number of represented classes of bacteria in one's microbiome, presence of a specific genus of bacteria in one's microbiome, representation of a specific 16S sequence in one's microbiome, and relative abundance of a first phylum over a second phylum of bacteria. However, the feature vectors can additionally or alternatively be determined in any other suitable manner.

Figure 3:
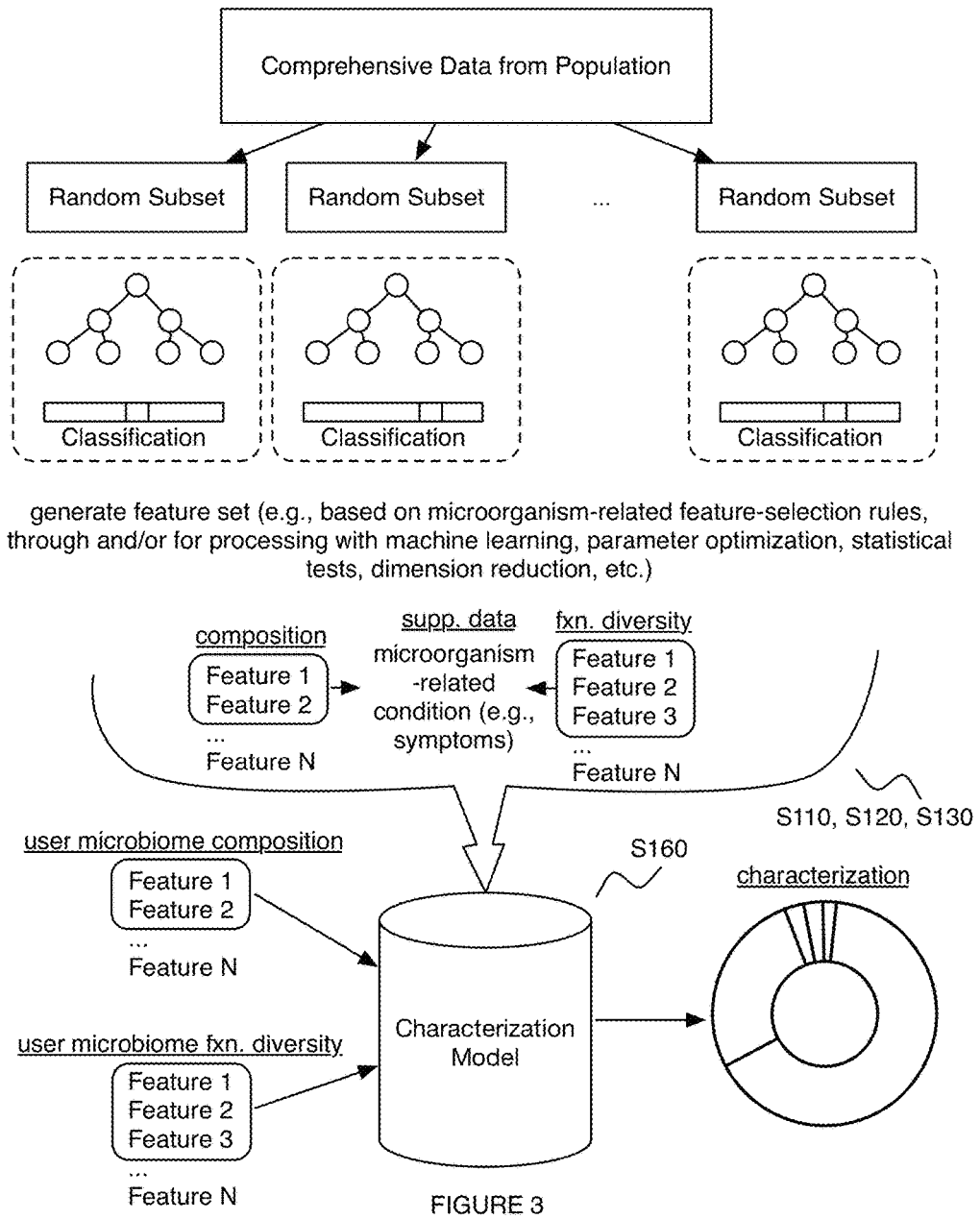
FIG. 3 depicts a variation of a process for generation of a characterization model in an embodiment of a method.

As shown in FIG. 3, in one such alternative variation of Block S130, the characterization process can be generated and trained according to a random forest predictor (RFP) algorithm that combines bagging (e.g., bootstrap aggregation) and selection of random sets of features from a training dataset to construct a set of decision trees, T, associated with the random sets of features. In using a random forest algorithm, N cases from the set of decision trees are sampled at random with replacement to create a subset of decision trees, and for each node, m prediction features are selected from all of the prediction features for assessment. The prediction feature that provides the best split at the node (e.g., according to an objective function) is used to perform the split (e.g., as a bifurcation at the node, as a trifurcation at the node). By sampling many times from a large dataset, the strength of the characterization process, in identifying features that are strong in predicting classifications can be increased substantially. In this variation, measures to prevent bias (e.g., sampling bias) and/or account for an amount of bias can be included during processing, such as to increase robustness of the model.

Additionally or alternatively, Block S130 (e.g., extracting microbiome features; generating characterization models for microorganism-related conditions; etc.) and/or other suitable portions of the method 100 (e.g., determining a microorganism-related characterization; determining and/or providing a therapy; etc.) can employ data processing approaches including any one or more of: performing pattern recognition on data (e.g., identifying correlations between microorganism-related conditions and microbiome features; etc.), fusing data from multiple sources (e.g., generating characterization models based on microbiome data and/or supplementary data from a plurality of users associated with one or more microorganism-related conditions; etc.), combination of values (e.g., averaging values, etc.), compression, conversion (e.g., digital-to-analog conversion, analog-to-digital conversion), performing statistical estimation on data (e.g. ordinary least squares regression, non-negative least squares regression, principal components analysis, ridge regression, etc.), wave modulation, normalization, updating (e.g., of characterization models and/or therapy models based on processed biological samples over time; etc.), ranking (e.g., microbiome features; therapies; etc.), weighting (e.g., microbiome features; etc.), validating, filtering (e.g., for baseline correction, data cropping, etc.), noise reduction, smoothing, filling (e.g., gap filling), aligning, model fitting, binning, windowing, clipping, transformations, mathematical operations (e.g., derivatives, moving averages, summing, subtracting, multiplying, dividing, etc.), data association, multiplexing, demultiplexing, interpolating, extrapolating, clustering, image processing techniques, other signal processing operations, other image processing operations, visualizing, and/or any other suitable processing operations. However, data processing for facilitating any suitable portions of the method 100 can be performed in any suitable manner.

In a variation, Block S130 and/or other portions of the method 100 can include applying computer-implemented rules (e.g., models, feature selection rules, etc.) to process population-level data, but can additionally or alternatively include applying computer-implemented rules to process microbiome-related data on a demographic-specific basis (e.g., subgroups sharing a demographic feature such as therapy regimens, dietary regimens, physical activity regimens, ethnicity, age, gender, weight, sleeping behaviors, etc.), condition-specific basis (e.g., subgroups exhibiting a specific microorganism-related condition, a combination of microorganism-related conditions, triggers for the microorganism-related conditions, associated symptoms, etc.), a sample type-specific basis (e.g., applying different computer-implemented rules to process microbiome data derived from different collection sites; etc.), a user basis (e.g., different computer-implemented rules for different users; etc.) and/or any other suitable basis. As such, Block S132 can include assigning users from the population of users to one or more subgroups; and applying different computer-implemented rules for determining features (e.g., the set of feature types used; the types of characterization models generated from the features; etc.) for the different subgroups. However, applying computer-implemented rules can be performed in any suitable manner.

In another variation, Block S130 can include processing (e.g., generating, training, updating, executing, storing, etc.) one or more characterization models (e.g., microorganism-related condition characterization models, etc.) for one or more microorganism-related conditions. The characterization models preferably leverage microbiome features as inputs, and preferably output microorganism-related characterizations and/or any suitable components thereof; but characterization models can use and suitable inputs to generate any suitable outputs. In an example, Block S130 can include transforming the supplementary data, the microbiome composition diversity features, and the microbiome functional diversity features into a characterization model (e.g., training a microorganism-related characterization model based on the supplementary data and microbiome features; etc.) for the microorganism-related condition. In another example, the method 100 can include: determining a population microorganism sequence dataset (e.g., including microorganism sequence outputs for different users of the population; etc.) for a population of users associated with one or more microorganism-related conditions, based on a set of samples from the population of users (e.g., and/or based on one or more primer types associated with the microorganism-related condition; etc.); collecting a supplementary dataset associated with diagnosis of the one or more microorganism-related conditions for the population of subjects; and generating the microorganism-related condition characterization model based on the population microorganism sequence dataset and the supplementary dataset.

Figure 8A:
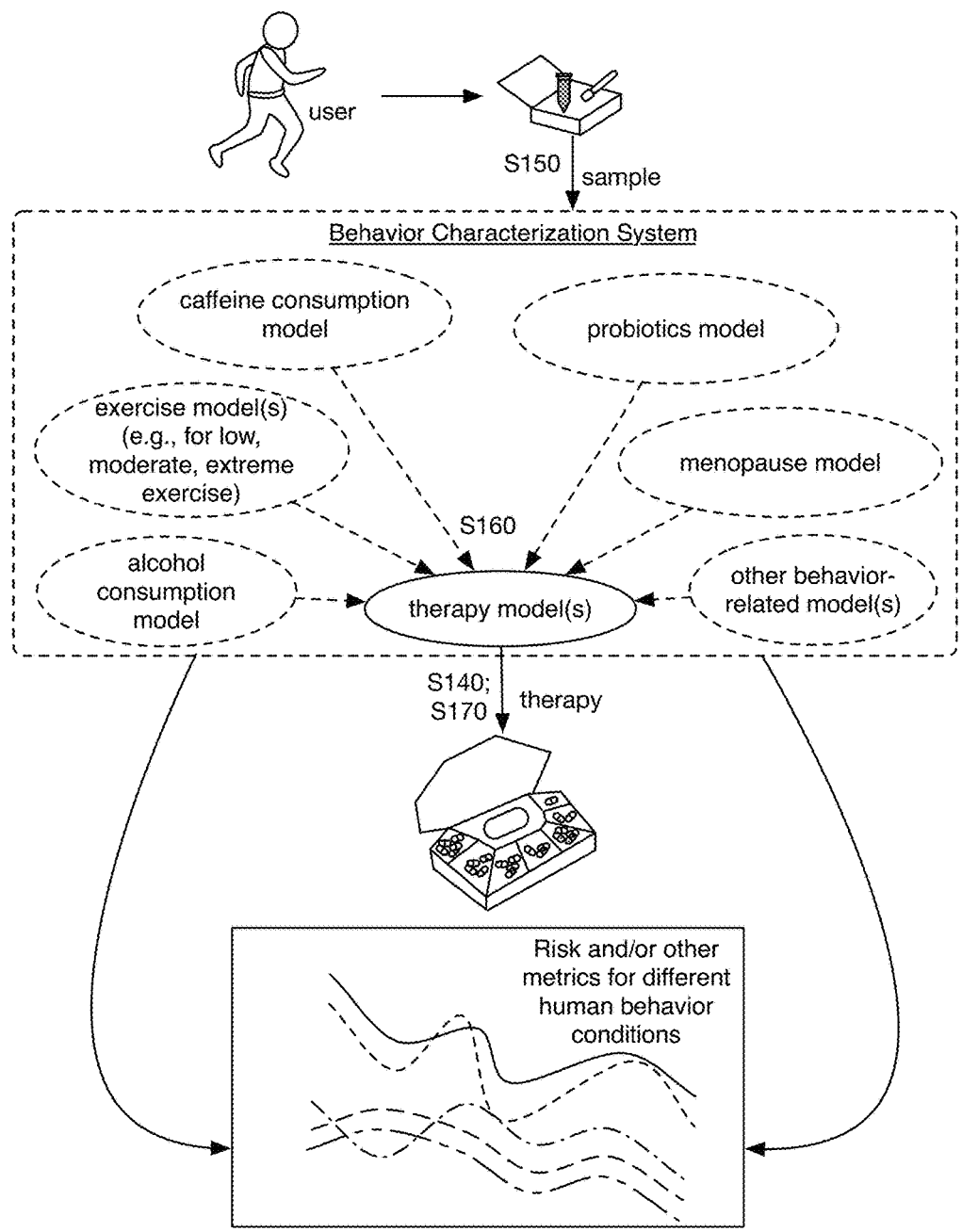
FIGS. 8A-8C depicts variations of performing characterization processes with characterization models.
Figure 8B:
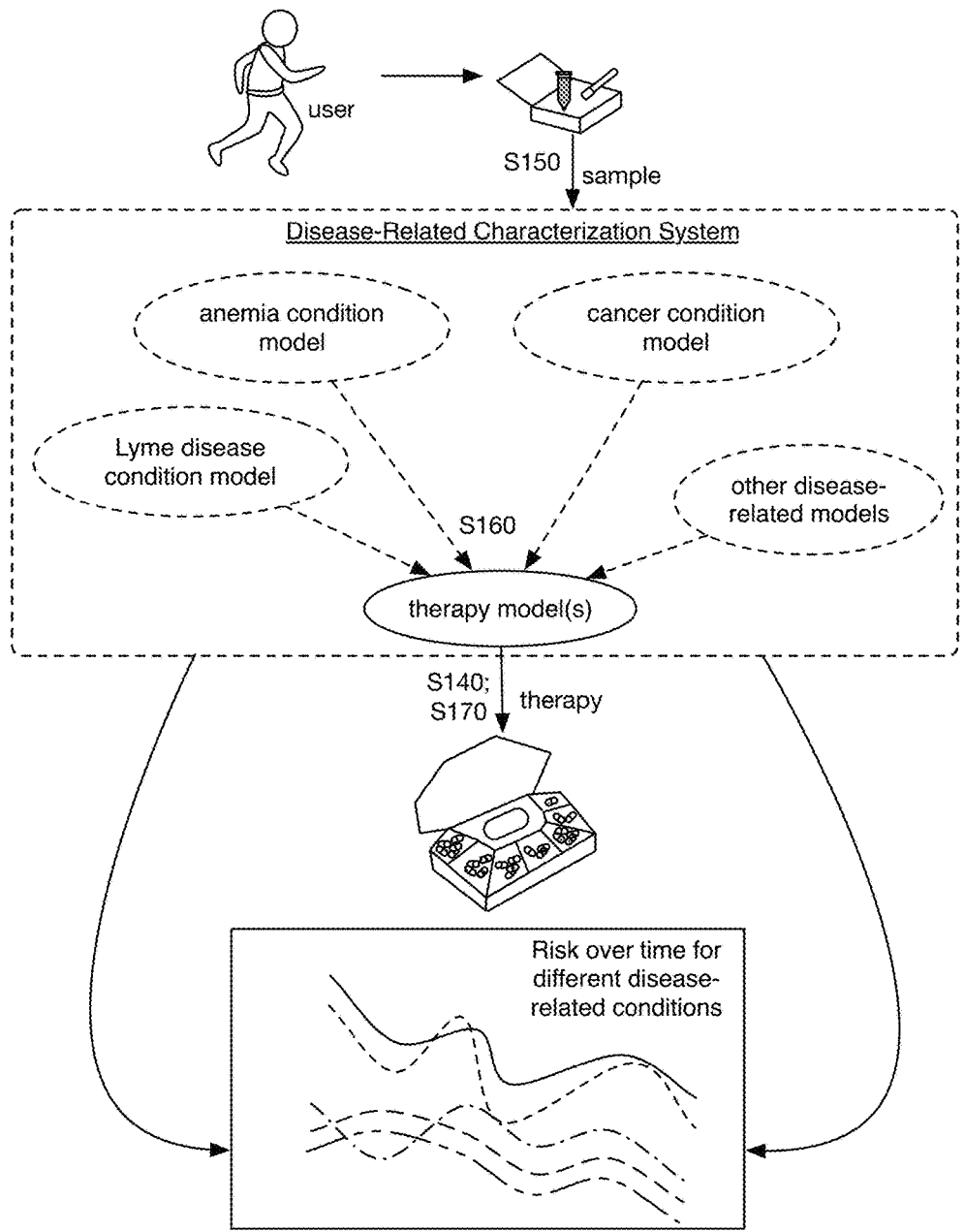
Figure 8C:
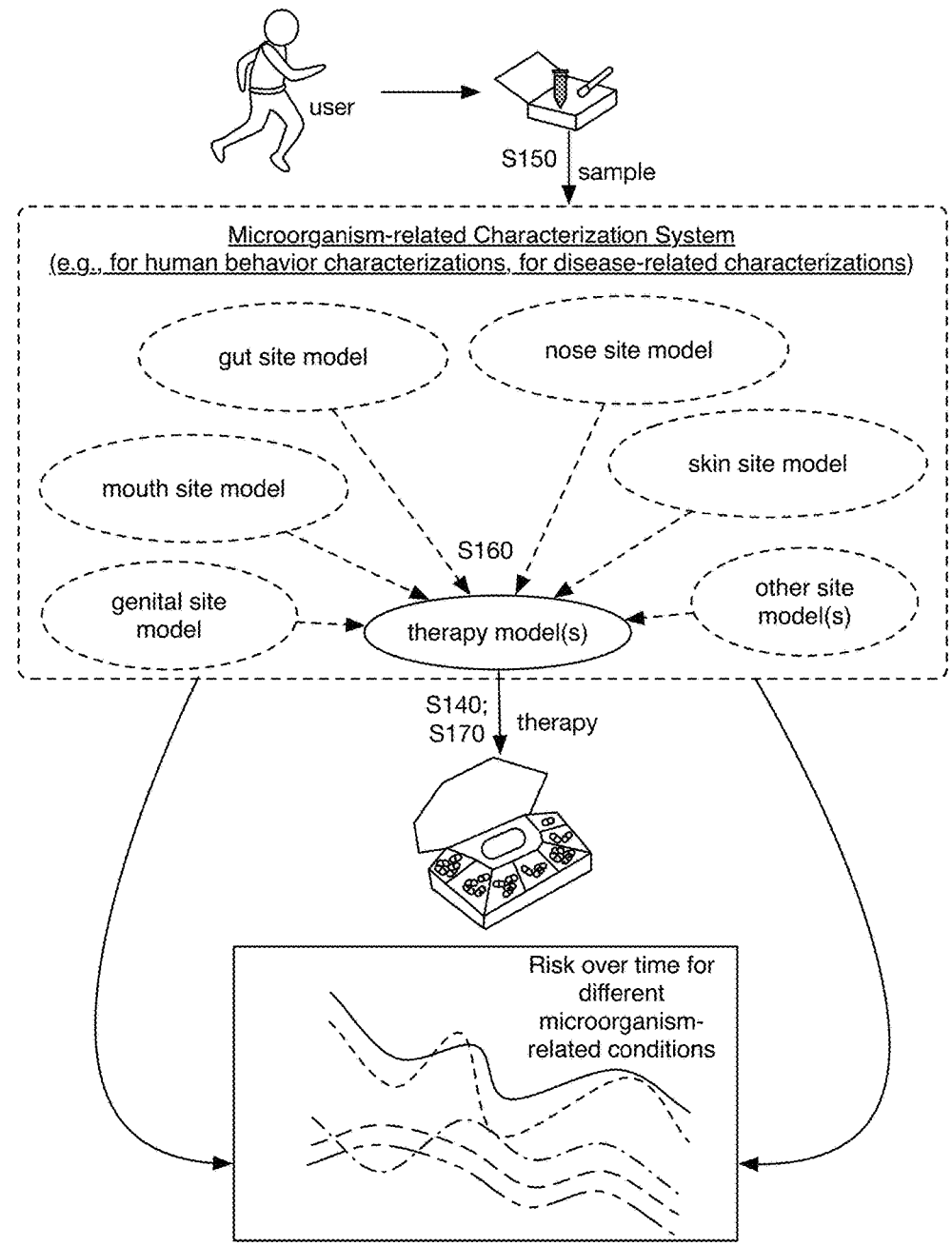

In another variation, as shown in FIGS. 8A-8C, different microorganism-related characterization (e.g., human behavior characterization, disease-related characterization, etc.) models and/or other suitable models (e.g., generated with different algorithms, with different sets of features, with different input and/or output types, applied in different manners such as in relation to time, frequency, component applying the model, etc.) can be generated for different human behavior conditions (e.g., a characterization model for a caffeine consumption condition, a characterization model for a alcohol consumption condition, a third characterization model for other dietary behaviors, a characterization model for users on a dietary regimen not including the food items, different models based on physical activity level such as low, moderate, and/or extreme physical exercise conditions; etc.), different disease-related conditions (e.g., a cancer characterization model, an anemia characterization model, a Lyme disease characterization model, etc.), other microorganism-related conditions, different user demographics (e.g., based on age, gender, weight, height, ethnicity; etc.), different physiological sites (e.g., a gut site model, a nose site model, a skin site model, a mouth site model, a genitals site model, etc.), individual users, supplementary data (e.g., models incorporating features associated with (e.g., derived from) biometric sensor data and/or survey response data vs. models independent of supplementary data, etc.), and/or other suitable criteria (and/or combination of criteria, such as a characterization model for an alcohol consumption condition in relation to a gut site, etc.).

In variations, determining microorganism-related characterizations and/or any other suitable characterizations can include determining microorganism-related characterizations in relation to specific physiological sites (e.g., gut, healthy gut, skin, nose, mouth, genitals, other suitable physiological sites, other sample collection sites, etc.), such as through any one or more of: determining a microorganism-related characterization based on a characterization model derived based on site-specific data (e.g., defining correlations between a microorganism-related condition and microbiome features associated with one or more physiological sites); determining a microorganism-related characterization based on a user biological sample collected at one or more physiological sites, and/or any other suitable site-related processes. In examples, machine learning approaches (e.g., classifiers, deep learning algorithms), parameter optimization approaches (e.g., Bayesian Parameter Optimization), validation approaches (e.g., cross validation approaches), statistical tests (e.g., univariate statistical techniques, multivariate statistical techniques, correlation analysis such as canonical correlation analysis, etc.), dimension reduction approaches, and/or other suitable approaches (e.g., described herein) can be applied in determining site-related (e.g., physiological site-related, etc.) characterizations (e.g., using a one or more approaches for one or more sample collection sites, such as for each type of sample collection site, etc.), other suitable characterizations, therapies, and/or any other suitable outputs. In a specific example, performing a characterization process (e.g., determining a microorganism-related characterization; determining microbiome features; based on a microorganism-related characterization model; etc.) can include applying at least one of: machine learning approaches, parameter optimization approaches, statistical tests, dimension reduction approaches, and/or other suitable approaches (e.g., where microbiome features such as a set of microbiome composition diversity features and/or a set of microbiome functional diversity features can be associated with microorganisms collected at least at one of a gut site, a skin site, a nose site, a mouth site, a genitals site, etc.). In another specific example, characterization processes performed for a plurality of sample collection sites can be used to generate individual characterizations that can be combined to determine an aggregate characterization (e.g., an aggregate microbiome score, such as for one or more conditions described herein, etc.). However, the method 100 can include determining any suitable site-related (e.g., site-specific) outputs, and/or performing any suitable portions of the method 100 (e.g., collecting samples, processing samples, determining therapies) with site-specificity and/or other site-relatedness in any suitable manner.

Characterization of the subject(s) can additionally or alternatively implement use of a high false positive test and/or a high false negative test to further analyze sensitivity of the characterization process in supporting analyses generated according to embodiments of the method 100. However, performing a characterization process S130 can be performed in any suitable manner.

3.3.A Caffeine Consumption Characterization Process.

In a variation, Block S130 can include performing a caffeine consumption characterization process (e.g., determining and/or applying a caffeine consumption characterization model; etc.) for one or more users.

In one implementation, a characterization process of Block S130 based upon statistical analyses can identify the sets of features that have the highest correlations with caffeine consumption associated-microorganisms for which one or more therapies would have a positive effect, such as based upon a random forest predictor algorithm (and/or other suitable model) trained with a training dataset derived from a subset of the population of subjects, and/or validated with a validation dataset derived from a subset of the population of subjects. In particular, a caffeine consumption condition can include a lifestyle human behavior related to food habits, including consuming coffee and/or any other substance, liquid or food that contain caffeine as part of principal ingredients or its composition, characterized by the ingest or consuming regularly (e.g., daily, one or more times a day, etc.) at least one of different sources of caffeine (e.g., coffee, tea, chocolate, etc.) within the diet. A set of features (e.g., useful for diagnostics and/or other suitable purposes, etc.) associated with a caffeine consumption condition can include features associated with (e.g., derived from) one or more of the following taxons: *Collinsella aerofaciens* (Species), *Blautia luti* (Species), *Erysipelatoclostridium ramosum* (Species), *Haemophilus parainfluenzae* (Species), *Subdoligranulum variabile* (Species), *Parabacteroides merdae* (Species), *Alistipes putredinis* (Species), *Bacteroides vulgatus* (Species), *Bacteroides fragilis* (Species), *Faecalibacterium prausnitzii* (Species), *Bacteroides thetaiotaomicron* (Species), *Dorea formicigenerans* (Species), *Blautia faecis* (Species), *Bacteroides acidifaciens* (Species), *Flavonifractor plautii* (Species), *Methanobrevibacter smithii* (Species), *Collinsella* (Genus), *Dorea* (Genus), *Haemophilus* (Genus), *Bacteroides* (Genus), *Subdoligranulum* (Genus), *Oscillospira* (Genus), *Clostridium* (Genus), *Faecalibacterium* (Genus), *Veillonella* (Genus), *Roseburia* (Genus), *Eggerthella* (Genus), *Anaerotruncus* (Genus), *Butyricimonas* (Genus), *Finegoldia* (Genus), *Sarcina* (Genus), *Phascolarctobacterium* (Genus), *Enterobacter* (Genus), *Methanobrevibacter* (Genus), *Catenibacterium* (Genus), *Kluyvera* (Genus), *Moryella* (Genus), Coriobacteriaceae (Family), Bacteroidaceae (Family), Ruminococcaceae (Family), Erysipelotrichaceae (Family), Sutterellaceae (Family), Coriobacteriales (Order), Clostridiales (Order), Bacteroidales (Order), Actinomycetales (Order), Erysipelotrichales (Order), Puniceicoccales (Order), Burkholderiales (Order), Actinobacteria (Class), Clostridia (Class), Gammaproteobacteria (Class), Flavobacteriia (Class), Bacteroidia (Class), Deltaproteobacteria (Class), Betaproteobacteria (Class), Methanobacteria (Class), Erysipelotrichia (Class), Negativicutes (Class), Actinobacteria (Phylum), Firmicutes (Phylum), Bacteroidetes (Phylum) and Proteobacteria (Phylum), and/or the microbiome features can additionally or alternatively include functional features (e.g., functional diversity features, etc.) including at least one or more of the followings: Metabolism (KEGG2), Transport and Catabolism (KEGG2), Environmental Adaptation (KEGG2), Glycan Biosynthesis and Metabolism (KEGG2), Signaling Molecules and Interaction (KEGG2), Cellular Processes and Signaling (KEGG2), Translation (KEGG2), Metabolism of Other Amino Acids (KEGG2), Poorly Characterized (KEGG2), Carbohydrate Metabolism (KEGG2), Cell Motility (KEGG2), Transcription (KEGG2), Genetic Information Processing (KEGG2), Membrane Transport (KEGG2), Infectious Diseases (KEGG2), Lipid Metabolism (KEGG2), Replication and Repair (KEGG2), Nervous System (KEGG2), Energy Metabolism (KEGG2), Enzyme Families (KEGG2), Nucleotide Metabolism (KEGG2), Nitrogen metabolism (KEGG3), Ribosome Biogenesis (KEGG3), Pores ion channels (KEGG3), Membrane and intracellular structural molecules (KEGG3), Phenylalanine metabolism (KEGG3), Ascorbate and aldarate metabolism (KEGG3), Plant-pathogen interaction (KEGG3), Lysosome (KEGG3), Glycosaminoglycan degradation (KEGG3), Aminoacyl-tRNA biosynthesis (KEGG3), Lipopolysaccharide biosynthesis proteins (KEGG3), Geraniol degradation (KEGG3), Translation proteins (KEGG3), Other glycan degradation (KEGG3), Citrate cycle (TCA cycle) (KEGG3), Other ion-coupled transporters (KEGG3), Biosynthesis and biodegradation of secondary metabolites (KEGG3), Carbon fixation pathways in prokaryotes (KEGG3), Peptidoglycan biosynthesis (KEGG3), Glutathione metabolism (KEGG3), Toluene degradation (KEGG3), Cell motility and secretion (KEGG3), Glycerophospholipid metabolism (KEGG3), Inorganic ion transport and metabolism (KEGG3), Thiamine metabolism (KEGG3), Energy metabolism (KEGG3), Glycosphingolipid biosynthesis—ganglio series (KEGG3), RNA polymerase (KEGG3), Polycyclic aromatic hydrocarbon degradation (KEGG3), Cytoskeleton proteins (KEGG3), Inositol phosphate metabolism (KEGG3), Cellular antigens (KEGG3), Glycosphingolipid biosynthesis—globo series (KEGG3), Penicillin and cephalosporin biosynthesis (KEGG3), Ubiquinone and other terpenoid-quinone biosynthesis (KEGG3), Peroxisome (KEGG3), Pantothenate and CoA biosynthesis (KEGG3), Base excision repair (KEGG3), Others (KEGG3), Terpenoid backbone biosynthesis (KEGG3), Ribosome biogenesis in eukaryotes (KEGG3), Type II diabetes mellitus (KEGG3), Amino acid metabolism (KEGG3), Oxidative phosphorylation (KEGG3), Bacterial chemotaxis (KEGG3), Lysine biosynthesis (KEGG3), Pentose and glucuronate interconversions (KEGG3), Signal transduction mechanisms (KEGG3), Chromosome (KEGG3), Sporulation (KEGG3), Sulfur metabolism (KEGG3), Ribosome (KEGG3), Phenylalanine, tyrosine and tryptophan biosynthesis (KEGG3), Amino acid related enzymes (KEGG3), Sphingolipid metabolism (KEGG3), Valine, leucine and isoleucine degradation (KEGG3), Function unknown (KEGG3), D-Alanine metabolism (KEGG3), Glycosyltransferases (KEGG3), Transcription factors (KEGG3), Taurine and hypotaurine metabolism (KEGG3), Glyoxylate and dicarboxylate metabolism (KEGG3), Transporters (KEGG3), Other transporters (KEGG3), Aminobenzoate degradation (KEGG3), Butirosin and neomycin biosynthesis (KEGG3), Carbohydrate metabolism (KEGG3), Translation factors (KEGG3), ABC transporters (KEGG3), Replication, recombination and repair proteins (KEGG3), Bacterial toxins (KEGG3), Nucleotide excision repair (KEGG3), Cell division (KEGG3), Nicotinate and nicotinamide metabolism (KEGG3), Amino sugar and nucleotide sugar metabolism (KEGG3), Glycerolipid metabolism (KEGG3), Biosynthesis of vancomycin group antibiotics (KEGG3), Type I diabetes mellitus (KEGG3), DNA repair and recombination proteins (KEGG3), Lipid metabolism (KEGG3), Retinol metabolism (KEGG3), Glutamatergic synapse (KEGG3), Primary immunodeficiency (KEGG3), Photosynthesis (KEGG3), Ethylbenzene degradation (KEGG3), Cysteine and methionine metabolism (KEGG3), Methane metabolism (KEGG3), Photosynthesis proteins (KEGG3), Lysine degradation (KEGG3), Biotin metabolism (KEGG3), Tuberculosis (KEGG3), Cell cycle—*Caulobacter* (KEGG3), Fructose and mannose metabolism (KEGG3), Galactose metabolism (KEGG3), Benzoate degradation (KEGG3), beta-Alanine metabolism (KEGG3), Protein folding and associated processing (KEGG3), Pyrimidine metabolism (KEGG3), Valine, leucine and isoleucine biosynthesis (KEGG3), Homologous recombination (KEGG3), Starch and sucrose metabolism (KEGG3), Limonene and pinene degradation (KEGG3), Protein export (KEGG3), Chaperones and folding catalysts (KEGG3), Folate biosynthesis (KEGG3).

Additionally or alternatively, microbiome features (e.g., microbiome composition diversity features) can include and/or otherwise be associated with (e.g., relative abundance for the taxons, etc.) one or more of the following taxons, such as in relation to a sample site (e.g., caffeine consumption condition correlations with microorganisms observed at a particular sample site): Actinobacteria (phylum; e.g., gut site), Euryarchaeota (phylum; e.g., gut site), Synergistetes (phylum; e.g., gut site), Actinobacteria (class; e.g., gut site), Deltaproteobacteria (class; e.g., gut site), Deltaproteobacteria (class; e.g., gut site), Gammaproteobacteria (class; e.g., gut site), Methanobacteria (class; e.g., gut site), Synergistia (class; e.g., gut site), Bacillales (order; e.g., gut site), Coriobacteriales (order; e.g., gut site), Desulfovibrionales (order; e.g., gut site), Desulfovibrionales (order; e.g., gut site), Methanobacteriales (order; e.g., gut site), Synergistales (order; e.g., gut site), Bacteroidaceae (family; e.g., gut site), Coriobacteriaceae (family; e.g., gut site), Desulfovibrionaceae (family; e.g., gut site), Desulfovibrionaceae (family; e.g., gut site), Methanobacteriaceae (family; e.g., gut site), Prevotellaceae (family; e.g., gut site), Staphylococcaceae (family; e.g., gut site), Synergistaceae (family; e.g., gut site), *Acidaminococcus* (genus; e.g., gut site), *Allisonella* (genus; e.g., gut site), *Bacteroides* (genus; e.g., gut site), *Butyricimonas* (genus; e.g., gut site), *Catenibacterium* (genus; e.g., gut site), *Cloacibacillus* (genus; e.g., gut site), *Collinsella* (genus; e.g., gut site), *Desulfovibrio* (genus; e.g., gut site), *Dorea* (genus; e.g., gut site), *Enterobacter* (genus; e.g., gut site), *Enterorhabdus* (genus; e.g., gut site), *Howardella* (genus; e.g., gut site), *Lachnospira* (genus; e.g., gut site), *Methanobrevibacter* (genus; e.g., gut site), *Oscillospira* (genus; e.g., gut site), *Parvimonas* (genus; e.g., gut site), *Peptococcus* (genus; e.g., gut site), *Selenomonas* (genus; e.g., mouth site), *Staphylococcus* (genus; e.g., gut site), *Allisonella histaminiformans* (species; e.g., gut site), *Bacteroides coprocola* (species; e.g., gut site), *Bacteroides massil-*

*iensis* (species; e.g., gut site), *Bacteroides vulgatus* (species; e.g., gut site), *Butyricimonas* sp. JCM 18677 (species; e.g., gut site), *Butyricimonas virosa* (species; e.g., gut site), *Butyricimonas virosa* (species; e.g., gut site), *Catenibacterium mitsuokai* (species; e.g., gut site), *Cloacibacillus evryensis* (species; e.g., gut site), *Collinsella aerofaciens* (species; e.g., gut site), *Desulfovibrio piger* (species; e.g., gut site), *Dialister invisus* (species; e.g., gut site), *Dorea longicatena* (species; e.g., gut site), *Fusicatenibacter saccharivorans* (species; e.g., gut site), *Fusobacterium periodonticum* (species; e.g., gut site), *Fusobacterium* sp. CM21 (species; e.g., mouth site), *Fusobacterium* sp. CM22 (species; e.g., gut site), *Howardella ureilytica* (species; e.g., gut site), *Methanobrevibacter smithii* (species; e.g., gut site), *Parabacteroides merdae* (species; e.g., gut site), *Parvimonas micra* (species; e.g., gut site), *Peptostreptococcus stomatis* (species; e.g., gut site), *Prevotella* sp. WAL 2039G (species; e.g., mouth site), *Rothia dentocariosa* (species; e.g., mouth site), *Staphylococcus* sp. C912 (species; e.g., gut site), *Veillonella* sp. MSA12 (species; e.g., gut site).

3.3.B Cancer Condition Characterization Process.

In a variation, Block S130 can include performing a cancer condition characterization process (e.g., determining and/or applying a cancer characterization model; etc.) for one or more users.

In one implementation, a characterization process of Block S130 based upon statistical analyses can identify the sets of features that have the highest correlations with any type of cancer condition associated with microorganisms for which one or more therapies would have a positive effect, such as based upon a random forest predictor algorithm (and/or other suitable model) trained with a training dataset derived from a subset of the population of subjects, and/or validated with a validation dataset derived from a subset of the population of subjects. In particular, a cancer condition can be a generic name given to a collection of related diseases that can affect any the cells in the body of a multicellular organisms, including human and characterized by out-of-control cell growth; where diagnosis can include: medical history, blood test samples, imaging exams, cell culture, and/or other suitable procedures. A set of features (e.g., useful for diagnostics and/or other suitatble purposes, etc.) associated with a cancer condition can include features associated with (e.g., derived from) one or more of the following taxons: *Blautia luti* (Species), *Collinsella aerofaciens* (Species), *Flavonifractor plautii* (Species), *Subdoligranulum variabile* (Species), *Faecalibacterium prausnitzii* (Species), *Dorea formicigenerans* (Species), *Roseburia inulinivorans* (Species), *Blautia* sp. YHC-4 (Species), *Parasutterella excrementihominis* (Species), *Sutterella wadsworthensis* (Species), *Bacteroides caccae* (Species), *Moryella* (Genus), *Collinsella* (Genus), *Subdoligranulum* (Genus), *Dorea* (Genus), *Terrisporobacter* (Genus), *Parabacteroides* (Genus), *Bifidobacterium* (Genus), *Faecalibacterium* (Genus), *Bacteroides* (Genus), *Lachnospira* (Genus), *Pseudobutyrivibrio* (Genus), *Erysipelatoclostridium* (Genus), Coriobacteriaceae (Family), Porphyromonadaceae (Family), Bifidobacteriaceae (Family), Ruminococcaceae (Family), Bacteroidaceae (Family), Oscillospiraceae (Family), Sutterellaceae (Family), Flavobacteriaceae (Family), Coriobacteriales (Order), Bacteroidales (Order), Clostridiales (Order), Bifidobacteriales (Order), Burkholderiales (Order), Flavobacteriales (Order), Actinobacteria (Class), Bacteroidia (Class), Clostridia (Class), Betaproteobacteria (Class), Flavobacteriia (Class), Actinobacteria (Phylum), Bacteroidetes (Phylum), Firmicutes (Phylum), and/or functional features including at least one or a combination of the followings: Metabolism (KEGG2), Transport and Catabolism (KEGG2), Glycan Biosynthesis and Metabolism (KEGG2), Lipid Metabolism (KEGG2), Carbohydrate Metabolism (KEGG2), Biosynthesis of Other Secondary Metabolites (KEGG2), Poorly Characterized (KEGG2), Cellular Processes and Signaling (KEGG2), Environmental Adaptation (KEGG2), Translation (KEGG2), Replication and Repair (KEGG2), Signaling Molecules and Interaction (KEGG2), Phosphatidylinositol signaling system (KEGG3), Ion channels (KEGG3), Lipoic acid metabolism (KEGG3), Phosphonate and phosphinate metabolism (KEGG3), Glycosaminoglycan degradation (KEGG3), Inorganic ion transport and metabolism (KEGG3), Lysosome (KEGG3), Lipopolysaccharide biosynthesis proteins (KEGG3), Membrane and intracellular structural molecules (KEGG3), Ribosome Biogenesis (KEGG3), Plant-pathogen interaction (KEGG3), Huntington's disease (KEGG3), Penicillin and cephalosporin biosynthesis (KEGG3), Ascorbate and aldarate metabolism (KEGG3), Cell motility and secretion (KEGG3), Pores ion channels (KEGG3), Function unknown (KEGG3), Sphingolipid metabolism (KEGG3), Pentose and glucuronate interconversions (KEGG3), Others (KEGG3), Other glycan degradation (KEGG3), Glycosphingolipid biosynthesis—globo series (KEGG3), Glycosphingolipid biosynthesis—ganglio series (KEGG3), Chromosome (KEGG3), Inositol phosphate metabolism (KEGG3), Biotin metabolism (KEGG3), Sulfur metabolism (KEGG3), Amino acid metabolism (KEGG3), Biosynthesis and biodegradation of secondary metabolites (KEGG3), Phenylalanine metabolism (KEGG3), Carbohydrate metabolism (KEGG3), D-Alanine metabolism (KEGG3), Glyoxylate and dicarboxylate metabolism (KEGG3), Streptomycin biosynthesis (KEGG3), RNA polymerase (KEGG3), Amino acid related enzymes (KEGG3), Glycosyltransferases (KEGG3), MAPK signaling pathway—yeast (KEGG3), Peptidoglycan biosynthesis (KEGG3), Terpenoid backbone biosynthesis (KEGG3), Amino sugar and nucleotide sugar metabolism (KEGG3), Other transporters (KEGG3), Geraniol degradation (KEGG3), Vitamin metabolism (KEGG3), Taurine and hypotaurine metabolism (KEGG3), Pyrimidine metabolism (KEGG3), Thiamine metabolism (KEGG3), Ribosome (KEGG3), Homologous recombination (KEGG3) and Translation proteins (KEGG3).

Additionally or alternatively, microbiome features (e.g., microbiome composition diversity features) can include and/or otherwise be associated with (e.g., relative abundance for the taxons, etc.) one or more of the following taxons, such as in relation to a sample site (e.g., cancer condition correlations with microorganisms observed at a particular sample site): Actinobacteria (phylum; e.g., nose site), Firmicutes (phylum; e.g., nose site), Actinobacteria (class; e.g., nose site), Alphaproteobacteria (class; e.g., gut site), Bacilli (class; e.g., nose site), Actinomycetales (order; e.g., nose site), Bacillales (order; e.g., nose site), Rhodospirillales (order; e.g., gut site), Acidaminococcaceae (family; e.g., gut site), Corynebacteriaceae (family; e.g., nose site), Oscillospiraceae (family; e.g., gut site), Ruminococcaceae (family; e.g., gut site), Staphylococcaceae (family; e.g., nose site), *Acidaminococcus* (genus; e.g., gut site), *Bilophila* (genus; e.g., gut site), *Corynebacterium* (genus; e.g., nose site), *Flavonifractor* (genus; e.g., gut site), *Intestinibacter* (genus; e.g., gut site), *Intestinimonas* (genus; e.g., gut site), *Lactonifactor* (genus; e.g., gut site), *Staphylococcus* (genus; e.g., nose site), *Streptococcus* (genus; e.g., nose site), *Bacte-*

*roides* sp. AR20 (species; e.g., gut site), *Bilophila* sp. 4_1_30 (species; e.g., gut site), *Blautia* sp. YHC-4 (species; e.g., gut site).

3.3.C Anemia Condition Characterization Process.

In a variation, Block S130 can include performing an anemia condition characterization process (e.g., determining and/or applying an anemia characterization model; etc.) for one or more users.

In one implementation, a characterization process of Block S130 based upon statistical analyses can identify the sets of features that have the highest correlations with anemia for which one or more therapies would have a positive effect, such as based upon a random forest predictor algorithm (and/or other suitable model) trained with a training dataset derived from a subset of the population of subjects, and/or validated with a validation dataset derived from a subset of the population of subjects. In particular, anemia can include health condition associated with low count of red cells within the blood, with multiple possible causes characterized by blood sample test (e.g., red cells count, hemoglobin level, etc.). A set of features (e.g., useful for diagnostics and/or other purposes) associated with an anemia condition can include features associated with (e.g., derived from) one or more of the following taxons: *Flavonifractor plautii* (Species), *Blautia luti* (Species), *Collinsella aerofaciens* (Species), *Subdoligranulum variabile* (Species), *Dorea formicigenerans* (Species), *Blautia* sp. YHC-4 (Species), *Faecalibacterium prausnitzii* (Species), *Roseburia inulinivorans* (Species), *Subdoligranulum* (Genus), *Terrisporobacter* (Genus), *Dorea* (Genus), *Collinsella* (Genus), *Sarcina* (Genus), *Clostridium* (Genus), *Marvinbryantia* (Genus), *Moryella* (Genus), *Lactobacillus* (Genus), *Bacteroides* (Genus), *Eggerthella* (Genus), *Kluyvera* (Genus), *Faecalibacterium* (Genus), *Thalassospira* (Genus), Lactobacillaceae (Family), Coriobacteriaceae (Family), Clostridiaceae (Family), Ruminococcaceae (Family), Bacteroidaceae (Family), Flavobacteriaceae (Family), Oscillospiraceae (Family), Rhodospirillaceae (Family), Enterobacteriaceae (Family), Porphyromonadaceae (Family), Coriobacteriales (Order), Bacteroidales (Order), Flavobacteriales (Order), Clostridiales (Order), Rhodospirillales (Order), Enterobacteriales (Order), Selenomonadales (Order), Actinobacteria (Class), Bacteroidia (Class), Clostridia (Class), Flavobacteriia (Class), Alphaproteobacteria (Class), Negativicutes (Class), Actinobacteria (Phylum), Bacteroidetes (Phylum), Firmicutes (Phylum), and/or the microbiome features can additionally or alternatively include functional features (e.g., functional diversity features, etc.) including at least one or a combination of the followings: Metabolism (KEGG2), Translation (KEGG2), Carbohydrate Metabolism (KEGG2), Replication and Repair (KEGG2), Cellular Processes and Signaling (KEGG2), Signaling Molecules and Interaction (KEGG2), Nucleotide Metabolism (KEGG2), Poorly Characterized (KEGG2), Glycan Biosynthesis and Metabolism (KEGG2), Metabolism of Other Amino Acids (KEGG2), Environmental Adaptation (KEGG2), Cell Growth and Death (KEGG2), Biosynthesis of Other Secondary Metabolites (KEGG2), Transport and Catabolism (KEGG2), Lipid Metabolism (KEGG2), Signal Transduction (KEGG2), Ribosome Biogenesis (KEGG3), Amino acid metabolism (KEGG3), Ion channels (KEGG3), Pentose and glucuronate interconversions (KEGG3), Ribosome biogenesis in eukaryotes (KEGG3), Others (KEGG3), Inorganic ion transport and metabolism (KEGG3), Amino acid related enzymes (KEGG3), Ascorbate and aldarate metabolism (KEGG3), Peptidoglycan biosynthesis (KEGG3), Aminoacyl-tRNA biosynthesis (KEGG3), Translation proteins (KEGG3), Ribosome (KEGG3), Chromosome (KEGG3), MAPK signaling pathway—yeast (KEGG3), Terpenoid backbone biosynthesis (KEGG3), RNA polymerase (KEGG3), Nicotinate and nicotinamide metabolism (KEGG3), Penicillin and cephalosporin biosynthesis (KEGG3), Homologous recombination (KEGG3), Lipoic acid metabolism (KEGG3), DNA repair and recombination proteins (KEGG3), Biosynthesis and biodegradation of secondary metabolites (KEGG3), Translation factors (KEGG3), Glyoxylate and dicarboxylate metabolism (KEGG3), Phosphatidylinositol signaling system (KEGG3), Pyrimidine metabolism (KEGG3), Other ion-coupled transporters (KEGG3), Taurine and hypotaurine metabolism (KEGG3), Cell motility and secretion (KEGG3), Carbohydrate metabolism (KEGG3), Function unknown (KEGG3), D-Alanine metabolism (KEGG3), Fructose and mannose metabolism (KEGG3), Plant-pathogen interaction (KEGG3), Vitamin metabolism (KEGG3), Phosphonate and phosphinate metabolism (KEGG3), Lipopolysaccharide biosynthesis proteins (KEGG3), Amino sugar and nucleotide sugar metabolism (KEGG3), Galactose metabolism (KEGG3), Other transporters (KEGG3), Membrane and intracellular structural molecules (KEGG3), Nucleotide excision repair (KEGG3), Pores ion channels (KEGG3), Sphingolipid metabolism (KEGG3), Protein export (KEGG3), Cell cycle—*Caulobacter* (KEGG3), Bisphenol degradation (KEGG3), Cysteine and methionine metabolism (KEGG3), Mismatch repair (KEGG3), Huntington's disease (KEGG3), Bacterial toxins (KEGG3), Nitrogen metabolism (KEGG3), Other glycan degradation (KEGG3), Lysosome (KEGG3), Phenylalanine metabolism (KEGG3), Cyanoamino acid metabolism (KEGG3), Glycosaminoglycan degradation (KEGG3), Nucleotide metabolism (KEGG3), Glycosphingolipid biosynthesis—globo series (KEGG3) and Pantothenate and CoA biosynthesis (KE-G3).

Additionally or alternatively, microbiome features (e.g., microbiome composition diversity features) can include and/or otherwise be associated with (e.g., relative abundance for the taxons, etc.) one or more of the following taxons, such as in relation to a sample site (e.g., anemia condition correlations with microorganisms observed at a particular sample site): Acidaminococcaceae (family; e.g., gut site), *Odoribacter* (genus; e.g., gut site), *Phascolarctobacterium* (genus; e.g., gut site), *Flavonifractor plautii* (species; e.g., gut site).

3.3.D Alcohol Consumption Characterization Process.

In a variation, Block S130 can include performing an alcohol consumption characterization process (e.g., determining and/or applying a alcohol consumption characterization model; etc.) for one or more users.

In one implementation, a characterization process of Block S130 based upon statistical analyses can identify the sets of features that have the highest correlations with alcohol consumption associated-microorganisms for which one or more therapies would have a positive effect, such as based upon a random forest predictor algorithm (and/or other suitable model) trained with a training dataset derived from a subset of the population of subjects, and/or validated with a validation dataset derived from a subset of the population of subjects. In particular, an alcohol consumption condition can include a lifestyle human behavior related to food habits and diet, including drinking alcohol or any other substance, specially liquid or food that contain alcohol as principal ingredients or its composition, characterized by the ingest or consuming regularly (e.g., daily, one or more times a day, etc) at least one of different sources of alcohol (e.g., wine, beer, drinks with alcohol, etc.) within the diet. A set of features (e.g., useful for diagnostics and/or other suitable purposes, etc.) associated with an alcohol consumption condition can include features associated with (e.g., derived from) one or more of the following taxons: *Collinsella aerofaciens* (Species), *Parabacteroides distasonis* (Species), *Odoribacter splanchnicus* (Species), *Faecalibacterium prausnitzii* (Species), *Blautia luti* (Species), *Subdoligranulum variabile* (Species), *Bacteroides thetaiotaomicron* (Species), *Parabacteroides merdae* (Species), *Roseburia inulinivorans* (Species), *Flavonifractor plautii* (Species), *Streptococcus thermophilus* (Species), *Sutterella wadsworthensis* (Species), *Roseburia hominis* (Species), Clostridiales Family XIII. Incertae Sedis (Family), Coriobacteriaceae (Family), Acidaminococcaceae (Family), Lactobacillaceae (Family), Prevotellaceae (Family), Sutterellaceae (Family), Desulfovibrionaceae (Family), Enterobacteriaceae (Family), Clostridiales Family XI. Incertae Sedis (Family), Verrucomicrobiaceae (Family), Oscillospiraceae (Family), Coriobacteriales (Order), Selenomonadales (Order), Burkholderiales (Order), Desulfovibrionales (Order), Enterobacteriales (Order), Verrucomicrobiales (Order), Actinobacteria (Class), Negativicutes (Class), Betaproteobacteria (Class), Deltaproteobacteria (Class), Verrucomicrobiae (Class), Gammaproteobacteria (Class), Actinobacteria (Phylum), Proteobacteria (Phylum) and Verrucomicrobia (Phylum), and/or the microbiome features can additionally or alternatively include functional features (e.g., functional diversity features, etc.) including at least one or more of the following: Metabolism (KEGG2), Energy Metabolism (KEGG2), Xenobiotics Biodegradation and Metabolism (KEGG2), Environmental Adaptation (KEGG2), Cell Motility (KEGG2), Lipid Metabolism (KEGG2), Carbohydrate Metabolism (KEGG2), Enzyme Families (KEGG2), Nervous System (KEGG2), Transport and Catabolism (KEGG2), Poorly Characterized (KEGG2), Signaling Molecules and Interaction (KEGG2), Selenocompound metabolism (KEGG3), Propanoate metabolism (KEGG3), Fatty acid biosynthesis (KEGG3), Primary immunodeficiency (KEGG3), Phenylalanine metabolism (KEGG3), Carbon fixation pathways in prokaryotes (KEGG3), Oxidative phosphorylation (KEGG3), Plant-pathogen interaction (KEGG3), Pyruvate metabolism (KEGG3), Nitrogen metabolism (KEGG3), Inositol phosphate metabolism (KEGG3), Ascorbate and aldarate metabolism (KEGG3), Lipid biosynthesis proteins (KEGG3), Penicillin and cephalosporin biosynthesis (KEGG3), Bacterial chemotaxis (KEGG3), Type I diabetes mellitus (KEGG3), Biosynthesis and biodegradation of secondary metabolites (KEGG3), General function prediction only (KEGG3), Butanoate metabolism (KEGG3), Biosynthesis of vancomycin group antibiotics (KEGG3), Glyoxylate and dicarboxylate metabolism (KEGG3), Geraniol degradation (KEGG3), Polycyclic aromatic hydrocarbon degradation (KEGG3), Others (KEGG3), Other transporters (KEGG3), Huntington's disease (KEGG3), Biosynthesis of siderophore group nonribosomal peptides (KEGG3), Citrate cycle (TCA cycle) (KEGG3), Lysosome (KEGG3), Secretion system (KEGG3), Glutamatergic synapse (KEGG3), Energy metabolism (KEGG3), Protein kinases (KEGG3), Pentose and glucuronate interconversions (KEGG3), Nicotinate and nicotinamide metabolism (KEGG3), Ribosome Biogenesis (KEGG3), Fatty acid metabolism (KEGG3), Chromosome (KEGG3), Cysteine and methionine metabolism (KEGG3), Glycerophospholipid metabolism (KEGG3), Riboflavin metabolism (KEGG3), Terpenoid backbone biosynthesis (KEGG3), Aminobenzoate degradation (KEGG3), Amino acid metabolism (KEGG3), Fructose and mannose metabolism (KEGG3), Glycosaminoglycan degradation (KEGG3), Chloroalkane and chloroalkene degradation (KEGG3), Pores ion channels (KEGG3), Carbon fixation in photosynthetic organisms (KEGG3), Benzoate degradation (KEGG3), Sulfur metabolism (KEGG3), Lipoic acid metabolism (KEGG3), Biosynthesis of unsaturated fatty acids (KEGG3), Tryptophan metabolism (KEGG3).

Additionally or alternatively, microbiome features (e.g., microbiome composition diversity features) can include and/or otherwise be associated with (e.g., relative abundance for the taxons, etc.) one or more of the following taxons, such as in relation to a sample site (e.g., alcohol consumption condition correlations with microorganisms observed at a particular sample site): Acidobacteria (phylum; e.g., gut site), Bacteroidetes (phylum; e.g., nose site), Bacteroidetes (phylum; e.g., skin site), Candidatus Saccharibacteria (phylum; e.g., nose site), Chloroflexi (phylum; e.g., skin site), Deinococcus-Thermus (phylum; e.g., mouth site), Euryarchaeota (phylum; e.g., nose site), Fibrobacteres (phylum; e.g., gut site), Streptophyta (phylum; e.g., gut site), Synergistetes (phylum; e.g., gut site), Verrucomicrobia (phylum; e.g., gut site), Acidobacteriia (class; e.g., gut site), Bacteroidia (class; e.g., skin site), Betaproteobacteria (class; e.g., gut site), Betaproteobacteria (class; e.g., skin site), Cytophagia (class; e.g., gut site), Deinococci (class; e.g., mouth site), Deltaproteobacteria (class; e.g., genital site), Deltaproteobacteria (class; e.g., skin site), Erysipelotrichia (class; e.g., gut site), Erysipelotrichia (class; e.g., nose site), Erysipelotrichia (class; e.g., skin site), Fibrobacteria (class; e.g., gut site), Flavobacteriia (class; e.g., skin site), Gammaproteobacteria (class; e.g., gut site), Gammaproteobacteria (class; e.g., skin site), Methanobacteria (class; e.g., skin site), Negativicutes (class; e.g., skin site), Sphingobacteriia (class; e.g., skin site), Synergistia (class; e.g., gut site), Verrucomicrobiae (class; e.g., gut site), Actinomycetales (order; e.g., gut site), Anaeroplasmatales (order; e.g., mouth site), Anaeroplasmatales (order; e.g., nose site), Anaeroplasmatales (order; e.g., skin site), Bacillales (order; e.g., gut site), Bacteroidales (order; e.g., skin site), Bifidobacteriales (order; e.g., nose site), Bifidobacteriales (order; e.g., skin site), Burkholderiales (order; e.g., gut site), Burkholderiales (order; e.g., nose site), Caulobacterales (order; e.g., gut site), Caulobacterales (order; e.g., skin site), Coriobacteriales (order; e.g., skin site), Desulfovibrionales (order; e.g., genital site), Desulfovibrionales (order; e.g., skin site), Enterobacteriales (order; e.g., gut site), Erysipelotrichales (order; e.g., gut site), Erysipelotrichales (order; e.g., nose site), Erysipelotrichales (order; e.g., skin site), Fibrobacterales (order; e.g., gut site), Flavobacteriales (order; e.g., skin site), Methanobacteriales (order; e.g., skin site), Mycoplasmatales (order; e.g., gut site), Neisseriales (order; e.g., gut site), Pasteurellales (order; e.g., skin site), Pseudomonadales (order; e.g., gut site), Rhizobiales (order; e.g., gut site), Rhizobiales (order; e.g., skin site), Rhodospirillales (order; e.g., gut site), Rhodospirillales (order; e.g., skin site), Selenomonadales (order; e.g., skin site), Solanales (order; e.g., gut site), Sphingobacteriales (order; e.g., skin site), Sphingomonadales (order; e.g., skin site), Synergistales (order; e.g., gut site), Thermales (order; e.g., mouth site), Thermoanaerobacterales (order; e.g., gut site), Verrucomicrobiales (order; e.g., gut site), Acidaminococcaceae (family; e.g., gut site), Acidaminococcaceae (family; e.g., skin site), Actinomycetaceae (family; e.g., gut site), Aerococcaceae (family; e.g., genital site), Aerococcaceae (family; e.g., skin site), Anaeroplasmataceae (family; e.g., mouth site), Anaeroplasmataceae (family; e.g., nose site), Anaeroplasmataceae (family; e.g., skin site), Bacillaceae (family; e.g., gut site), Bacteroidaceae (family; e.g., gut site), Bacteroidaceae (family; e.g., nose site), Bacteroidaceae (family; e.g., skin site), Bifidobacteriaceae (family; e.g., nose site), Bifidobacteriaceae (family; e.g., skin site), Bradyrhizobiaceae (family; e.g., skin site), Carnobacteriaceae (family; e.g., gut site), Caulobacteraceae (family; e.g., gut site), Caulobacteraceae (family; e.g., skin site), Clostridiaceae (family; e.g., skin site), Clostridiales Family XIII. Incertae Sedis (family; e.g., gut site), Clostridiales Family XIII. Incertae Sedis (family; e.g., skin site), Comamonadaceae (family; e.g., nose site), Comamonadaceae (family; e.g., skin site), Coriobacteriaceae (family; e.g., skin site), Dermabacteraceae (family; e.g., nose site), Desulfovibrionaceae (family; e.g., genital site), Desulfovibrionaceae (family; e.g., skin site), Dietziaceae (family; e.g., nose site), Enterobacteriaceae (family; e.g., gut site), Erysipelotrichaceae (family; e.g., gut site), Erysipelotrichaceae (family; e.g., nose site), Erysipelotrichaceae (family; e.g., skin site), Fibrobacteraceae (family; e.g., gut site), Flavobacteriaceae (family; e.g., skin site), Fusobacteriaceae (family; e.g., nose site), Lachnospiraceae (family; e.g., gut site), Lachnospiraceae (family; e.g., skin site), Lactobacillaceae (family; e.g., gut site), Methanobacteriaceae (family; e.g., skin site), Methylobacteriaceae (family; e.g., gut site), Methylobacteriaceae (family; e.g., skin site), Microbacteriaceae (family; e.g., gut site), Micrococcaceae (family; e.g., gut site), Mycoplasmataceae (family; e.g., gut site), Neisseriaceae (family; e.g., gut site), Nocardiaceae (family; e.g., gut site), Oscillospiraceae (family; e.g., gut site), Oxalobacteraceae (family; e.g., gut site), Pasteurellaceae (family; e.g., skin site), Peptococcaceae (family; e.g., gut site), Peptostreptococcaceae (family; e.g., gut site), Planococcaceae (family; e.g., nose site), Porphyromonadaceae (family; e.g., skin site), Prevotellaceae (family; e.g., gut site), Propionibacteriaceae (family; e.g., gut site), Pseudomonadaceae (family; e.g., gut site), Rhodobacteraceae (family; e.g., gut site), Rhodospirillaceae (family; e.g., gut site), Rikenellaceae (family; e.g., nose site), Rikenellaceae (family; e.g., skin site), Ruminococcaceae (family; e.g., gut site), Ruminococcaceae (family; e.g., skin site), Sphingobacteriaceae (family; e.g., skin site), Sphingomonadaceae (family; e.g., genital site), Sphingomonadaceae (family; e.g., skin site), Staphylococcaceae (family; e.g., gut site), Sutterellaceae (family; e.g., gut site), Sutterellaceae (family; e.g., gut site), Synergistaceae (family; e.g., gut site), Thermaceae (family; e.g., mouth site), Thermoanaerobacteraceae (family; e.g., gut site), Veillonellaceae (family; e.g., gut site), Verrucomicrobiaceae (family; e.g., gut site), *Abiotrophia* (genus; e.g., gut site), *Abiotrophia* (genus; e.g., skin site), *Acetanaerobacterium* (genus; e.g., gut site), *Achromobacter* (genus; e.g., nose site), *Acidaminococcus* (genus; e.g., mouth site), *Acidaminococcus* (genus; e.g., nose site), *Actinobaculum* (genus; e.g., gut site), *Actinomyces* (genus; e.g., gut site), *Adlercreutzia* (genus; e.g., gut site), *Adlercreutzia* (genus; e.g., nose site), *Aerococcus* (genus; e.g., genital site), *Akkermansia* (genus; e.g., gut site), *Alistipes* (genus; e.g., gut site), *Alistipes* (genus; e.g., nose site), *Alistipes* (genus; e.g., skin site), *Alloprevotella* (genus; e.g., mouth site), *Anaeroplasma* (genus; e.g., mouth site), *Anaerostipes* (genus; e.g., skin site), *Anaerotruncus* (genus; e.g., genital site), *Anaerotruncus* (genus; e.g., gut site), *Anaerotruncus* (genus; e.g., skin site), *Aquabacterium* (genus; e.g., skin site), *Asaccharospora* (genus; e.g., gut site), *Atopobium* (genus; e.g., skin site), *Bacillus* (genus; e.g., gut site), *Bacteroides* (genus; e.g., gut site), *Bacteroides* (genus; e.g., nose site), *Bacteroides* (genus; e.g., skin site), *Barnesiella* (genus; e.g., skin site), *Bifidobacterium* (genus; e.g., nose site), *Bifidobacterium* (genus; e.g., skin site), *Blautia* (genus; e.g., gut site), *Blautia* (genus; e.g., skin site), *Brachybacterium* (genus; e.g., gut site), *Bradyrhizobium* (genus; e.g., skin site), *Brevundimonas* (genus; e.g., gut site), *Brevundimonas* (genus; e.g., mouth site), *Brevundimonas* (genus; e.g., skin site), *Burkholderia* (genus; e.g., skin site), *Butyricimonas* (genus; e.g., skin site), *Butyrivibrio* (genus; e.g., gut site), *Candidatus Saccharimonas* (genus; e.g., nose site), *Candidatus Soleaferrea* (genus; e.g., gut site), *Candidatus Stoquefichus* (genus; e.g., gut site), *Catonella* (genus; e.g., nose site), *Caulobacter* (genus; e.g., nose site), *Cellulosilyticum* (genus; e.g., gut site), *Chryseobacterium* (genus; e.g., gut site), *Clostridium* (genus; e.g., gut site), *Clostridium* (genus; e.g., skin site), *Collinsella* (genus; e.g., gut site), *Collinsella* (genus; e.g., skin site), *Coprobacillus* (genus; e.g., gut site), *Coprothermobacter* (genus; e.g., gut site), *Cronobacter* (genus; e.g., gut site), *Cronobacter* (genus; e.g., nose site), *Cruoricaptor* (genus; e.g., gut site), *Delftia* (genus; e.g., mouth site), *Desulfovibrio* (genus; e.g., skin site), *Dialister* (genus; e.g., gut site), *Dielma* (genus; e.g., gut site), *Dorea* (genus; e.g., gut site), *Dorea* (genus; e.g., skin site), *Eggerthella* (genus; e.g., gut site), *Eggerthella* (genus; e.g., mouth site), *Eisenbergiella* (genus; e.g., gut site), *Enterobacter* (genus; e.g., gut site), *Enterorhabdus* (genus; e.g., nose site), *Epulopiscium* (genus; e.g., gut site), *Eremococcus* (genus; e.g., genital site), *Eremococcus* (genus; e.g., gut site), *Erysipelatoclostridium* (genus; e.g., gut site), *Erysipelatoclostridium* (genus; e.g., skin site), *Faecalibacterium* (genus; e.g., gut site), *Faecalibacterium* (genus; e.g., skin site), *Flavobacterium* (genus; e.g., mouth site), *Flavobacterium* (genus; e.g., skin site), *Flavonifractor* (genus; e.g., gut site), *Flavonifractor* (genus; e.g., skin site), *Fusicatenibacter* (genus; e.g., gut site), *Fusicatenibacter* (genus; e.g., skin site), *Fusobacterium* (genus; e.g., nose site), *Gelria* (genus; e.g., gut site), *Gordonibacter* (genus; e.g., gut site), *Granulicatella* (genus; e.g., gut site), *Haemophilus* (genus; e.g., nose site), *Herbaspirillum* (genus; e.g., gut site), *Hespellia* (genus; e.g., genital site), *Holdemania* (genus; e.g., gut site), *Intestinibacter* (genus; e.g., gut site), *Klebsiella* (genus; e.g., gut site), *Kluyvera* (genus; e.g., gut site), *Lachnospira* (genus; e.g., nose site), *Lachnospira* (genus; e.g., skin site), *Lactobacillus* (genus; e.g., gut site), *Lactonifactor* (genus; e.g., gut site), *Megamonas* (genus; e.g., nose site), *Megasphaera* (genus; e.g., gut site), *Megasphaera* (genus; e.g., skin site), *Methanosphaera* (genus; e.g., mouth site), *Methylobacterium* (genus; e.g., gut site), *Methylobacterium* (genus; e.g., skin site), *Moraxella* (genus; e.g., gut site), *Moryella* (genus; e.g., gut site), *Mycoplasma* (genus; e.g., gut site), *Neisseria* (genus; e.g., gut site), *Odoribacter* (genus; e.g., skin site), *Oscillibacter* (genus; e.g., gut site), *Pantoea* (genus; e.g., gut site), *Papillibacter* (genus; e.g., gut site), *Parabacteroides* (genus; e.g., skin site), *Parvimonas* (genus; e.g., genital site), *Pasteurella* (genus; e.g., skin site), *Pedobacter* (genus; e.g., skin site), *Pelomonas* (genus; e.g., genital site), *Peptoclostridium* (genus; e.g., gut site), *Peptococcus* (genus; e.g., nose site), *Phascolarctobacterium* (genus; e.g., gut site), *Phascolarctobacterium* (genus; e.g., skin site), *Planomicrobium* (genus; e.g., gut site), *Porphyromonas* (genus; e.g., skin site), *Prevotella* (genus; e.g., gut site), *Propionibacterium* (genus; e.g., gut site), *Pseudobutyrivibrio* (genus; e.g., gut site), *Pseudobutyrivibrio* (genus; e.g., skin site), *Pseudoclavibacter* (genus; e.g., nose site), *Pseudoflavonifractor* (genus; e.g., gut site), *Pseudomonas* (genus; e.g., gut site), *Ralstonia* (genus; e.g., skin site), *Rhodobacter* (genus; e.g., nose site), *Rhodococcus* (genus; e.g., gut site), *Romboutsia* (genus; e.g., gut site), *Roseburia*

(genus; e.g., gut site), *Roseburia* (genus; e.g., skin site), *Roseomonas* (genus; e.g., skin site), *Rothia* (genus; e.g., gut site), *Sarcina* (genus; e.g., skin site), *Selenomonas* (genus; e.g., skin site), *Senegalimassilia* (genus; e.g., genital site), *Shuttleworthia* (genus; e.g., gut site), *Sphingobacterium* (genus; e.g., skin site), *Sphingomonas* (genus; e.g., genital site), *Staphylococcus* (genus; e.g., gut site), *Stomatobaculum* (genus; e.g., skin site), *Streptobacillus* (genus; e.g., nose site), *Streptococcus* (genus; e.g., gut site), *Subdoligranulum* (genus; e.g., gut site), *Subdoligranulum* (genus; e.g., skin site), *Succinatimonas* (genus; e.g., gut site), *Sutterella* (genus; e.g., gut site), *Sutterella* (genus; e.g., skin site), *Syntrophococcus* (genus; e.g., gut site), *Terrisporobacter* (genus; e.g., skin site), *Tessaracoccus* (genus; e.g., gut site), *Thalassospira* (genus; e.g., gut site), *Thalassospira* (genus; e.g., skin site), *Turicibacter* (genus; e.g., gut site), *Turicibacter* (genus; e.g., nose site), *Varibaculum* (genus; e.g., gut site), *Varibaculum* (genus; e.g., mouth site), *Veillonella* (genus; e.g., gut site), *Abiotrophia defectiva* (species; e.g., gut site), *Abiotrophia defectiva* (species; e.g., skin site), *Achromobacter xylosoxidans* (species; e.g., nose site), *Acidaminococcus intestini* (species; e.g., gut site), *Acidaminococcus* sp. D21 (species; e.g., nose site), *Acinetobacter* sp. 511B (species; e.g., nose site), *Acinetobacter* sp. S2 (2009) (species; e.g., skin site), *Actinobaculum schaalii* (species; e.g., gut site), *Actinomyces meyeri* (species; e.g., mouth site), *Actinomyces odontolyticus* (species; e.g., nose site), *Actinomyces* sp. oral strain Hal-1065 (species; e.g., gut site), *Actinomyces* sp. oral taxon 175 (species; e.g., gut site), *Actinomyces viscosus* (species; e.g., nose site), *Adlercreutzia equolifaciens* (species; e.g., gut site), *Adlercreutzia equolifaciens* (species; e.g., nose site), *Aerosphaera taetra* (species; e.g., gut site), *Akkermansia muciniphila* (species; e.g., skin site), *Alistipes finegoldii* (species; e.g., gut site), *Alistipes indistinctus* (species; e.g., gut site), *Alistipes putredinis* (species; e.g., skin site), *Alistipes shahii* (species; e.g., gut site), *Alistipes* sp. 627 (species; e.g., skin site), *Alistipes* sp. EBA6-25cl2 (species; e.g., skin site), *Alistipes* sp. HGB5 (species; e.g., gut site), *Alistipes* sp. RMA 9912 (species; e.g., skin site), *Anaerococcus hydrogenalis* (species; e.g., nose site), *Anaerococcus* sp. 9401487 (species; e.g., genital site), *Anaerococcus* sp. 9401487 (species; e.g., gut site), *Anaeroglobus geminatus* (species; e.g., gut site), *Anaerostipes hadrus* (species; e.g., gut site), *Anaerostipes* sp. 5_1_63FAA (species; e.g., gut site), *Anaerostipes* sp. 5_1_63FAA (species; e.g., skin site), *Anaerotruncus colihominis* (species; e.g., gut site), *Anaerovibrio* sp. 765 (species; e.g., gut site), *Arcanobacterium* sp. NML 06501 (species; e.g., genital site), *Asaccharospora irregularis* (species; e.g., skin site), *Atopobium* sp. F0209 (species; e.g., genital site), *Atopobium* sp. F0209 (species; e.g., gut site), *Atopobium* sp. S3PFAA1-4 (species; e.g., genital site), *Bacteroides acidifaciens* (species; e.g., nose site), *Bacteroides caccae* (species; e.g., skin site), *Bacteroides chinchillae* (species; e.g., gut site), *Bacteroides dorei* (species; e.g., gut site), *Bacteroides eggerthii* (species; e.g., nose site), *Bacteroides finegoldii* (species; e.g., gut site), *Bacteroides finegoldii* (species; e.g., skin site), *Bacteroides fragilis* (species; e.g., genital site), *Bacteroides massiliensis* (species; e.g., gut site), *Bacteroides nordii* (species; e.g., gut site), *Bacteroides ovatus* (species; e.g., gut site), *Bacteroides plebeius* (species; e.g., skin site), *Bacteroides salyersiae* (species; e.g., mouth site), *Bacteroides* sp. 35AE37 (species; e.g., gut site), *Bacteroides* sp. AR20 (species; e.g., gut site), *Bacteroides* sp. AR20 (species; e.g., skin site), *Bacteroides* sp. AR29 (species; e.g., gut site), *Bacteroides* sp. AR29 (species; e.g., skin site), *Bacteroides* sp. D22 (species; e.g., skin site), *Bacteroides* sp. DJF_B097 (species; e.g., gut site), *Bacteroides* sp. DJF_B097 (species; e.g., skin site), *Bacteroides* sp. EBA5-17 (species; e.g., gut site), *Bacteroides* sp. J1511 (species; e.g., gut site), *Bacteroides* sp. S-17 (species; e.g., gut site), *Bacteroides* sp. SLC1-38 (species; e.g., gut site), *Bacteroides* sp. SLC1-38 (species; e.g., skin site), *Bacteroides* sp. XB12B (species; e.g., genital site), *Bacteroides* sp. XB12B (species; e.g., skin site), *Bacteroides stercoris* (species; e.g., gut site), *Bacteroides thetaiotaomicron* (species; e.g., gut site), *Bacteroides uniformis* (species; e.g., gut site), *Bacteroides vulgatus* (species; e.g., skin site), *Barnesiella intestinihominis* (species; e.g., gut site), *Barnesiella intestinihominis* (species; e.g., nose site), *Barnesiella intestinihominis* (species; e.g., skin site), *Bergeyella* sp. AF14 (species; e.g., skin site), *Bifidobacterium adolescentis* (species; e.g., gut site), *Bifidobacterium breve* (species; e.g., gut site), *Bifidobacterium kashiwanohense* (species; e.g., nose site), *Bifidobacterium longum* (species; e.g., gut site), *Bifidobacterium longum* (species; e.g., mouth site), *Bifidobacterium pseudocatenulatum* (species; e.g., gut site), *Bifidobacterium* sp. MSX5B (species; e.g., mouth site), *Bifidobacterium stercoris* (species; e.g., skin site), *Bilophila* sp. 4_1_30 (species; e.g., gut site), *Bilophila wadsworthia* (species; e.g., gut site), *Blautia coccoides* (species; e.g., gut site), *Blautia faecis* (species; e.g., skin site), *Blautia luti* (species; e.g., skin site), *Blautia* sp. YHC-4 (species; e.g., genital site), *Blautia* sp. YHC-4 (species; e.g., skin site), *Blautia stercoris* (species; e.g., gut site), *Blautia stercoris* (species; e.g., nose site), *Blautia wexlerae* (species; e.g., skin site), *Brachybacterium* sp. NIO-27 (species; e.g., gut site), *Brevundimonas* sp. FXJ8.080 (species; e.g., gut site), *Brevundimonas* sp. FXJ8.080 (species; e.g., mouth site), *Brevundimonas* sp. FXJ8.080 (species; e.g., nose site), *Brevundimonas* sp. FXJ8.080 (species; e.g., skin site), *Butyricimonas* sp. JCM 18676 (species; e.g., mouth site), *Butyricimonas* sp. JCM 18677 (species; e.g., skin site), *Butyricimonas virosa* (species; e.g., mouth site), *Butyricimonas virosa* (species; e.g., nose site), *Butyrivibrio crossotus* (species; e.g., gut site), *Campylobacter gracilis* (species; e.g., nose site), *Campylobacter* sp. FOBRC15 (species; e.g., nose site), *Capnocytophaga sputigena* (species; e.g., gut site), *Catonella morbi* (species; e.g., nose site), *Chryseobacterium hominis* (species; e.g., nose site), *Chryseobacterium hominis* (species; e.g., skin site), *Collinsella aerofaciens* (species; e.g., gut site), *Collinsella aerofaciens* (species; e.g., skin site), *Coprobacillus* sp. D6 (species; e.g., gut site), *Corynebacterium canis* (species; e.g., genital site), *Corynebacterium canis* (species; e.g., mouth site), *Corynebacterium* sp. (species; e.g., mouth site), *Cronobacter sakazakii* (species; e.g., gut site), *Cronobacter sakazakii* (species; e.g., nose site), *Cruoricaptor ignavus* (species; e.g., gut site), *Delftia* sp. BN-SKY3 (species; e.g., mouth site), *Desulfovibrio piger* (species; e.g., gut site), *Dialister invisus* (species; e.g., genital site), *Dialister micraerophilus* (species; e.g., nose site), *Dialister propionicifaciens* (species; e.g., mouth site), *Dialister propionicifaciens* (species; e.g., nose site), *Dialister* sp. E2_20 (species; e.g., gut site), *Dialister* sp. S4-23 (species; e.g., gut site), *Dielma fastidiosa* (species; e.g., gut site), *Dorea formicigenerans* (species; e.g., genital site), *Dorea formicigenerans* (species; e.g., gut site), *Dorea longicatena* (species; e.g., gut site), *Dorea longicatena* (species; e.g., skin site), *Eggerthella lenta* (species; e.g., gut site), *Eggerthella* sp. HGA1 (species; e.g., gut site), *Eggerthella* sp. HGA1 (species; e.g., mouth site), *Eisenbergiella tayi* (species; e.g., gut site), *Enterococcus faecalis* (species; e.g., gut site), *Eremococcus coleocola* (species; e.g., gut site), *Erysipelatoclostridium ramosum*

(species; e.g., gut site), *Faecalibacterium prausnitzii* (species; e.g., gut site), *Faecalibacterium prausnitzii* (species; e.g., skin site), *Faecalibacterium* sp. canine oral taxon 147 (species; e.g., gut site), *Finegoldia magna* (species; e.g., gut site), *Finegoldia magna* (species; e.g., skin site), *Finegoldia* sp. S9 AA1-5 (species; e.g., gut site), *Flavobacterium ceti* (species; e.g., genital site), *Flavobacterium ceti* (species; e.g., gut site), *Flavobacterium ceti* (species; e.g., mouth site), *Flavobacterium ceti* (species; e.g., nose site), *Flavobacterium ceti* (species; e.g., skin site), *Flavonifractor plautii* (species; e.g., gut site), *Fusicatenibacter saccharivorans* (species; e.g., skin site), *Fusobacterium mortiferum* (species; e.g., gut site), *Fusobacterium periodonticum* (species; e.g., mouth site), *Fusobacterium ulcerans* (species; e.g., gut site), *Gemella sanguinis* (species; e.g., mouth site), *Gemella* sp. 933-88 (species; e.g., mouth site), *Gordonibacter pamelaeae* (species; e.g., gut site), *Granulicatella elegans* (species; e.g., skin site), *Haemophilus parainfluenzae* (species; e.g., skin site), *Herbaspirillum huttiense* (species; e.g., skin site), *Herbaspirillum seropedicae* (species; e.g., gut site), *Holdemania filiformis* (species; e.g., gut site), *Intestinimonas butyriciproducens* (species; e.g., gut site), *Janibacter* sp. M3-5 (species; e.g., nose site), *Klebsiella* sp. SOR89 (species; e.g., gut site), *Kluyvera georgiana* (species; e.g., gut site), *Kocuria* sp. FXJ6.339 (species; e.g., skin site), *Kocuria* sp. M1-36 (species; e.g., nose site), *Lachnoanaerobaculum* sp. MSX33 (species; e.g., mouth site), *Lachnospira pectinoschiza* (species; e.g., gut site), *Lachnospira pectinoschiza* (species; e.g., skin site), *Lactobacillus johnsonii* (species; e.g., genital site), *Lactobacillus* sp. 7_1_47FAA (species; e.g., genital site), *Lactobacillus* sp. 7_1_47FAA (species; e.g., gut site), *Lactobacillus* sp. 7_1_47FAA (species; e.g., skin site), *Lactobacillus* sp. Akhmro1 (species; e.g., nose site), *Lactonifactor longoviformis* (species; e.g., gut site), *Leptotrichia hofstadii* (species; e.g., nose site), *Leptotrichia hongkongensis* (species; e.g., nose site), *Leptotrichia shahii* (species; e.g., nose site), *Megamonas funiformis* (species; e.g., nose site), *Megamonas rupellensis* (species; e.g., gut site), *Methylobacterium* sp. PDD-23b-14 (species; e.g., skin site), *Mogibacterium* sp. CM96 (species; e.g., gut site), *Mycobacterium* sp. KNUC297 (species; e.g., nose site), *Neisseria* sp. CCUG 45853 (species; e.g., mouth site), *Neisseria* sp. SMC-A9199 (species; e.g., mouth site), *Odoribacter splanchnicus* (species; e.g., gut site), *Odoribacter splanchnicus* (species; e.g., skin site), *Olsenella* sp. S9 HS-6 (species; e.g., gut site), *Pantoea* sp. CWB304 (species; e.g., gut site), *Parabacteroides distasonis* (species; e.g., gut site), *Parabacteroides johnsonii* (species; e.g., skin site), *Parabacteroides merdae* (species; e.g., genital site), *Parabacteroides merdae* (species; e.g., skin site), *Parabacteroides* sp. 157 (species; e.g., mouth site), *Paraprevotella clara* (species; e.g., nose site), *Parvimonas* sp. oral taxon 393 (species; e.g., gut site), *Pasteurella pneumotropica* (species; e.g., skin site), *Pedobacter heparinus* (species; e.g., skin site), *Pelomonas aquatica* (species; e.g., genital site), *Peptoclostridium difficile* (species; e.g., gut site), *Peptoniphilus* sp. gpac148 (species; e.g., gut site), *Peptoniphilus* sp. oral taxon 375 (species; e.g., gut site), *Peptoniphilus* sp. oral taxon 375 (species; e.g., nose site), *Peptoniphilus* sp. oral taxon 836 (species; e.g., nose site), *Peptoniphilus* sp. S3PFAA2-10 (species; e.g., gut site), *Phascolarctobacterium* sp. 377 (species; e.g., gut site), *Phascolarctobacterium* sp. 377 (species; e.g., nose site), *Phascolarctobacterium succinatutens* (species; e.g., gut site), *Phascolarctobacterium succinatutens* (species; e.g., mouth site), *Phascolarctobacterium succinatutens* (species; e.g., nose site), *Porphyromonas uenonis* (species; e.g., genital site), *Porphyromonas uenonis* (species; e.g., nose site), *Prevotella disiens* (species; e.g., skin site), *Prevotella intermedia* (species; e.g., nose site), *Prevotella oulorum* (species; e.g., nose site), *Prevotella* sp. WAL 2039G (species; e.g., mouth site), *Propionibacterium acnes* (species; e.g., nose site), *Propionibacterium* sp. KPL1844 (species; e.g., skin site), *Pseudoflavonifractor capillosus* (species; e.g., gut site), *Pseudomonas brenneri* (species; e.g., gut site), *Pseudomonas brenneri* (species; e.g., mouth site), *Pseudomonas brenneri* (species; e.g., nose site), *Pseudomonas brenneri* (species; e.g., skin site), *Pseudomonas* sp. GmFRB023 (species; e.g., mouth site), *Pseudomonas* sp. KB23 (species; e.g., nose site), *Pseudomonas* sp. KB23 (species; e.g., skin site), *Roseburia faecis* (species; e.g., gut site), *Roseburia hominis* (species; e.g., skin site), *Roseburia intestinalis* (species; e.g., genital site), *Roseburia inulinivorans* (species; e.g., gut site), *Roseburia inulinivorans* (species; e.g., skin site), *Roseburia* sp. 11SE39 (species; e.g., gut site), *Roseburia* sp. 11SE39 (species; e.g., skin site), *Roseburia* sp. DJF_RR73 (species; e.g., gut site), *Rothia dentocariosa* (species; e.g., gut site), *Rothia mucilaginosa* (species; e.g., mouth site), *Selenomonas* sp. CM52 (species; e.g., gut site), *Selenomonas* sp. CM52 (species; e.g., skin site), *Slackia exigua* (species; e.g., gut site), *Sphingobacterium spiritivorum* (species; e.g., nose site), *Sphingobacterium spiritivorum* (species; e.g., skin site), *Sphingomonas* sp. 24T (species; e.g., nose site), *Sphingomonas* sp. 540 (species; e.g., skin site), *Staphylococcus* sp. C9I2 (species; e.g., gut site), *Staphylococcus* sp. L10 (species; e.g., nose site), *Staphylococcus* sp. L10 (species; e.g., skin site), *Stenotrophomonas* sp. KITS-1 (species; e.g., nose site), *Stenotrophomonas* sp. UYSO33 (species; e.g., nose site), *Stenotrophomonas* sp. UYSO33 (species; e.g., skin site), *Streptococcus dysgalactiae* (species; e.g., gut site), *Streptococcus equinus* (species; e.g., gut site), *Streptococcus gordonii* (species; e.g., gut site), *Streptococcus parasanguinis* (species; e.g., gut site), *Streptococcus* sp. 2011_Oral_MS_A3 (species; e.g., gut site), *Streptococcus* sp. BS35a (species; e.g., gut site), *Streptococcus* sp. BS35a (species; e.g., mouth site), *Streptococcus* sp. oral taxon G59 (species; e.g., gut site), *Streptococcus thermophilus* (species; e.g., skin site), *Subdoligranulum variabile* (species; e.g., gut site), *Subdoligranulum variabile* (species; e.g., skin site), *Succinatimonas hippei* (species; e.g., gut site), *Sutterella* sp. 252 (species; e.g., mouth site), *Sutterella wadsworthensis* (species; e.g., gut site), *Sutterella wadsworthensis* (species; e.g., skin site), *Terrisporobacter glycolicus* (species; e.g., gut site), *Tessaracoccus* sp. IPBSL-7 (species; e.g., gut site), *Tessaracoccus* sp. SL014B-79A (species; e.g., gut site), *Turicibacter sanguinis* (species; e.g., gut site), *Turicibacter sanguinis* (species; e.g., nose site), *Veillonella atypica* (species; e.g., nose site), *Veillonella rogosae* (species; e.g., gut site), *Veillonella* sp. 6_1_27 (species; e.g., mouth site), *Veillonella* sp. AS16 (species; e.g., gut site), *Veillonella* sp. oral taxon 780 (species; e.g., mouth site).

3.3.E Extreme Physical Exercise Characterization Process.

In a variation, Block S130 can include performing an extreme physical exercise characterization process (e.g., determining and/or applying a extreme physical exercise characterization model; etc.) for one or more users.

In one implementation, a characterization process of Block S130 based upon statistical analyses can identify the sets of features that have the highest correlations with extreme physical exercise associated-microorganisms for which one or more therapies would have a positive effect, such as based upon a random forest predictor algorithm (and/or other suitable model) trained with a training dataset derived from a subset of the population of subjects, and/or validated with a validation dataset derived from a subset of the population of subjects. In particular, an extreme physical exercise condition can include a human lifestyle behavior characterized by engaging in physical exercise for at least two hours or more during a day, at least five (or more) days a week, and/or for any suitable amount of physical exercise beyond a threshold. In addition, engaging in physical exercise can include a characteristic of a subgroup of the general population having lower prevalence and burden of physical and mental illnesses, such as cardiovascular disease or depressive disorder. Typical methods of diagnosis are based on personal interview and self-assessment of physical activity. In addition, general physical evaluation and laboratory tests, such as blood tests, can be associated with this condition by being proxies of good health and low disease burden. A set of features (e.g., useful for diagnostics and/or other suitable purposes, etc.) associated with an extreme physical exercise condition can include features associated with (e.g., derived from) one or more of a combination of the following taxons: Negativicutes (class), Clostridia (class), Bacteroidia (class), Verrucomicrobiae (class), Deltaproteobacteria (class), Gammaproteobacteria (class), Clostridiaceae (family), Bacteroidaceae (family), Oscillospiraceae (family), Acidaminococcaceae (family), Veillonellaceae (family), Ruminococcaceae (family), Prevotellaceae (family), Bifidobacteriaceae (family), Lactobacillaceae (family), Verrucomicrobiaceae (family), Streptococcaceae (family), Desulfovibrionaceae (family), Porphyromonadaceae (family), Coriobacteriaceae (family), *Clostridium* (genus), *Bacteroides* (genus), *Parabacteroides* (genus), *Bilophila* (genus), *Marvinbryantia* (genus), *Bifidobacterium* (genus), *Akkermansia* (genus), *Acidaminococcus* (genus), *Megamonas* (genus), *Lachnospira* (genus), *Faecalibacterium* (genus), *Phascolarctobacterium* (genus), *Pseudobutyrivibrio* (genus), *Roseburia* (genus), *Anaerotruncus* (genus), *Veillonella* (genus), *Sarcina* (genus), *Parasutterella* (genus), Selenomonadales (order), Clostridiales (order), Bacteroidales (order), Bifidobacteriales (order), Verrucomicrobiales (order), Desulfovibrionales (order), Bacteroidetes (phylum), Firmicutes (phylum), Verrucomicrobia (phylum), *Bacteroides vulgatus* (species), *Parabacteroides merdae* (species), *Bacteroides caccae* (species), *Collinsella aerofaciens* (species), *Phascolarctobacterium faecium* (species), *Bacteroides fragilis* (species), *Parabacteroides distasonis* (species), *Flavonifractor plautii* (species), *Megamonas funiformis* (species), *Roseburia inulinivorans* (species), and/or the microbiome features can additionally or alternatively include functional features (e.g., functional diversity features, etc.) including at least one or a combination of the following: Translation (KEGG2), Cellular Processes and Signaling (KEGG2), Metabolism (KEGG2), Biosynthesis of Other Secondary Metabolites (KEGG2), Replication and Repair (KEGG2), Cell Growth and Death (KEGG2), Carbohydrate Metabolism (KEGG2), Poorly Characterized (KEGG2), Signaling Molecules and Interaction (KEGG2), Transport and Catabolism (KEGG2), Glycan Biosynthesis and Metabolism (KEGG2), Nucleotide Metabolism (KEGG2), Energy Metabolism (KEGG2), Environmental Adaptation (KEGG2), Metabolism of Terpenoids and Polyketides (KEGG2), Lipid Metabolism (KEGG2), Metabolism of Other Amino Acids (KEGG2), Inorganic ion transport and metabolism (KEGG3), Ribosome Biogenesis (KEGG3), Aminoacyl-tRNA biosynthesis (KEGG3), Amino acid related enzymes (KEGG3), Amino acid metabolism (KEGG3), Ribosome (KEGG3), Other transporters (KEGG3), RNA polymerase (KEGG3), Biotin metabolism (KEGG3), Sphingolipid metabolism (KEGG3), Phosphatidylinositol signaling system (KEGG3), Galactose metabolism (KEGG3), Ribosome biogenesis in eukaryotes (KEGG3), Other glycan degradation (KEGG3), Other ion-coupled transporters (KEGG3), Glycosphingolipid biosynthesis—globo series (KEGG3), Amino sugar and nucleotide sugar metabolism (KEGG3), Homologous recombination (KEGG3), DNA repair and recombination proteins (KEGG3), Terpenoid backbone biosynthesis (KEGG3), Translation factors (KEGG3), Carbohydrate metabolism (KEGG3), Pentose and glucuronate interconversions (KEGG3), Lysosome (KEGG3), Peptidoglycan biosynthesis (KEGG3), Pyrimidine metabolism (KEGG3), Alzheimer's disease (KEGG3), Nitrogen metabolism (KEGG3), Translation proteins (KEGG3), Glycosaminoglycan degradation (KEGG3), Others (KEGG3), Protein export (KEGG3), Function unknown (KEGG3), Starch and sucrose metabolism (KEGG3), Cell cycle—*Caulobacter* (KEGG3), Bacterial toxins (KEGG3), Tuberculosis (KEGG3), Cyanoamino acid metabolism (KEGG3), Glyoxylate and dicarboxylate metabolism (KEGG3), D-Alanine metabolism (KEGG3), Photosynthesis proteins (KEGG3), Mismatch repair (KEGG3), Photosynthesis (KEGG3), Nicotinate and nicotinamide metabolism (KEGG3), Base excision repair (KEGG3), Biosynthesis of siderophore group nonribosomal peptides (KEGG3), Nucleotide excision repair (KEGG3), Glycosphingolipid biosynthesis—ganglio series (KEGG3), Pores ion channels (KEGG3), Phenylpropanoid biosynthesis (KEGG3), Chromosome (KEGG3), Penicillin and cephalosporin biosynthesis (KEGG3), Bisphenol degradation (KEGG3), Pantothenate and CoA biosynthesis (KEGG3), DNA replication proteins (KEGG3), Prenyltransferases (KEGG3), Vitamin metabolism (KEGG3), Plant-pathogen interaction (KEGG3), DNA replication (KEGG3), Lipopolysaccharide biosynthesis proteins (KEGG3), Propanoate metabolism (KEGG3), Membrane and intracellular structural molecules (KEGG3), Insulin signaling pathway (KEGG3), Arginine and proline metabolism (KEGG3), Fructose and mannose metabolism (KEGG3), Polyketide sugar unit biosynthesis (KEGG3), Benzoate degradation (KEGG3), Cell motility and secretion (KEGG3), One carbon pool by folate (KEGG3), Cell division (KEGG3), Oxidative phosphorylation (KEGG3), Streptomycin biosynthesis (KEGG3), Sulfur metabolism (KEGG3), Butanoate metabolism (KEGG3), Biosynthesis and biodegradation of secondary metabolites (KEGG3), Phenylalanine metabolism (KEGG3), Primary immunodeficiency (KEGG3), Biosynthesis of vancomycin group antibiotics (KEGG3), Carbon fixation in photosynthetic organisms (KEGG3), Glycosyltransferases (KEGG3), Drug metabolism—other enzymes (KEGG3), Tryptophan metabolism (KEGG3).

3.3.F Moderate Physical Exercise Characterization Process.

In a variation, Block S130 can include performing a moderate physical exercise characterization process (e.g., determining and/or applying a moderate physical exercise characterization model; etc.) for one or more users. However, Block S130 and/or other suitable portions of the method 100 can be for adapted for any suitable level of physical exercise.

In one implementation, a characterization process of Block S130 based upon statistical analyses can identify the sets of features that have the highest correlations with moderate physical exercises associated-microorganisms for which one or more therapies would have a positive effect, such as based upon a random forest predictor algorithm (and/or other suitable model) trained with a training dataset derived from a subset of the population of subjects, and/or validated with a validation dataset derived from a subset of the population of subjects. In particular, moderate physical exercise conditions can include a human lifestyle behavior characterized by engaging in physical exercise for no more than two hours, at least more than one of five days a week, and/or any suitable amount of physical exercise. A set of features (e.g., useful for diagnostics and/or other suitable purposes, etc.) associated with one or more moderate physical exercise conditions can include features associated with (e.g., derived from) one or more of a combination of the following taxons: Negativicutes (class), Clostridia (class), Bacteroidia (class), Verrucomicrobiae (class), Clostridiaceae (family), Bacteroidaceae (family), Acidaminococcaceae (family), Ruminococcaceae (family), Prevotellaceae (family), Oscillospiraceae (family), Bifidobacteriaceae (family), Lactobacillaceae (family), Coriobacteriaceae (family), Verrucomicrobiaceae (family), Veillonellaceae (family), *Clostridium* (genus), *Bacteroides* (genus), *Parabacteroides* (genus), *Bilophila* (genus), *Moryella* (genus), *Bifidobacterium* (genus), *Faecalibacterium* (genus), *Phascolarctobacterium* (genus), *Acidaminococcus* (genus), *Marvinbryantia* (genus), *Blautia* (genus), *Parasutterella* (genus), *Sarcina* (genus), *Akkermansia* (genus), Selenomonadales (order), Clostridiales (order), Bacteroidales (order), Bifidobacteriales (order), Coriobacteriales (order), Verrucomicrobiales (order), Bacteroidetes (phylum), Firmicutes (phylum), Verrucomicrobia (phylum), *Bacteroides vulgatus* (species), *Bacteroides caccae* (species), *Parabacteroides merdae* (species), *Phascolarctobacterium faecium* (species), *Parabacteroides distasonis* (species), *Flavonifractor plautii* (species), *Bacteroides fragilis* (species), *Parasutterella excrementihominis* (species), *Blautia* sp. YHC-4 (species), *Collinsella aerofaciens* (species), *Faecalibacterium prausnitzii* (species), and/or the microbiome features can additionally or alternatively include functional features (e.g., functional diversity features, etc.) including at least one or a combination of the following: Translation (KEGG2), Cellular Processes and Signaling (KEGG2), Metabolism (KEGG2), Carbohydrate Metabolism (KEGG2), Replication and Repair (KEGG2), Cell Growth and Death (KEGG2), Signaling Molecules and Interaction (KEGG2), Environmental Adaptation (KEGG2), Poorly Characterized (KEGG2), Nucleotide Metabolism (KEGG2), Biosynthesis of Other Secondary Metabolites (KEGG2), Glycan Biosynthesis and Metabolism (KEGG2), Transport and Catabolism (KEGG2), Metabolism of Terpenoids and Polyketides (KEGG2), Cell Motility (KEGG2), Lipid Metabolism (KEGG2), Ribosome Biogenesis (KEGG3), Inorganic ion transport and metabolism (KEGG3), Amino acid metabolism (KEGG3), Ribosome (KEGG3), Amino acid related enzymes (KEGG3), Aminoacyl-tRNA biosynthesis (KEGG3), Ribosome biogenesis in eukaryotes (KEGG3), Galactose metabolism (KEGG3), RNA polymerase (KEGG3), Terpenoid backbone biosynthesis (KEGG3), Other ion-coupled transporters (KEGG3), Peptidoglycan biosynthesis (KEGG3), Translation factors (KEGG3), Homologous recombination (KEGG3), Phosphatidylinositol signaling system (KEGG3), DNA repair and recombination proteins (KEGG3), Amino sugar and nucleotide sugar metabolism (KEGG3), Biotin metabolism (KEGG3), Bacterial toxins (KEGG3), Others (KEGG3), Translation proteins (KEGG3), Pyrimidine metabolism (KEGG3), Other transporters (KEGG3), Alzheimer's disease (KEGG3), Tuberculosis (KEGG3), Sphingolipid metabolism (KEGG3), Other glycan degradation (KEGG3), Function unknown (KEGG3), Cell cycle—*Caulobacter* (KEGG3), Protein export (KEGG3), Glycosphingolipid biosynthesis—globo series (KEGG3), Nitrogen metabolism (KEGG3), Fructose and mannose metabolism (KEGG3), Carbohydrate metabolism (KEGG3), Nicotinate and nicotinamide metabolism (KEGG3), Pentose and glucuronate interconversions (KEGG3), Glyoxylate and dicarboxylate metabolism (KEGG3), Nucleotide excision repair (KEGG3), Plant-pathogen interaction (KEGG3), Chromosome (KEGG3), Mismatch repair (KEGG3), D-Alanine metabolism (KEGG3), DNA replication proteins (KEGG3), Photosynthesis proteins (KEGG3), Lysosome (KEGG3), Glycosaminoglycan degradation (KEGG3), Penicillin and cephalosporin biosynthesis (KEGG3), Photosynthesis (KEGG3), Vitamin metabolism (KEGG3), Ascorbate and aldarate metabolism (KEGG3), Base excision repair (KEGG3), Prenyltransferases (KEGG3), Biosynthesis of siderophore group nonribosomal peptides (KEGG3), Pantothenate and CoA biosynthesis (KEGG3), One carbon pool by folate (KEGG3), Pores ion channels (KEGG3), Bisphenol degradation (KEGG3), Starch and sucrose metabolism (KEGG3), DNA replication (KEGG3), Primary immunodeficiency (KEGG3), Membrane and intracellular structural molecules (KEGG3), Glycosphingolipid biosynthesis—ganglio series (KEGG3), Lipopolysaccharide biosynthesis proteins (KEGG3), Cyanoamino acid metabolism (KEGG3), Cell motility and secretion (KEGG3), Riboflavin metabolism (KEGG3), Drug metabolism—other enzymes (KEGG3), Glycosyltransferases (KEGG3), Taurine and hypotaurine metabolism (KEGG3), Sulfur metabolism (KEGG3), Biosynthesis and biodegradation of secondary metabolites (KEGG3).

3.3.G Menopause Characterization Process.

In a variation, Block S130 can include performing a menopause condition characterization process (e.g., determining and/or applying a menopause consumption characterization model; etc.) for one or more users.

In one implementation, a characterization process of Block S130 based upon statistical analyses can identify the sets of features that have the highest correlations with a menopause condition for which one or more therapies would have a positive effect, such as based upon a random forest predictor algorithm (and/or other suitable model) trained with a training dataset derived from a subset of the population of subjects, and/or validated with a validation dataset derived from a subset of the population of subjects. In particular, a menopause condition can include a state of the body of a woman, starting 12 months after last menstrual period and marks the end of menstrual cycles characterized by absence of menstrual cycle for a long period, and diagnosis can include blood test samples (e.g., FSH, TSH, etc.). A set of features (e.g., useful for diagnostics and/or other suitable purposes, etc.) associated with a caffeine consumption condition can include features associated with (e.g., derived from) one or more of the following taxons: Lactobacillaceae (Family), Clostridia (Class), Clostridiales (Order) or any other microorganisms associated with present condition, and/or any functional features associated with condition related to microorganisms associated with present condition.

Additionally or alternatively, microbiome features (e.g., microbiome composition diversity features) can include and/or otherwise be associated with (e.g., relative abundance for the taxons, etc.) one or more of the following taxons, such as in relation to a sample site (e.g., menopause condition correlations with microorganisms observed at a particular sample site): Actinobacteria (phylum; e.g., skin site), Bacteroidetes (phylum; e.g., nose site), Bacteroidetes (phylum; e.g., skin site), Firmicutes (phylum; e.g., nose site), Fusobacteria (phylum; e.g., mouth site), Proteobacteria (phylum; e.g., mouth site), Actinobacteria (class; e.g., skin site), Bacteroidia (class; e.g., nose site), Bacteroidia (class; e.g., skin site), Clostridia (class; e.g., genital site), Flavobacteriia (class; e.g., nose site), Fusobacteriia (class; e.g., mouth site), Gammaproteobacteria (class; e.g., mouth site), Negativicutes (class; e.g., nose site), Actinomycetales (order; e.g., skin site), Bacteroidales (order; e.g., nose site), Bacteroidales (order; e.g., skin site), Clostridiales (order; e.g., genital site), Flavobacteriales (order; e.g., nose site), Fusobacteriales (order; e.g., mouth site), Pasteurellales (order; e.g., mouth site), Selenomonadales (order; e.g., nose site), Bacteroidaceae (family; e.g., genital site), Bacteroidaceae (family; e.g., nose site), Bacteroidaceae (family; e.g., skin site), Clostridiales Family XI. Incertae Sedis (family; e.g., mouth site), Corynebacteriaceae (family; e.g., mouth site), Flavobacteriaceae (family; e.g., nose site), Lachnospiraceae (family; e.g., genital site), Lachnospiraceae (family; e.g., nose site), Lachnospiraceae (family; e.g., skin site), Pasteurellaceae (family; e.g., mouth site), Propionibacteriaceae (family; e.g., skin site), Staphylococcaceae (family; e.g., skin site), Streptococcaceae (family; e.g., skin site), *Asaccharospora* (genus; e.g., gut site), *Bacteroides* (genus; e.g., genital site), *Bacteroides* (genus; e.g., nose site), *Bacteroides* (genus; e.g., skin site), *Blautia* (genus; e.g., genital site), *Capnocytophaga* (genus; e.g., mouth site), *Corynebacterium* (genus; e.g., mouth site), *Faecalibacterium* (genus; e.g., genital site), *Faecalibacterium* (genus; e.g., nose site), *Haemophilus* (genus; e.g., mouth site), *Propionibacterium* (genus; e.g., skin site), *Roseburia* (genus; e.g., genital site), *Roseburia* (genus; e.g., nose site), *Staphylococcus* (genus; e.g., skin site), *Streptococcus* (genus; e.g., skin site), *Anaerococcus* sp. 8404299 (species; e.g., genital site), *Asaccharospora irregularis* (species; e.g., gut site), *Bacteroides vulgatus* (species; e.g., genital site), *Bacteroides vulgatus* (species; e.g., nose site), *Bacteroides vulgatus* (species; e.g., skin site), *Blautia wexlerae* (species; e.g., genital site), *Faecalibacterium prausnitzii* (species; e.g., genital site), *Haemophilus influenzae* (species; e.g., mouth site), *Parabacteroides distasonis* (species; e.g., gut site), *Veillonella rogosae* (species; e.g., nose site), *Veillonella* sp. CM60 (species; e.g., nose site).

3.3.H Probiotics Condition Characterization Process.

In a variation, Block S130 can include performing a probiotics characterization process (e.g., determining and/or applying a probiotics characterization model; etc.) for one or more users.

In one implementation, a characterization process of Block S130 based upon statistical analyses can identify the sets of features that have the highest correlations with probiotics-associated-microorganisms (e.g., associated with food and diet) for which one or more therapies would have a positive effect, such as based upon a random forest predictor algorithm (and/or other suitable model) trained with a training dataset derived from a subset of the population of subjects, and/or validated with a validation dataset derived from a subset of the population of subjects. In particular, using probiotics-associated-microorganisms (e.g., a probiotics-related condition such as a probiotics consumption behavior condition) for different health conditions associated with foods and habits can include a set of eating disorders and/or diseases associated with nutrition of an individual characterized by medical history (e.g., medical interview), laboratory analysis (e.g., blood samples), physical analysis and measures (e.g., BMI). A set of features (e.g., useful for diagnostics and/or other suitable purposes, etc.) associated with using probiotics can include features associated with (e.g., derived from) at least one or more of the following taxons: *Blautia luti* (Species), *Flavonifractor plautii* (Species), *Collinsella aerofaciens* (Species), *Blautia glucerasea* (Species), *Erysipelatoclostridium ramosum* (Species), *Dialister propionicifaciens* (Species), *Blautia* sp. YHC-4 (Species), *Bifidobacterium* (Genus), *Oscillospira* (Genus), *Dialister* (Genus), *Intestinimonas* (Genus), *Moryella* (Genus), *Collinsella* (Genus), *Bacteroides* (Genus), *Finegoldia* (Genus), *Dorea* (Genus), *Peptoniphilus* (Genus), *Subdoligranulum* (Genus), *Anaerotruncus* (Genus), *Corynebacterium* (Genus), *Roseburia* (Genus), *Porphyromonas* (Genus), *Flavonifractor* (Genus), *Faecalibacterium* (Genus), *Lactobacillus* (Genus), *Anaerococcus* (Genus), *Pseudoflavonifractor* (Genus), *Phascolarctobacterium* (Genus), *Sarcina* (Genus), Bifidobacteriaceae (Family), Oscillospiraceae (Family), Bacteroidaceae (Family), Veillonellaceae (Family), Ruminococcaceae (Family), Lactobacillaceae (Family), Coriobacteriaceae (Family), Clostridiales Family XI. Incertae Sedis (Family), Streptococcaceae (Family), Corynebacteriaceae (Family), Prevotellaceae (Family), Flavobacteriaceae (Family), Bifidobacteriales (Order), Bacteroidales (Order), Clostridiales (Order), Coriobacteriales (Order), Actinomycetales (Order), Actinobacteria (Class), Bacteroidia (Class), Clostridia (Class), Actinobacteria (Phylum), Bacteroidetes (Phylum), Firmicutes (Phylum), Proteobacteria (Phylum), and/or at least one of or a combination of the followings functional features: Carbohydrate Metabolism (KEGG2), Metabolism (KEGG2), Translation (KEGG2), Transport and Catabolism (KEGG2), Cellular Processes and Signaling (KEGG2), Genetic Information Processing (KEGG2), Glycan Biosynthesis and Metabolism (KEGG2), Environmental Adaptation (KEGG2), Signaling Molecules and Interaction (KEGG2), Metabolism of Other Amino Acids (KEGG2), Replication and Repair (KEGG2), Neurodegenerative Diseases (KEGG2), Biosynthesis of Other Secondary Metabolites (KEGG2), Energy Metabolism (KEGG2), Enzyme Families (KEGG2), Cell Motility (KEGG2), Poorly Characterized (KEGG2), Nucleotide Metabolism (KEGG2), Metabolic Diseases (KEGG2), Amino Acid Metabolism (KEGG2), Ribosome Biogenesis (KEGG3), Amyotrophic lateral sclerosis (ALS) (KEGG3), Nitrogen metabolism (KEGG3), Aminoacyl-tRNA biosynthesis (KEGG3), Amino sugar and nucleotide sugar metabolism (KEGG3), Glycosaminoglycan degradation (KEGG3), Other glycan degradation (KEGG3), Inositol phosphate metabolism (KEGG3), Lysosome (KEGG3), Ascorbate and aldarate metabolism (KEGG3), Type II diabetes mellitus (KEGG3), Huntington's disease (KEGG3), Translation proteins (KEGG3), Peptidoglycan biosynthesis (KEGG3), Fructose and mannose metabolism (KEGG3), Glycosphingolipid biosynthesis—ganglio series (KEGG3), Nucleotide excision repair (KEGG3), Pentose and glucuronate interconversions (KEGG3), Nicotinate and nicotinamide metabolism (KEGG3), Pores ion channels (KEGG3), Biosynthesis and biodegradation of secondary metabolites (KEGG3), Glycosphingolipid biosynthesis—globo series (KEGG3), Ribosome biogenesis in eukaryotes (KEGG3), Membrane and intracellular structural molecules (KEGG3), Penicillin and cephalosporin biosynthesis (KEGG3), Other ion-coupled transporters (KEGG3), Glycerophospholipid metabolism (KEGG3), Polycyclic aromatic hydrocarbon degradation (KEGG3), Lipopolysaccharide biosynthesis proteins (KEGG3), Lipoic acid metabolism (KEGG3), Geraniol degradation (KEGG3), Cell motility and secretion (KEGG3), Glyoxylate and dicarboxylate metabolism (KEGG3), Plant-pathogen interaction (KEGG3), Amino acid related enzymes (KEGG3), Galactose metabolism (KEGG3), Ribosome (KEGG3), Taurine and hypotaurine metabolism (KEGG3), Toluene degradation (KEGG3), Sphingolipid metabolism (KEGG3), Terpenoid backbone biosynthesis (KEGG3), Insulin signaling pathway (KEGG3), Others (KEGG3), DNA repair and recombination proteins (KEGG3), Oxidative phosphorylation (KEGG3), Base excision repair (KEGG3), Chromosome (KEGG3), Replication, recombination and repair proteins (KEGG3), Cellular antigens (KEGG3), RNA polymerase (KEGG3), Pantothenate and CoA biosynthesis (KEGG3), Cytoskeleton proteins (KEGG3), Amino acid metabolism (KEGG3), Lipid metabolism (KEGG3), Carbon fixation pathways in prokaryotes (KEGG3), Ubiquinone and other terpenoid-quinone biosynthesis (KEGG3), Homologous recombination (KEGG3), Peroxisome (KEGG3), Tuberculosis (KEGG3), Thiamine metabolism (KEGG3), Citrate cycle (TCA cycle) (KEGG3), Other transporters (KEGG3), Phosphonate and phosphinate metabolism (KEGG3), Cyanoamino acid metabolism (KEGG3), Lipopolysaccharide biosynthesis (KEGG3), Phenylalanine metabolism (KEGG3), Mismatch repair (KEGG3), Signal transduction mechanisms (KEGG3), Secretion system (KEGG3), Cysteine and methionine metabolism (KEGG3), Bisphenol degradation (KEGG3), Energy metabolism (KEGG3), Proteasome (KEGG3), Aminobenzoate degradation (KEGG3), Butanoate metabolism (KEGG3), Pentose phosphate pathway (KEGG3), Purine metabolism (KEGG3), Tyrosine metabolism (KEGG3), Biosynthesis of unsaturated fatty acids (KEGG3), Bacterial motility proteins (KEGG3), Inorganic ion transport and metabolism (KEGG3), D-Alanine metabolism (KEGG3), Sulfur metabolism (KEGG3), Pyrimidine metabolism (KEGG3), Streptomycin biosynthesis (KEGG3), Translation factors (KEGG3), Lysine biosynthesis (KEGG3), Valine, leucine and isoleucine degradation (KEGG3), General function prediction only (KEGG3), Protein processing in endoplasmic reticulum (KEGG3), Carbon fixation in photosynthetic organisms (KEGG3), Phosphatidylinositol signaling system (KEGG3), Bacterial chemotaxis (KEGG3), Phenylpropanoid biosynthesis (KEGG3), ABC transporters (KEGG3), Phosphotransferase system (PTS) (KEGG3), Bacterial toxins (KEGG3), Pyruvate metabolism (KEGG3), Ubiquitin system (KEGG3), Carbohydrate metabolism (KEGG3), Phenylalanine, tyrosine and tryptophan biosynthesis (KEGG3), Epithelial cell signaling in *Helicobacter pylori* infection (KEGG3), Photosynthesis (KEGG3), Polyketide sugar unit biosynthesis (KEGG3), DNA replication (KEGG3), RNA degradation (KEGG3) and Peptidases (KEGG3).

Additionally or alternatively, microbiome features (e.g., microbiome composition diversity features) can include and/or otherwise be associated with (e.g., relative abundance for the taxons, etc.) one or more of the following taxons, such as in relation to a sample site (e.g., probiotics condition correlations with microorganisms observed at a particular sample site): Acidobacteria (phylum; e.g., gut site), Actinobacteria (phylum; e.g., gut site), Actinobacteria (phylum; e.g., gut site), Bacteroidetes (phylum; e.g., gut site), Bacteroidetes (phylum; e.g., gut site), Candidatus Saccharibacteria (phylum; e.g., gut site), Chloroflexi (phylum; e.g., gut site), Cyanobacteria (phylum; e.g., gut site), Cyanobacteria (phylum; e.g., skin site), Euryarchaeota (phylum; e.g., gut site), Firmicutes (phylum; e.g., gut site), Firmicutes (phylum; e.g., gut site), Lentisphaerae (phylum; e.g., gut site), Proteobacteria (phylum; e.g., gut site), Proteobacteria (phylum; e.g., gut site), Streptophyta (phylum; e.g., gut site), Streptophyta (phylum; e.g., nose site), Tenericutes (phylum; e.g., gut site), Tenericutes (phylum; e.g., gut site), Verrucomicrobia (phylum; e.g., gut site), Acidobacteriia (class; e.g., gut site), Acidobacteriia (class; e.g., mouth site), Actinobacteria (class; e.g., gut site), Actinobacteria (class; e.g., gut site), Alphaproteobacteria (class; e.g., gut site), Anaerolineae (class; e.g., gut site), Bacteroidia (class; e.g., gut site), Bacteroidia (class; e.g., gut site), Betaproteobacteria (class; e.g., gut site), Clostridia (class; e.g., gut site), Clostridia (class; e.g., gut site), Deltaproteobacteria (class; e.g., gut site), Deltaproteobacteria (class; e.g., gut site), Epsilonproteobacteria (class; e.g., gut site), Erysipelotrichia (class; e.g., gut site), Flavobacteriia (class; e.g., gut site), Gammaproteobacteria (class; e.g., gut site), Lentisphaeria (class; e.g., gut site), Methanobacteria (class; e.g., gut site), Mollicutes (class; e.g., gut site), Mollicutes (class; e.g., gut site), Negativicutes (class; e.g., gut site), Opitutae (class; e.g., gut site), Verrucomicrobiae (class; e.g., gut site), Acholeplasmatales (order; e.g., gut site), Actinomycetales (order; e.g., gut site), Anaerolineales (order; e.g., gut site), Bacillales (order; e.g., gut site), Bacteroidales (order; e.g., gut site), Bacteroidales (order; e.g., gut site), Bifidobacteriales (order; e.g., gut site), Bifidobacteriales (order; e.g., nose site), Burkholderiales (order; e.g., gut site), Campylobacterales (order; e.g., gut site), Clostridiales (order; e.g., gut site), Clostridiales (order; e.g., gut site), Coriobacteriales (order; e.g., gut site), Desulfovibrionales (order; e.g., gut site), Desulfovibrionales (order; e.g., gut site), Enterobacteriales (order; e.g., gut site), Erysipelotrichales (order; e.g., gut site), Flavobacteriales (order; e.g., gut site), Methanobacteriales (order; e.g., gut site), Mycoplasmatales (order; e.g., gut site), Puniceicoccales (order; e.g., gut site), Rhodospirillales (order; e.g., gut site), Selenomonadales (order; e.g., gut site), Solanales (order; e.g., gut site), Solanales (order; e.g., nose site), Verrucomicrobiales (order; e.g., gut site), Acholeplasmataceae (family; e.g., gut site), Acidaminococcaceae (family; e.g., gut site), Actinomycetaceae (family; e.g., gut site), Anaerolineaceae (family; e.g., gut site), Bacillaceae (family; e.g., gut site), Bacillaceae (family; e.g., nose site), Bacteroidaceae (family; e.g., gut site), Bacteroidaceae (family; e.g., gut site), Bifidobacteriaceae (family; e.g., gut site), Bifidobacteriaceae (family; e.g., nose site), Brevibacteriaceae (family; e.g., gut site), Brevibacteriaceae (family; e.g., mouth site), Brevibacteriaceae (family; e.g., skin site), Campylobacteraceae (family; e.g., gut site), Carnobacteriaceae (family; e.g., gut site), Carnobacteriaceae (family; e.g., mouth site), Clostridiaceae (family; e.g., gut site), Clostridiales Family XI. Incertae Sedis (family; e.g., gut site), Coriobacteriaceae (family; e.g., gut site), Corynebacteriaceae (family; e.g., gut site), Desulfovibrionaceae (family; e.g., gut site), Desulfovibrionaceae (family; e.g., gut site), Enterobacteriaceae (family; e.g., gut site), Enterococcaceae (family; e.g., gut site), Enterococcaceae (family; e.g., gut site), Erysipelotrichaceae (family; e.g., gut site), Eubacteriaceae (family; e.g., gut site), Flavobacteriaceae (family; e.g., gut site), Lachnospiraceae (family; e.g., gut site), Lactobacillaceae (family; e.g., gut site), Leuconostocaceae (family; e.g., nose site), Methanobacteriaceae (family; e.g., gut site), Microbacteriaceae (family; e.g., gut site), Moraxellaceae (family; e.g., mouth site), Mycoplasmataceae (family; e.g., gut site), Oscillospiraceae (family; e.g., gut site), Oscillospiraceae (family; e.g., gut site), Peptostreptococcaceae (family; e.g., gut site), Phyllobacteriaceae (family; e.g., gut site), Porphyromonadaceae (family; e.g., gut site), Prevotellaceae (family; e.g., gut site), Propionibacteriaceae (family; e.g., gut site), Propionibacteriaceae (family; e.g., gut site), Pseudomonadaceae (family; e.g., genital site), Rhodospirillaceae (family; e.g., gut site), Ruminococcaceae (family; e.g., gut site), Ruminococcaceae (family; e.g., gut site), Streptococcaceae (family; e.g., gut site), Sutterellaceae (family; e.g., gut site), Veillonellaceae (family; e.g., gut site), Verrucomicrobiaceae (family; e.g., gut site), Victivallaceae (family; e.g., gut site), *Abiotrophia* (genus; e.g., gut site), *Acholeplasma* (genus; e.g., gut site), *Acidaminococcus* (genus; e.g., gut site), *Adlercreutzia* (genus; e.g., gut site), *Adlercreutzia* (genus; e.g., gut site), *Akkermansia* (genus; e.g., gut site), *Allisonella* (genus; e.g., gut site), *Alloprevotella* (genus; e.g., genital site), *Anaerobacter* (genus; e.g., gut site), *Anaerococcus* (genus; e.g., gut site), *Anaerofilum* (genus; e.g., gut site), *Anaerofustis* (genus; e.g., gut site), *Anaerosporobacter* (genus; e.g., gut site), *Anaerotruncus* (genus; e.g., gut site), *Anaerotruncus* (genus; e.g., gut site), *Anaerovibrio* (genus; e.g., gut site), *Asteroleplasma* (genus; e.g., gut site), *Bacillus* (genus; e.g., gut site), *Bacteroides* (genus; e.g., gut site), *Bacteroides* (genus; e.g., gut site), *Barnesiella* (genus; e.g., gut site), *Barnesiella* (genus; e.g., gut site), *Bifidobacterium* (genus; e.g., gut site), *Bifidobacterium* (genus; e.g., gut site), *Bilophila* (genus; e.g., gut site), *Bilophila* (genus; e.g., gut site), *Brevibacterium* (genus; e.g., gut site), *Brevibacterium* (genus; e.g., mouth site), *Brevibacterium* (genus; e.g., skin site), *Butyricicoccus* (genus; e.g., gut site), *Butyricimonas* (genus; e.g., gut site), *Butyricimonas* (genus; e.g., gut site), *Campylobacter* (genus; e.g., gut site), *Candidatus Soleaferrea* (genus; e.g., gut site), *Citrobacter* (genus; e.g., gut site), *Collinsella* (genus; e.g., gut site), *Collinsella* (genus; e.g., gut site), *Coprobacillus* (genus; e.g., gut site), *Corynebacterium* (genus; e.g., gut site), *Desulfovibrio* (genus; e.g., gut site), *Dialister* (genus; e.g., gut site), *Dialister* (genus; e.g., gut site), *Dielma* (genus; e.g., gut site), *Dielma* (genus; e.g., gut site), *Dolosigranulum* (genus; e.g., skin site), *Dorea* (genus; e.g., gut site), *Dorea* (genus; e.g., gut site), *Dysgonomonas* (genus; e.g., gut site), *Eggerthella* (genus; e.g., gut site), *Eggerthella* (genus; e.g., gut site), *Eisenbergiella* (genus; e.g., gut site), *Eisenbergiella* (genus; e.g., gut site), *Enterobacter* (genus; e.g., genital site), *Enterobacter* (genus; e.g., gut site), *Enterobacter* (genus; e.g., gut site), *Enterococcus* (genus; e.g., gut site), *Enterococcus* (genus; e.g., gut site), *Enterorhabdus* (genus; e.g., gut site), *Erysipelatoclostridium* (genus; e.g., gut site), *Eubacterium* (genus; e.g., gut site), *Faecalibacterium* (genus; e.g., gut site), *Faecalibacterium* (genus; e.g., gut site), *Fastidiosipila* (genus; e.g., gut site), *Finegoldia* (genus; e.g., gut site), *Flavonifractor* (genus; e.g., gut site), *Fusicatenibacter* (genus; e.g., gut site), *Fusicatenibacter* (genus; e.g., gut site), *Gardnerella* (genus; e.g., skin site), *Gemella* (genus; e.g., gut site), *Gordonibacter* (genus; e.g., gut site), *Gordonibacter* (genus; e.g., gut site), *Granulicatella* (genus; e.g., mouth site), *Hespellia* (genus; e.g., gut site), *Hespellia* (genus; e.g., gut site), *Holdemania* (genus; e.g., gut site), *Holdemania* (genus; e.g., gut site), *Howardella* (genus; e.g., gut site), *Howardella* (genus; e.g., gut site), *Intestinibacter* (genus; e.g., gut site), *Intestinimonas* (genus; e.g., gut site), *Intestinimonas* (genus; e.g., gut site), *Klebsiella* (genus; e.g., gut site), *Lachnospira* (genus; e.g., gut site), *Lactobacillus* (genus; e.g., gut site), *Lactobacillus* (genus; e.g., gut site), *Lactococcus* (genus; e.g., gut site), *Lactonifactor* (genus; e.g., gut site), *Leuconostoc* (genus; e.g., nose site), *Marvinbryantia* (genus; e.g., gut site), *Megasphaera* (genus; e.g., gut site), *Megasphaera* (genus; e.g., gut site), *Methanobrevibacter* (genus; e.g., gut site), *Mitsuokella* (genus; e.g., gut site), *Mogibacterium* (genus; e.g., gut site), *Moraxella* (genus; e.g., nose site), *Moryella* (genus; e.g., gut site), *Moryella* (genus; e.g., gut site), *Murdochiella* (genus; e.g., gut site), *Odoribacter* (genus; e.g., gut site), *Odoribacter* (genus; e.g., gut site), *Oscillibacter* (genus; e.g., gut site), *Oscillospira* (genus; e.g., gut site), *Oscillospira* (genus; e.g., gut site), *Papillibacter* (genus; e.g., gut site), *Parabacteroides* (genus; e.g., gut site), *Parabacteroides* (genus; e.g., gut site), *Parasutterella* (genus; e.g., gut site), *Parvibacter* (genus; e.g., gut site), *Parvimonas* (genus; e.g., gut site), *Pasteurella* (genus; e.g., nose site), *Peptoniphilus* (genus; e.g., gut site), *Phascolarctobacterium* (genus; e.g., gut site), *Phascolarctobacterium* (genus; e.g., gut site), *Photobacterium* (genus; e.g., nose site), *Phyllobacterium* (genus; e.g., gut site), *Porphyromonas* (genus; e.g., gut site), *Prevotella* (genus; e.g., gut site), *Propionibacterium* (genus; e.g., genital site), *Propionibacterium* (genus; e.g., gut site), *Pseudoclavibacter* (genus; e.g., gut site), *Pseudoflavonifractor* (genus; e.g., gut site), *Pseudoflavonifractor* (genus; e.g., gut site), *Pseudomonas* (genus; e.g., genital site), *Psychrobacter* (genus; e.g., skin site), *Robinsoniella* (genus; e.g., gut site), *Robinsoniella* (genus; e.g., gut site), *Romboutsia* (genus; e.g., gut site), *Roseburia* (genus; e.g., gut site), *Roseburia* (genus; e.g., gut site), *Sarcina* (genus; e.g., gut site), *Sarcina* (genus; e.g., gut site), *Shuttleworthia* (genus; e.g., gut site), *Slackia* (genus; e.g., gut site), *Streptococcus* (genus; e.g., gut site), *Subdoligranulum* (genus; e.g., gut site), *Subdoligranulum* (genus; e.g., gut site), *Sutterella* (genus; e.g., gut site), *Sutterella* (genus; e.g., gut site), *Syntrophococcus* (genus; e.g., gut site), *Terrisporobacter* (genus; e.g., gut site), *Terrisporobacter* (genus; e.g., gut site), *Thalassospira* (genus; e.g., gut site), *Turicella* (genus; e.g., skin site), *Turicibacter* (genus; e.g., gut site), *Varibaculum* (genus; e.g., gut site), *Veillonella* (genus; e.g., gut site), *Victivallis* (genus; e.g., gut site), *Abiotrophia defectiva* (species; e.g., gut site), *Acidaminococcus fermentans* (species; e.g., gut site), *Acidaminococcus intestini* (species; e.g., gut site), *Acidaminococcus* sp. D21 (species; e.g., gut site), *Acinetobacter* sp. p-1 (species; e.g., nose site), *Adlercreutzia equolifaciens* (species; e.g., gut site), *Adlercreutzia equolifaciens* (species; e.g., gut site), *Akkermansia muciniphila* (species; e.g., gut site), *Alistipes finegoldii* (species; e.g., gut site), *Alistipes putredinis* (species; e.g., gut site), *Alistipes putredinis* (species; e.g., gut site), *Alistipes shahii* (species; e.g., gut site), *Alistipes* sp. HGB5 (species; e.g., gut site), *Alistipes* sp. NML05A004 (species; e.g., gut site), *Alistipes* sp. RMA 9912 (species; e.g., gut site), *Alistipes* sp. RMA 9912 (species; e.g., gut site), *Allisonella histaminiformans* (species; e.g., gut site), *Anaerococcus murdochii* (species; e.g., gut site), *Anaerococcus* sp. 8404299 (species; e.g., gut site), *Anaerococcus* sp. 9401487 (species; e.g., skin site), *Anaerococcus* sp. 9402080 (species; e.g., gut site), *Anaerococcus* sp. S9 PR-16 (species; e.g., genital site), *Anaerofustis stercorihominis* (species; e.g., gut site), *Anaerostipes butyraticus* (species; e.g., gut site), *Anaerostipes* sp. 3_2_56FAA (species; e.g., gut site), *Anaerostipes* sp. 3_2_56FAA (species; e.g., gut site), *Anaerostipes* sp. 494a (species; e.g., gut site), *Anaerostipes* sp. 5_1_63FAA (species; e.g., gut site), *Anaerostipes* sp. 5_1_63FAA (species; e.g., gut site), *Anaerotruncus colihominis* (species; e.g., gut site), *Anaerotruncus* sp. NML 070203 (species; e.g., gut site), *Arthrobacter* sp. (species; e.g., gut site), *Bacillus* sp. DHT-33 (species; e.g., gut site), *Bacteroides clarus* (species; e.g., gut site), *Bacteroides finegoldii* (species; e.g., gut site), *Bacteroides massiliensis* (species; e.g., gut site), *Bacteroides massiliensis* (species; e.g., gut site), *Bacteroides nordii* (species; e.g., gut site), *Bacteroides plebeius* (species; e.g., gut site), *Bacteroides plebeius* (species; e.g., gut site), *Bacteroides* sp. AR20 (species; e.g., gut site), *Bacteroides* sp. AR20 (species; e.g., gut site), *Bacteroides* sp. AR29 (species; e.g., gut site), *Bacteroides* sp. AR29 (species; e.g., gut site), *Bacteroides* sp. C13EG172 (species; e.g., gut site), *Bacteroides* sp. D22 (species; e.g., gut site), *Bacteroides* sp.

D22 (species; e.g., gut site), *Bacteroides* sp. EBA5-17 (species; e.g., gut site), *Bacteroides* sp. SLC1-38 (species; e.g., gut site), *Bacteroides* sp. XB12B (species; e.g., gut site), *Bacteroides* sp. XB12B (species; e.g., gut site), *Bacteroides stercoris* (species; e.g., gut site), *Bacteroides thetaiotaomicron* (species; e.g., gut site), *Bacteroides thetaiotaomicron* (species; e.g., nose site), *Bacteroides thetaiotaomicron* (species; e.g., gut site), *Bacteroides uniformis* (species; e.g., gut site), *Bacteroides vulgatus* (species; e.g., gut site), *Bacteroides vulgatus* (species; e.g., gut site), *Barnesiella intestinihominis* (species; e.g., gut site), *Barnesiella intestinihominis* (species; e.g., gut site), *Barnesiella* sp. 177 (species; e.g., gut site), *Barnesiella viscericola* (species; e.g., gut site), *Bifidobacterium adolescentis* (species; e.g., gut site), *Bifidobacterium animalis* (species; e.g., gut site), *Bifidobacterium choerinum* (species; e.g., gut site), *Bifidobacterium kashiwanohense* (species; e.g., gut site), *Bifidobacterium longum* (species; e.g., gut site), *Bifidobacterium merycicum* (species; e.g., gut site), *Bifidobacterium merycicum* (species; e.g., gut site), *Bifidobacterium pseudocatenulatum* (species; e.g., gut site), *Bifidobacterium* sp. (species; e.g., gut site), *Bifidobacterium stercoris* (species; e.g., gut site), *Bifidobacterium stercoris* (species; e.g., gut site), *Bifidobacterium tsurumiense* (species; e.g., gut site), *Bilophila* sp. 4_1_30 (species; e.g., gut site), *Bilophila wadsworthia* (species; e.g., gut site), *Blautia faecis* (species; e.g., gut site), *Blautia glucerasea* (species; e.g., gut site), *Blautia glucerasea* (species; e.g., skin site), *Blautia glucerasea* (species; e.g., gut site), *Blautia hydrogenotrophica* (species; e.g., gut site), *Blautia hydrogenotrophica* (species; e.g., gut site), *Blautia luti* (species; e.g., gut site), *Blautia luti* (species; e.g., gut site), *Blautia* sp. Ser8 (species; e.g., gut site), *Blautia* sp. Ser8 (species; e.g., gut site), *Blautia* sp. YHC-4 (species; e.g., gut site), *Blautia* sp. YHC-4 (species; e.g., gut site), *Blautia wexlerae* (species; e.g., gut site), *Brevibacterium paucivorans* (species; e.g., gut site), *Butyricicoccus pullicaecorum* (species; e.g., gut site), *Butyricimonas virosa* (species; e.g., gut site), *Butyrivibrio crossotus* (species; e.g., gut site), *Campylobacter hominis* (species; e.g., gut site), *Catenibacterium mitsuokai* (species; e.g., gut site), *Citrobacter* sp. BW4 (species; e.g., gut site), *Collinsella aerofaciens* (species; e.g., gut site), *Collinsella aerofaciens* (species; e.g., gut site), *Collinsella intestinalis* (species; e.g., gut site), *Coprobacillus* sp. D6 (species; e.g., gut site), *Corynebacterium canis* (species; e.g., gut site), *Corynebacterium epidermidicanis* (species; e.g., gut site), *Corynebacterium epidermidicanis* (species; e.g., mouth site), *Corynebacterium freiburgense* (species; e.g., mouth site), *Corynebacterium mastitidis* (species; e.g., gut site), *Corynebacterium ulcerans* (species; e.g., skin site), *Desulfovibrio piger* (species; e.g., gut site), *Dialister invisus* (species; e.g., gut site), *Dialister micraerophilus* (species; e.g., mouth site), *Dialister propionicifaciens* (species; e.g., gut site), *Dialister* sp. S4-23 (species; e.g., gut site), *Dialister succinatiphilus* (species; e.g., gut site), *Dielma fastidiosa* (species; e.g., gut site), *Dielma fastidiosa* (species; e.g., gut site), *Dolosigranulum pigrum* (species; e.g., skin site), *Dorea formicigenerans* (species; e.g., gut site), *Dorea formicigenerans* (species; e.g., gut site), *Dorea longicatena* (species; e.g., gut site), *Dorea longicatena* (species; e.g., gut site), *Dysgonomonas capnocytophagoides* (species; e.g., gut site), *Dysgonomonas oryzarvi* (species; e.g., gut site), *Eggerthella sinensis* (species; e.g., gut site), *Eggerthella* sp. HGA1 (species; e.g., gut site), *Eggerthella* sp. HGA1 (species; e.g., gut site), *Eisenbergiella tayi* (species; e.g., gut site), *Eisenbergiella tayi* (species; e.g., gut site), *Enterobacter* sp. BS2-1 (species; e.g., genital site), *Enterobacter* sp. BS2-1 (species; e.g., gut site), *Enterococcus* sp. C6I11 (species; e.g., gut site), *Enterococcus* sp. SI-4 (species; e.g., gut site), *Enterococcus ureasiticus* (species; e.g., mouth site), *Erysipelatoclostridium ramosum* (species; e.g., gut site), *Erysipelatoclostridium ramosum* (species; e.g., gut site), *Eubacterium callanderi* (species; e.g., gut site), *Eubacterium* sp. SA11 (species; e.g., gut site), *Facklamia languida* (species; e.g., gut site), *Faecalibacterium prausnitzii* (species; e.g., gut site), *Faecalibacterium prausnitzii* (species; e.g., gut site), *Faecalibacterium* sp. canine oral taxon 147 (species; e.g., gut site), *Finegoldia* sp. S8 F7 (species; e.g., genital site), *Finegoldia* sp. S9 AA1-5 (species; e.g., gut site), *Flavonifractor plautii* (species; e.g., gut site), *Flavonifractor plautii* (species; e.g., gut site), *Fusicatenibacter saccharivorans* (species; e.g., gut site), *Fusicatenibacter saccharivorans* (species; e.g., gut site), *Fusobacterium mortiferum* (species; e.g., gut site), *Fusobacterium* sp. CM21 (species; e.g., gut site), *Fusobacterium varium* (species; e.g., gut site), *Gardnerella vaginalis* (species; e.g., skin site), *Gemella morbillorum* (species; e.g., gut site), *Gemella sanguinis* (species; e.g., mouth site), *Gemella* sp. 933-88 (species; e.g., gut site), *Gemella* sp. 933-88 (species; e.g., gut site), *Gordonibacter pamelaeae* (species; e.g., gut site), *Gordonibacter pamelaeae* (species; e.g., gut site), *Granulicatella adiacens* (species; e.g., mouth site), *Haemophilus influenzae* (species; e.g., gut site), *Holdemania filiformis* (species; e.g., gut site), *Holdemania filiformis* (species; e.g., gut site), *Howardella ureilytica* (species; e.g., gut site), *Howardella ureilytica* (species; e.g., gut site), *Intestinimonas butyriciproducens* (species; e.g., gut site), *Klebsiella* sp. SOR89 (species; e.g., gut site), *Lachnospira pectinoschiza* (species; e.g., gut site), *Lachnospira pectinoschiza* (species; e.g., gut site), *Lactobacillus crispatus* (species; e.g., gut site), *Lactobacillus crispatus* (species; e.g., gut site), *Lactobacillus delbrueckii* (species; e.g., gut site), *Lactobacillus fornicalis* (species; e.g., mouth site), *Lactobacillus plantarum* (species; e.g., gut site), *Lactobacillus rhamnosus* (species; e.g., gut site), *Lactobacillus ruminis* (species; e.g., gut site), *Lactobacillus ruminis* (species; e.g., gut site), *Lactobacillus salivarius* (species; e.g., gut site), *Lactobacillus* sp. 7_1_47FAA (species; e.g., genital site), *Lactobacillus* sp. 7_1_47FAA (species; e.g., mouth site), *Lactobacillus* sp. 7_1_47FAA (species; e.g., nose site), *Lactobacillus* sp. 7_1_47FAA (species; e.g., gut site), *Lactobacillus* sp. BL302 (species; e.g., gut site), *Lactobacillus* sp. S16 (species; e.g., nose site), *Lactobacillus* sp. TAB-22 (species; e.g., gut site), *Lactobacillus* sp. TAB-26 (species; e.g., gut site), *Lactobacillus* sp. TAB-30 (species; e.g., gut site), *Lactococcus* sp. MH5-2 (species; e.g., gut site), *Lactonifactor longoviformis* (species; e.g., gut site), *Lactonifactor longoviformis* (species; e.g., gut site), *Leuconostoc* sp. C714 (species; e.g., nose site), *Megasphaera elsdenii* (species; e.g., gut site), *Megasphaera* sp. S6-MB2 (species; e.g., gut site), *Methanobrevibacter smithii* (species; e.g., gut site), *Mitsuokella* sp. TM-10 (species; e.g., gut site), *Moraxella* sp. BB37 (species; e.g., nose site), *Moraxella* sp. BBN2P-02d (species; e.g., skin site), *Murdochiella asaccharolytica* (species; e.g., gut site), *Neisseria macacae* (species; e.g., genital site), *Neisseria mucosa* (species; e.g., gut site), *Neisseria mucosa* (species; e.g., skin site), *Odoribacter splanchnicus* (species; e.g., gut site), *Odoribacter splanchnicus* (species; e.g., gut site), *Parabacteroides distasonis* (species; e.g., gut site), *Parabacteroides goldsteinii* (species; e.g., skin site), *Parabacteroides merdae* (species; e.g., gut site), *Parabacteroides merdae* (species; e.g., gut site), *Parasutterella excrementihominis* (species; e.g., gut site), *Parvibacter caecicola* (species; e.g., gut site), *Parvimonas* sp. oral taxon 393 (species; e.g., gut site), *Pasteurella pneumotropica* (species; e.g., nose site), *Pediococcus* sp. MFC1 (species; e.g., gut site), *Peptococcus niger* (species; e.g., gut site), *Peptoniphilus* sp. 2002-2300004 (species; e.g., gut site), *Peptoniphilus* sp. gpac018A (species; e.g., gut site), *Peptoniphilus* sp. oral taxon 836 (species; e.g., gut site), *Phascolarctobacterium faecium* (species; e.g., gut site), *Phascolarctobacterium faecium* (species; e.g., gut site), *Photobacterium* sp. CAIM 866 (species; e.g., nose site), *Porphyromonas bennonis* (species; e.g., gut site), *Porphyromonas* sp. 2026 (species; e.g., gut site), *Porphyromonas* sp. 2026 (species; e.g., gut site), *Prevotella bivia* (species; e.g., gut site), *Prevotella buccalis* (species; e.g., gut site), *Prevotella disiens* (species; e.g., gut site), *Prevotella oris* (species; e.g., nose site), *Prevotella* sp. BV3C7 (species; e.g., gut site), *Prevotella timonensis* (species; e.g., gut site), *Pseudoclavibacter bifida* (species; e.g., gut site), *Pseudoclavibacter* sp. Timone (species; e.g., gut site), *Pseudoflavonifractor capillosus* (species; e.g., gut site), *Pseudoflavonifractor capillosus* (species; e.g., gut site), *Robinsoniella peoriensis* (species; e.g., gut site), *Roseburia faecis* (species; e.g., gut site), *Roseburia faecis* (species; e.g., gut site), *Roseburia hominis* (species; e.g., gut site), *Roseburia intestinalis* (species; e.g., gut site), *Roseburia inulinivorans* (species; e.g., gut site), *Roseburia inulinivorans* (species; e.g., gut site), *Roseburia* sp. 11SE39 (species; e.g., gut site), *Roseburia* sp. 11SE39 (species; e.g., gut site), *Roseburia* sp. 499 (species; e.g., gut site), *Slackia* sp. NATTS (species; e.g., gut site), *Slackia* sp. NATTS (species; e.g., gut site), *Staphylococcus* sp. WB18-16 (species; e.g., skin site), *Streptococcus equinus* (species; e.g., gut site), *Streptococcus* sp. 2011_Oral_MS_A3 (species; e.g., genital site), *Streptococcus* sp. 2011_Oral_MS_A3 (species; e.g., gut site), *Streptococcus* sp. oral taxon G59 (species; e.g., genital site), *Streptococcus* sp. oral taxon G63 (species; e.g., skin site), *Streptococcus thermophilus* (species; e.g., gut site), *Streptococcus thermophilus* (species; e.g., gut site), *Subdoligranulum variabile* (species; e.g., gut site), *Subdoligranulum variabile* (species; e.g., gut site), *Sutterella* sp. 252 (species; e.g., gut site), *Sutterella wadsworthensis* (species; e.g., gut site), *Turicella otitidis* (species; e.g., skin site), *Turicibacter sanguinis* (species; e.g., gut site), *Varibaculum cambriense* (species; e.g., gut site), *Veillonella* sp. 2011_Oral_VSA_D3 (species; e.g., mouth site), *Veillonella* sp. AS16 (species; e.g., gut site), *Veillonella* sp. CM60 (species; e.g., gut site).

3.3.I Lyme Disease Characterization Process.

In a variation, Block S130 can include performing a Lyme disease characterization process (e.g., determining and/or applying a Lyme disease characterization model; etc.) for one or more users.

In one implementation, a characterization process of Block S130 based upon statistical analyses can identify the sets of features that have the highest correlations with Lyme disease associated-microorganisms for which one or more therapies would have a positive effect, such as based upon a random forest predictor algorithm (and/or other suitable model) trained with a training dataset derived from a subset of the population of subjects, and/or validated with a validation dataset derived from a subset of the population of subjects. In particular, a Lyme disease condition can include an infectious disease caused by bacteria of the *Borrelia* genus that is transmitted by ticks of the *Ixodes* genus. A Lyme disease condition can be characterized by skin rashes starting at the tick's bite site and physical and mental unwellness, including fever, headaches and feeling tired. If untreated, symptoms may include memory problems, heart palpitations, reduced ability to move one or both sides of the face, joint pains and/or severe headaches with neck stiffness. Typical methods for diagnosis include analysis of symptoms, history of tick exposure and possible testing for the presence of specific antibodies, although this often shows false negatives in early stages of the disease. A set of features (e.g., useful for diagnostics and/or other suitable purposes, etc.) associated with Lyme disease includes features associated with (e.g., derived from) one or more of the following taxons: *Blautia luti* (Species), *Parabacteroides merdae* (Species), *Dorea* (Genus), *Subdoligranulum* (Genus), *Collinsella* (Genus), *Parabacteroides* (Genus), *Sarcina* (Genus), *Roseburia* (Genus), *Oscillospira* (Genus), *Bacteroides* (Genus), *Clostridium* (Genus), Oscillospiraceae (Family), Coriobacteriaceae (Family), Bacteroidaceae (Family), Ruminococcaceae (Family), Lactobacillaceae (Family), Fibrobacteraceae (Family), Clostridiaceae (Family), Porphyromonadaceae (Family), Coriobacteriales (Order), Bacteroidales (Order), Clostridiales (Order), Fibrobacterales (Order), Actinobacteria (Class), Bacteroidia (Class), Clostridia (Class), Fibrobacteria (Class), Actinobacteria (Phylum), Bacteroidetes (Phylum), Firmicutes (Phylum), Fibrobacteres (Phylum), and/or the microbiome features can additionally or alternatively include functional features (e.g., functional diversity features, etc.) including at least one or more of the followings: Metabolism (KEGG2), Carbohydrate Metabolism (KEGG2), Translation (KEGG2), Transport and Catabolism (KEGG2), Environmental Adaptation (KEGG2), Glycan Biosynthesis and Metabolism (KEGG2), Signaling Molecules and Interaction (KEGG2), Genetic Information Processing (KEGG2), Lipid Metabolism (KEGG2), Cellular Processes and Signaling (KEGG2), Neurodegenerative Diseases (KEGG2), Biosynthesis of Other Secondary Metabolites (KEGG2), Metabolism of Cofactors and Vitamins (KEGG2), Metabolism of Other Amino Acids (KEGG2), Enzyme Families (KEGG2), Nucleotide Metabolism (KEGG2), Replication and Repair (KEGG2), Pentose and glucuronate interconversions (KEGG3), Ascorbate and aldarate metabolism (KEGG3), MAPK signaling pathway—yeast (KEGG3), Ribosome Biogenesis (KEGG3), Fructose and mannose metabolism (KEGG3), Lipoic acid metabolism (KEGG3), Bisphenol degradation (KEGG3), Huntington's disease (KEGG3), Phosphonate and phosphinate metabolism (KEGG3), Translation proteins (KEGG3), Other glycan degradation (KEGG3), Sphingolipid metabolism (KEGG3), Inorganic ion transport and metabolism (KEGG3), Plant-pathogen interaction (KEGG3), Lysosome (KEGG3), Others (KEGG3), Ribosome biogenesis in eukaryotes (KEGG3), Carbohydrate metabolism (KEGG3), Glycosphingolipid biosynthesis—globo series (KEGG3), Amino acid metabolism (KEGG3), Amino acid related enzymes (KEGG3), Glycosaminoglycan degradation (KEGG3), Peptidoglycan biosynthesis (KEGG3), Thiamine metabolism (KEGG3), Galactose metabolism (KEGG3), RNA polymerase (KEGG3), Phosphatidylinositol signaling system (KEGG3), Ion channels (KEGG3), Inositol phosphate metabolism (KEGG3), Aminoacyl-tRNA biosynthesis (KEGG3), Cyanoamino acid metabolism (KEGG3), Terpenoid backbone biosynthesis (KEGG3), Phenylpropanoid biosynthesis (KEGG3), Membrane and intracellular structural molecules (KEGG3), Lipopolysaccharide biosynthesis proteins (KEGG3), Taurine and hypotaurine metabolism (KEGG3), Amino sugar and nucleotide sugar metabolism (KEGG3), D-Alanine metabolism (KEGG3), Penicillin and cephalosporin biosynthesis (KEGG3), Cell motility and secretion (KEGG3), Glyoxylate and dicarboxylate metabolism (KEGG3), Other transporters (KEGG3), Chromosome (KEGG3), Other ion-coupled transporters (KEGG3), Pores ion channels (KEGG3), Pentose phosphate pathway (KEGG3), Toluene degradation (KEGG3), Signal transduction mechanisms (KEGG3), Biosynthesis and biodegradation of secondary metabolites (KEGG3), Cysteine and methionine metabolism (KEGG3), Photosynthesis proteins (KEGG3), Glycosphingolipid biosynthesis—ganglio series (KEGG3), Photosynthesis (KEGG3), Replication, recombination and repair proteins (KEGG3), Pantothenate and CoA biosynthesis (KEGG3), Ubiquinone and other terpenoid-quinone biosynthesis (KEGG3), Ribosome (KEGG3), Geraniol degradation (KEGG3), Energy metabolism (KEGG3), Phenylalanine metabolism (KEGG3), Bacterial chemotaxis (KEGG3), Bacterial toxins (KEGG3), Limonene and pinene degradation (KEGG3), DNA repair and recombination proteins (KEGG3), Peroxisome (KEGG3), Nucleotide excision repair (KEGG3), Citrate cycle (TCA cycle) (KEGG3), Type II diabetes mellitus (KEGG3).

Additionally or alternatively, microbiome features (e.g., microbiome composition diversity features) can include and/or otherwise be associated with (e.g., relative abundance for the taxons, etc.) one or more of the following taxons, such as in relation to a sample site (e.g., Lyme disease condition correlations with microorganisms observed at a particular sample site): Actinobacteria (phylum; e.g., gut site), Actinobacteria (phylum; e.g., gut site), Bacteroidetes (phylum; e.g., gut site), Bacteroidetes (phylum; e.g., gut site), Euryarchaeota (phylum; e.g., gut site), Euryarchaeota (phylum; e.g., gut site), Firmicutes (phylum; e.g., gut site), Firmicutes (phylum; e.g., gut site), Fusobacteria (phylum; e.g., gut site), Fusobacteria (phylum; e.g., gut site), Tenericutes (phylum; e.g., gut site), Verrucomicrobia (phylum; e.g., gut site), Actinobacteria (class; e.g., gut site), Actinobacteria (class; e.g., gut site), Bacteroidia (class; e.g., gut site), Bacteroidia (class; e.g., gut site), Clostridia (class; e.g., gut site), Clostridia (class; e.g., gut site), Deltaproteobacteria (class; e.g., gut site), Deltaproteobacteria (class; e.g., gut site), Flavobacteriia (class; e.g., gut site), Flavobacteriia (class; e.g., gut site), Fusobacteriia (class; e.g., gut site), Fusobacteriia (class; e.g., gut site), Methanobacteria (class; e.g., gut site), Methanobacteria (class; e.g., gut site), Mollicutes (class; e.g., gut site), Negativicutes (class; e.g., gut site), Verrucomicrobiae (class; e.g., gut site), Anaeroplasmatales (order; e.g., gut site), Bacillales (order; e.g., gut site), Bacillales (order; e.g., gut site), Bacteroidales (order; e.g., gut site), Bacteroidales (order; e.g., gut site), Bifidobacteriales (order; e.g., gut site), Bifidobacteriales (order; e.g., gut site), Burkholderiales (order; e.g., gut site), Clostridiales (order; e.g., gut site), Clostridiales (order; e.g., gut site), Coriobacteriales (order; e.g., gut site), Coriobacteriales (order; e.g., gut site), Desulfovibrionales (order; e.g., gut site), Desulfovibrionales (order; e.g., gut site), Enterobacteriales (order; e.g., genital site), Enterobacteriales (order; e.g., gut site), Enterobacteriales (order; e.g., gut site), Flavobacteriales (order; e.g., gut site), Flavobacteriales (order; e.g., gut site), Fusobacteriales (order; e.g., gut site), Fusobacteriales (order; e.g., gut site), Methanobacteriales (order; e.g., gut site), Methanobacteriales (order; e.g., gut site), Rhizobiales (order; e.g., gut site), Rhodospirillales (order; e.g., gut site), Selenomonadales (order; e.g., gut site), Thermoanaerobacterales (order; e.g., gut site), Verrucomicrobiales (order; e.g., gut site), Acidaminococcaceae (family; e.g., gut site), Acidaminococcaceae (family; e.g., gut site), Anaeroplasmataceae (family; e.g., gut site), Bacillaceae (family; e.g., gut site), Bacteroidaceae (family; e.g., gut site), Bacteroidaceae (family; e.g., gut site), Bifidobacteriaceae (family; e.g., gut site), Bifidobacteriaceae (family; e.g., gut site), Carnobacteriaceae (family; e.g., gut site), Carnobacteriaceae (family; e.g., mouth site), Catabacteriaceae (family; e.g., gut site), Clostridiaceae (family; e.g., gut site), Clostridiaceae (family; e.g., gut site), Clostridiales Family XIII. Incertae Sedis (family; e.g., gut site), Coriobacteriaceae (family; e.g., gut site), Coriobacteriaceae (family; e.g., gut site), Desulfovibrionaceae (family; e.g., gut site), Desulfovibrionaceae (family; e.g., gut site), Enterobacteriaceae (family; e.g., genital site), Enterobacteriaceae (family; e.g., gut site), Enterobacteriaceae (family; e.g., gut site), Enterococcaceae (family; e.g., gut site), Enterococcaceae (family; e.g., gut site), Eubacteriaceae (family; e.g., gut site), Eubacteriaceae (family; e.g., gut site), Flavobacteriaceae (family; e.g., gut site), Flavobacteriaceae (family; e.g., gut site), Fusobacteriaceae (family; e.g., gut site), Lachnospiraceae (family; e.g., genital site), Lactobacillaceae (family; e.g., gut site), Lactobacillaceae (family; e.g., gut site), Leptotrichiaceae (family; e.g., gut site), Leptotrichiaceae (family; e.g., gut site), Leuconostocaceae (family; e.g., gut site), Methanobacteriaceae (family; e.g., gut site), Methanobacteriaceae (family; e.g., gut site), Micrococcaceae (family; e.g., gut site), Oscillospiraceae (family; e.g., gut site), Oscillospiraceae (family; e.g., gut site), Porphyromonadaceae (family; e.g., gut site), Porphyromonadaceae (family; e.g., gut site), Rhodospirillaceae (family; e.g., gut site), Rikenellaceae (family; e.g., gut site), Ruminococcaceae (family; e.g., gut site), Ruminococcaceae (family; e.g., mouth site), Ruminococcaceae (family; e.g., gut site), Streptococcaceae (family; e.g., gut site), Sutterellaceae (family; e.g., gut site), Sutterellaceae (family; e.g., gut site), Thermoanaerobacteraceae (family; e.g., gut site), Veillonellaceae (family; e.g., gut site), Verrucomicrobiaceae (family; e.g., gut site), *Actinobacillus* (genus; e.g., gut site), *Actinomyces* (genus; e.g., gut site), *Actinomyces* (genus; e.g., gut site), *Adlercreutzia* (genus; e.g., gut site), *Akkermansia* (genus; e.g., gut site), *Alistipes* (genus; e.g., gut site), *Anaerofilum* (genus; e.g., gut site), *Anaerofilum* (genus; e.g., gut site), *Anaerofustis* (genus; e.g., gut site), *Anaerotruncus* (genus; e.g., gut site), *Bacillus* (genus; e.g., gut site), *Bacteroides* (genus; e.g., gut site), *Bacteroides* (genus; e.g., gut site), *Barnesiella* (genus; e.g., gut site), *Barnesiella* (genus; e.g., gut site), *Bifidobacterium* (genus; e.g., gut site), *Bifidobacterium* (genus; e.g., gut site), *Bilophila* (genus; e.g., gut site), *Bilophila* (genus; e.g., gut site), *Butyricicoccus* (genus; e.g., gut site), *Butyricicoccus* (genus; e.g., gut site), *Butyricimonas* (genus; e.g., gut site), *Candidatus Soleaferrea* (genus; e.g., gut site), *Candidatus Soleaferrea* (genus; e.g., gut site), *Catabacter* (genus; e.g., gut site), *Citrobacter* (genus; e.g., gut site), *Citrobacter* (genus; e.g., gut site), *Clostridium* (genus; e.g., gut site), *Clostridium* (genus; e.g., gut site), *Collinsella* (genus; e.g., gut site), *Collinsella* (genus; e.g., gut site), *Coprobacillus* (genus; e.g., gut site), *Coprobacillus* (genus; e.g., gut site), *Coprobacter* (genus; e.g., gut site), *Dialister* (genus; e.g., gut site), *Dielma* (genus; e.g., gut site), *Dielma* (genus; e.g., gut site), *Dorea* (genus; e.g., gut site), *Dorea* (genus; e.g., gut site), *Eggerthella* (genus; e.g., gut site), *Eggerthella* (genus; e.g., gut site), *Eisenbergiella* (genus; e.g., gut site), *Eisenbergiella* (genus; e.g., gut site), *Enterococcus* (genus; e.g., gut site), *Enterococcus* (genus; e.g., gut site), *Enterorhabdus* (genus; e.g., gut site), *Eubacterium* (genus; e.g., gut site), *Eubacterium* (genus; e.g., gut site), *Faecalibacterium* (genus; e.g., gut site), *Faecalibacterium* (genus; e.g., mouth site), *Faecalibacterium* (genus; e.g., gut site), *Flavonifractor* (genus; e.g., gut site), *Flavonifractor* (genus; e.g., gut site), *Fusicatenibacter* (genus; e.g., gut site), *Fusicatenibacter* (genus; e.g., gut site), *Fusobacterium* (genus; e.g., gut site), *Gelria* (genus; e.g., gut site),

*Gordonibacter* (genus; e.g., gut site), *Gordonibacter* (genus; e.g., gut site), *Granulicatella* (genus; e.g., gut site), *Haemophilus* (genus; e.g., skin site), *Helcococcus* (genus; e.g., gut site), *Hespellia* (genus; e.g., gut site), *Hespellia* (genus; e.g., gut site), *Holdemania* (genus; e.g., gut site), *Holdemania* (genus; e.g., gut site), *Howardella* (genus; e.g., gut site), *Intestinimonas* (genus; e.g., gut site), *Kluyvera* (genus; e.g., genital site), *Lachnospira* (genus; e.g., gut site), *Lachnospira* (genus; e.g., gut site), *Lactobacillus* (genus; e.g., gut site), *Lactobacillus* (genus; e.g., gut site), *Lactonifactor* (genus; e.g., gut site), *Lactonifactor* (genus; e.g., gut site), *Marvinbryantia* (genus; e.g., gut site), *Megasphaera* (genus; e.g., gut site), *Megasphaera* (genus; e.g., gut site), *Methanobrevibacter* (genus; e.g., gut site), *Methanobrevibacter* (genus; e.g., gut site), *Moryella* (genus; e.g., gut site), *Moryella* (genus; e.g., gut site), *Odoribacter* (genus; e.g., gut site), *Oscillibacter* (genus; e.g., gut site), *Oscillospira* (genus; e.g., gut site), *Oscillospira* (genus; e.g., gut site), *Parabacteroides* (genus; e.g., gut site), *Parabacteroides* (genus; e.g., gut site), *Parasutterella* (genus; e.g., gut site), *Parvimonas* (genus; e.g., gut site), *Parvimonas* (genus; e.g., gut site), *Phascolarctobacterium* (genus; e.g., gut site), *Pseudoflavonifractor* (genus; e.g., gut site), *Pseudoflavonifractor* (genus; e.g., gut site), *Pseudomonas* (genus; e.g., skin site), *Robinsoniella* (genus; e.g., gut site), *Romboutsia* (genus; e.g., gut site), *Roseburia* (genus; e.g., gut site), *Roseburia* (genus; e.g., gut site), *Sarcina* (genus; e.g., gut site), *Sarcina* (genus; e.g., gut site), *Shuttleworthia* (genus; e.g., gut site), *Shuttleworthia* (genus; e.g., gut site), *Subdoligranulum* (genus; e.g., gut site), *Subdoligranulum* (genus; e.g., gut site), *Sutterella* (genus; e.g., gut site), *Sutterella* (genus; e.g., gut site), *Syntrophococcus* (genus; e.g., gut site), *Terrisporobacter* (genus; e.g., gut site), *Thalassospira* (genus; e.g., gut site), *Actinobacillus porcinus* (species; e.g., gut site), *Actinomyces* sp. ICM54 (species; e.g., gut site), *Adlercreutzia equolifaciens* (species; e.g., gut site), *Akkermansia muciniphila* (species; e.g., gut site), *Alistipes finegoldii* (species; e.g., gut site), *Alistipes putredinis* (species; e.g., gut site), *Alistipes* sp. EBA6-25cl2 (species; e.g., gut site), *Alistipes* sp. NML05A004 (species; e.g., gut site), *Alistipes* sp. RMA 9912 (species; e.g., gut site), *Anaerococcus vaginalis* (species; e.g., gut site), *Anaerofustis stercorihominis* (species; e.g., gut site), *Anaerosporobacter mobilis* (species; e.g., gut site), *Anaerostipes* sp. 3_2_56FAA (species; e.g., gut site), *Anaerostipes* sp. 3_2_56FAA (species; e.g., gut site), *Anaerostipes* sp. 494a (species; e.g., gut site), *Anaerostipes* sp. 494a (species; e.g., gut site), *Anaerostipes* sp. 5_1_63FAA (species; e.g., gut site), *Anaerostipes* sp. 5_1_63FAA (species; e.g., gut site), *Anaerotruncus colihominis* (species; e.g., gut site), *Anaerotruncus colihominis* (species; e.g., gut site), *Bacteroides acidifaciens* (species; e.g., gut site), *Bacteroides caccae* (species; e.g., gut site), *Bacteroides finegoldii* (species; e.g., gut site), *Bacteroides finegoldii* (species; e.g., gut site), *Bacteroides fragilis* (species; e.g., gut site), *Bacteroides massiliensis* (species; e.g., gut site), *Bacteroides ovatus* (species; e.g., gut site), *Bacteroides* sp. AR20 (species; e.g., gut site), *Bacteroides* sp. AR20 (species; e.g., gut site), *Bacteroides* sp. AR29 (species; e.g., gut site), *Bacteroides* sp. AR29 (species; e.g., gut site), *Bacteroides* sp. D22 (species; e.g., gut site), *Bacteroides* sp. EBA5-17 (species; e.g., gut site), *Bacteroides* sp. SLC1-38 (species; e.g., gut site), *Bacteroides* sp. XB12B (species; e.g., gut site), *Bacteroides stercoris* (species; e.g., gut site), *Bacteroides thetaiotaomicron* (species; e.g., gut site), *Bacteroides thetaiotaomicron* (species; e.g., gut site), *Bacteroides uniformis* (species; e.g., gut site), *Bacteroides vulgatus* (species; e.g., genital site), *Bacteroides vulgatus* (species; e.g., gut site), *Bacteroides vulgatus* (species; e.g., gut site), *Barnesiella intestinihominis* (species; e.g., gut site), *Barnesiella intestinihominis* (species; e.g., gut site), *Bifidobacterium kashiwanohense* (species; e.g., gut site), *Bifidobacterium longum* (species; e.g., gut site), *Bifidobacterium stercoris* (species; e.g., gut site), *Bifidobacterium stercoris* (species; e.g., gut site), *Bilophila* sp. 4_1_30 (species; e.g., gut site), *Bilophila wadsworthia* (species; e.g., gut site), *Blautia faecis* (species; e.g., gut site), *Blautia faecis* (species; e.g., gut site), *Blautia glucerasea* (species; e.g., gut site), *Blautia glucerasea* (species; e.g., gut site), *Blautia luti* (species; e.g., gut site), *Blautia luti* (species; e.g., gut site), *Blautia producta* (species; e.g., gut site), *Blautia producta* (species; e.g., gut site), *Blautia* sp. Ser8 (species; e.g., gut site), *Blautia* sp. Ser8 (species; e.g., gut site), *Blautia* sp. YHC-4 (species; e.g., gut site), *Blautia* sp. YHC-4 (species; e.g., gut site), *Blautia stercoris* (species; e.g., gut site), *Blautia stercoris* (species; e.g., gut site), *Blautia wexlerae* (species; e.g., gut site), *Blautia wexlerae* (species; e.g., gut site), *Butyricicoccus pullicaecorum* (species; e.g., gut site), *Butyricicoccus pullicaecorum* (species; e.g., gut site), *Butyrivibrio crossotus* (species; e.g., gut site), *Collinsella aerofaciens* (species; e.g., gut site), *Collinsella aerofaciens* (species; e.g., gut site), *Coprobacillus* sp. D6 (species; e.g., gut site), *Coprobacillus* sp. D6 (species; e.g., gut site), *Coprobacter fastidiosus* (species; e.g., gut site), *Corynebacterium canis* (species; e.g., gut site), *Desulfovibrio piger* (species; e.g., gut site), *Desulfovibrio piger* (species; e.g., gut site), *Dielma fastidiosa* (species; e.g., gut site), *Dielma fastidiosa* (species; e.g., gut site), *Dorea formicigenerans* (species; e.g., gut site), *Dorea formicigenerans* (species; e.g., gut site), *Dorea longicatena* (species; e.g., gut site), *Dorea longicatena* (species; e.g., gut site), *Eggerthella lenta* (species; e.g., gut site), *Eggerthella sinensis* (species; e.g., gut site), *Eggerthella* sp. HGA1 (species; e.g., gut site), *Eggerthella* sp. HGA1 (species; e.g., gut site), *Eisenbergiella tayi* (species; e.g., gut site), *Eisenbergiella tayi* (species; e.g., gut site), *Enterococcus* sp. C6I11 (species; e.g., gut site), *Enterococcus* sp. SI-4 (species; e.g., gut site), *Enterococcus* sp. SI-4 (species; e.g., gut site), *Erysipelatoclostridium ramosum* (species; e.g., gut site), *Erysipelatoclostridium ramosum* (species; e.g., gut site), *Eubacterium callanderi* (species; e.g., gut site), *Eubacterium callanderi* (species; e.g., gut site), *Faecalibacterium prausnitzii* (species; e.g., gut site), *Faecalibacterium prausnitzii* (species; e.g., mouth site), *Faecalibacterium prausnitzii* (species; e.g., gut site), *Faecalibacterium* sp. canine oral taxon 147 (species; e.g., gut site), *Fastidiosipila sanguinis* (species; e.g., gut site), *Flavonifractor plautii* (species; e.g., gut site), *Flavonifractor plautii* (species; e.g., gut site), *Fusicatenibacter saccharivorans* (species; e.g., gut site), *Fusicatenibacter saccharivorans* (species; e.g., gut site), *Fusobacterium periodonticum* (species; e.g., gut site), *Fusobacterium* sp. CM21 (species; e.g., gut site), *Fusobacterium* sp. CM22 (species; e.g., gut site), *Gordonibacter pamelaeae* (species; e.g., gut site), *Gordonibacter pamelaeae* (species; e.g., gut site), *Granulicatella adiacens* (species; e.g., gut site), *Holdemania filiformis* (species; e.g., gut site), *Holdemania filiformis* (species; e.g., gut site), *Howardella ureilytica* (species; e.g., gut site), *Klebsiella* sp. SOR89 (species; e.g., gut site), *Kluyvera georgiana* (species; e.g., genital site), *Lachnospira pectinoschiza* (species; e.g., gut site), *Lachnospira pectinoschiza* (species; e.g., gut site), *Lactobacillus fornicalis* (species; e.g., genital site), *Lactobacillus salivarius* (species; e.g., gut site), *Lactobacillus* sp. BL302 (species; e.g., genital site), *Lactobacillus* sp. TAB-30 (species; e.g., gut site), *Lactobacillus* sp. TAB-30 (species; e.g., gut site), *Lactonifactor longoviformis* (species; e.g., gut site), *Lactonifactor longoviformis* (species; e.g., gut site), *Megasphaera genomosp.* C1 (species; e.g., gut site), *Methanobrevibacter smithii* (species; e.g., gut site), *Odoribacter splanchnicus* (species; e.g., gut site), *Parabacteroides distasonis* (species; e.g., gut site), *Parabacteroides distasonis* (species; e.g., gut site), *Parabacteroides merdae* (species; e.g., gut site), *Parasutterella excrementihominis* (species; e.g., gut site), *Parvimonas micra* (species; e.g., gut site), *Peptostreptococcus stomatis* (species; e.g., gut site), *Phascolarctobacterium faecium* (species; e.g., gut site), *Phascolarctobacterium succinatutens* (species; e.g., gut site), *Porphyromonas sp.* 2026 (species; e.g., gut site), *Prevotella timonensis* (species; e.g., gut site), *Propionibacterium propionicum* (species; e.g., mouth site), *Pseudoflavonifractor capillosus* (species; e.g., gut site), *Pseudoflavonifractor capillosus* (species; e.g., gut site), *Robinsoniella peoriensis* (species; e.g., gut site), *Roseburia faecis* (species; e.g., gut site), *Roseburia hominis* (species; e.g., gut site), *Roseburia inulinivorans* (species; e.g., gut site), *Roseburia inulinivorans* (species; e.g., gut site), *Roseburia sp.* 11SE39 (species; e.g., gut site), *Roseburia sp.* 11SE39 (species; e.g., gut site), *Roseburia sp.* 499 (species; e.g., gut site), *Streptococcus sp.* 11aTha1 (species; e.g., mouth site), *Streptococcus sp.* 2011_Oral_MS_A3 (species; e.g., gut site), *Subdoligranulum variabile* (species; e.g., gut site), *Subdoligranulum variabile* (species; e.g., gut site), *Sutterella wadsworthensis* (species; e.g., gut site), *Sutterella wadsworthensis* (species; e.g., gut site).

Thus, characterization of the subject can include characterization of the subject as someone with one or more microorganism-related conditions, such as based upon detection of one or more of a combination of any of the above features, and such as in a manner that is an alternative or supplemental to typical methods of diagnosis and/or other suitable purposes. In variations of the specific example, the set of features can, however, include any other suitable features useful for diagnostics and/or other suitable purposes. However, any suitable taxons, functions, and/or other suitable aspects associated with microbiome features can be associated with any suitable sample sites.

3.4 Determining a Therapy Model.

Block S140 recites: generating a therapy model configured to modulate microorganism distributions in subjects characterized according to the characterization process. Block S140 can function to identify or predict therapies (e.g., probiotic-based therapies, phage-based therapies, small molecule-based therapies, etc.) that can shift a subject's microbiome composition and/or functional features toward a desired equilibrium state in promotion of the subject's health, and/or determine therapies for otherwise modifying a state of a microorganism-related condition (e.g., modifying a user behavior associated with a human behavior condition, etc.). In Block S140, the therapies can be selected from therapies including one or more of: probiotic therapies, phage-based therapies, small molecule-based therapies, cognitive/behavioral therapies, physical rehabilitation therapies, clinical therapies, medication-based therapies, diet-related therapies, and/or any other suitable therapy designed to operate in any other suitable manner in promoting a user's health. In a specific example of a bacteriophage-based therapy, one or more populations (e.g., in terms of colony forming units) of bacteriophages specific to a certain bacteria (or other microorganism) represented in the subject can be used to down-regulate or otherwise eliminate populations of the certain bacteria. As such, bacteriophage-based therapies can be used to reduce the size(s) of the undesired population(s) of bacteria represented in the subject. Complementarily, bacteriophage-based therapies can be used to increase the relative abundances of bacterial populations not targeted by the bacteriophage(s) used.

Figure 4:
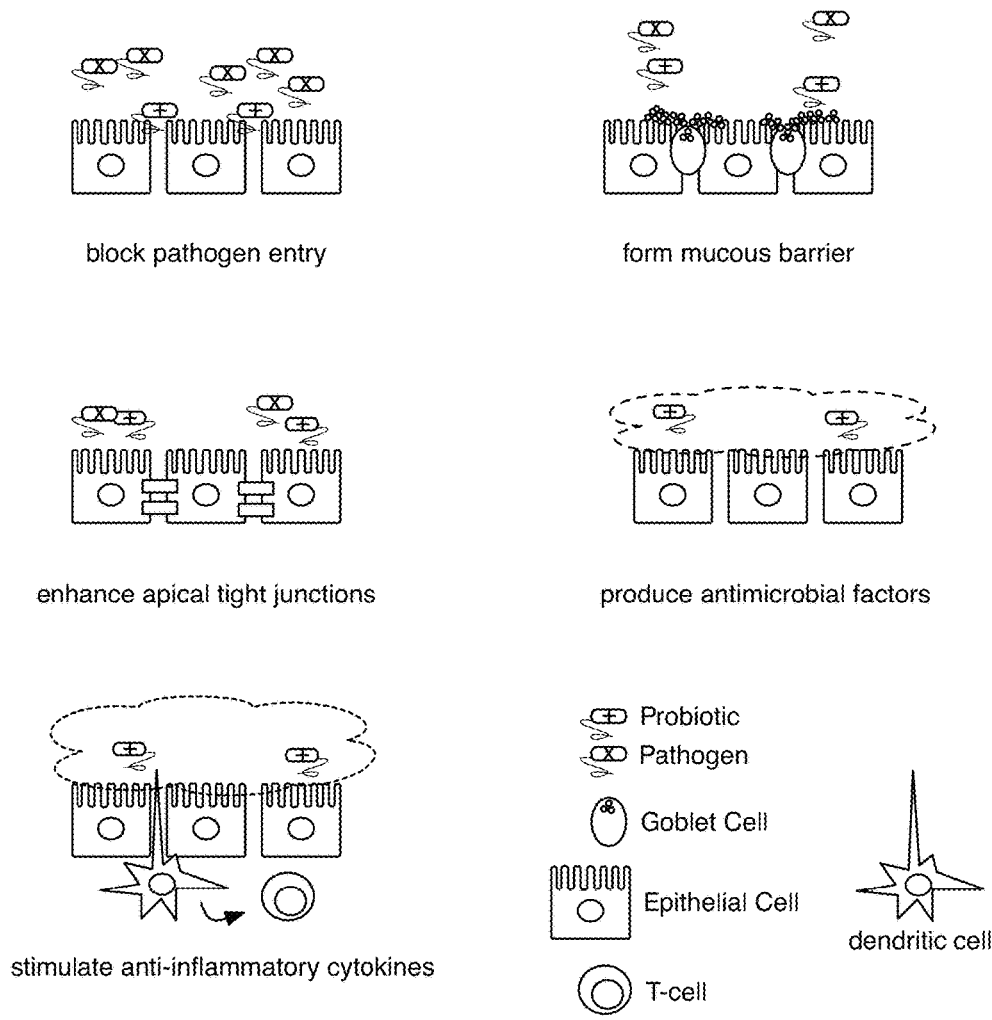
FIG. 4 depicts variations of mechanisms by which probiotic-based therapies operate in an embodiment of a method.

In another specific example of probiotic therapies, as shown in FIG. 4, candidate therapies of the therapy model can perform one or more of: blocking pathogen entry into an epithelial cell by providing a physical barrier (e.g., by way of colonization resistance), inducing formation of a mucous barrier by stimulation of goblet cells, enhance integrity of apical tight junctions between epithelial cells of a subject (e.g., by stimulating up regulation of zona-occludens 1, by preventing tight junction protein redistribution), producing antimicrobial factors, stimulating production of anti-inflammatory cytokines (e.g., by signaling of dendritic cells and induction of regulatory T-cells), triggering an immune response, and performing any other suitable function that adjusts a subject's microbiome away from a state of dysbiosis. In another specific example, therapies can include medical-device based therapies (e.g., associated with human behavior modification, associated with treatment of disease-related conditions, etc.).

In variations, the therapy model is preferably based upon data from a large population of subjects, which can include the population of subjects from which the microbiome diversity datasets are derived in Block S110, where microbiome composition and/or functional features or states of health, prior exposure to and post exposure to a variety of therapeutic measures, are well characterized. Such data can be used to train and validate the therapy provision model, in identifying therapeutic measures that provide desired outcomes for subjects based upon different microbiome characterizations. In variations, support vector machines, as a supervised machine learning algorithm, can be used to generate the therapy provision model. However, any other suitable machine learning algorithm described above can facilitate generation of the therapy provision model.

While some methods of statistical analyses and machine learning are described in relation to performance of the Blocks above, variations of the method 100 can additionally or alternatively utilize any other suitable algorithms in performing the characterization process. In variations, the algorithm(s) can be characterized by a learning style including any one or more of: supervised learning (e.g., using logistic regression, using back propagation neural networks), unsupervised learning (e.g., using an Apriori algorithm, using K-means clustering), semi-supervised learning, reinforcement learning (e.g., using a Q-learning algorithm, using temporal difference learning), and any other suitable learning style. Furthermore, the algorithm(s) can implement any one or more of: a regression algorithm (e.g., ordinary least squares, logistic regression, stepwise regression, multivariate adaptive regression splines, locally estimated scatterplot smoothing, etc.), an instance-based method (e.g., k-nearest neighbor, learning vector quantization, self-organizing map, etc.), a regularization method (e.g., ridge regression, least absolute shrinkage and selection operator, elastic net, etc.), a decision tree learning method (e.g., classification and regression tree, iterative dichotomiser 3, C4.5, chi-squared automatic interaction detection, decision stump, random forest, multivariate adaptive regression splines, gradient boosting machines, etc.), a Bayesian method (e.g., naïve Bayes, averaged one-dependence estimators, Bayesian belief network, etc.), a kernel method (e.g., a support vector machine, a radial basis function, a linear discriminate analysis, etc.), a clustering method (e.g., k-means clustering, expectation maximization, etc.), an associated rule learning algorithm (e.g., an Apriori algorithm, an Eclat algorithm, etc.), an artificial neural network model (e.g., a Perceptron method, a back-propagation method, a Hopfield network method, a self-organizing map method, a learning vector quantization method, etc.), a deep learning algorithm (e.g., a restricted Boltzmann machine, a deep belief network method, a convolution network method, a stacked auto-encoder method, etc.), a dimensionality reduction method (e.g., principal component analysis, partial lest squares regression, Sammon mapping, multidimensional scaling, projection pursuit, etc.), an ensemble method (e.g., boosting, boostrapped aggregation, AdaBoost, stacked generalization, gradient boosting machine method, random forest method, etc.), and any suitable form of algorithm.

Additionally or alternatively, the therapy model can be derived in relation to identification of a "normal" or baseline microbiome composition and/or functional features, as assessed from subjects of a population of subjects who are identified to be in good health. Upon identification of a subset of subjects of the population of subjects who are characterized to be in good health (e.g., using features of the characterization process), therapies that modulate microbiome compositions and/or functional features toward those of subjects in good health can be generated in Block S140. Block S140 can thus include identification of one or more baseline microbiome compositions and/or functional features (e.g., one baseline microbiome for each of a set of demographics), and potential therapy formulations and therapy regimens that can shift microbiomes of subjects who are in a state of dysbiosis toward one of the identified baseline microbiome compositions and/or functional features. The therapy model can, however, be generated and/or refined in any other suitable manner.

Microorganism compositions associated with probiotic therapies associated with the therapy model preferably include microorganisms that are culturable (e.g., able to be expanded to provide a scalable therapy) and non-lethal (e.g., non-lethal in their desired therapeutic dosages). Furthermore, microorganism compositions can include a single type of microorganism that has an acute or moderated effect upon a subject's microbiome. Additionally or alternatively, microorganism compositions can include balanced combinations of multiple types of microorganisms that are configured to cooperate with each other in driving a subject's microbiome toward a desired state. For instance, a combination of multiple types of bacteria in a probiotic therapy can include a first bacteria type that generates products that are used by a second bacteria type that has a strong effect in positively affecting a subject's microbiome. Additionally or alternatively, a combination of multiple types of bacteria in a probiotic therapy can include several bacteria types that produce proteins with the same functions that positively affect a subject's microbiome.

Probiotic compositions can be naturally or synthetically derived. For instance, in one application, a probiotic composition can be naturally derived from fecal matter or other biological matter (e.g., of one or more subjects having a baseline microbiome composition and/or functional features, as identified using the characterization process and the therapy model). Additionally or alternatively, probiotic compositions can be synthetically derived (e.g., derived using a benchtop method) based upon a baseline microbiome composition and/or functional features, as identified using the characterization process and the therapy model. In variations, microorganism agents that can be used in probiotic therapies can include one or more of: yeast (e.g., *Saccharomyces boulardii*), gram-negative bacteria (e.g., *E. coli* Nissle), gram-positive bacteria (e.g., *Bifidobacteria bifidum, Bifidobacteria infantis, Lactobacillus rhamnosus, Lactococcus lactis, Lactobacillus plantarum, Lactobacillus acidophilus, Lactobacillus casei, Bacillus polyfermenticus*, etc.), and any other suitable type of microorganism agent.

In a variation, for subjects who exhibit a caffeine consumption lifestyle behavior (and/or other suitable microorganism-related conditions), a probiotic therapy, prebiotic therapy, and/or other suitable consumable can be associated with (e.g., include) a combination of any one or more of: *Collinsella aerofaciens, Blautia luti, Erysipelatoclostridium ramosum, Haemophilus parainfluenzae, Subdoligranulum variabile, Parabacteroides merdae, Alistipes putredinis, Bacteroides vulgatus, Bacteroides fragilis, Faecalibacterium prausnitzii, Bacteroides thetaiotaomicron, Dorea formicigenerans, Blautia faecis, Bacteroides acidifaciens, Flavonifractor plautii, Methanobrevibacter smithii*, and any other suitable microorganisms or phage vector (e.g., bacteriophage, virus, etc.).

In another variation, for subjects who exhibit a cancer condition (e.g., exhibiting cancer-associated-microorganisms, etc.) (and/or other suitable microorganism-related conditions), a probiotic therapy, prebiotic therapy, and/or other suitable consumable can be associated with (e.g., include) a combination of any one or more of: *Blautia luti, Collinsella aerofaciens, Flavonifractor plautii, Subdoligranulum variabile, Faecalibacterium prausnitzii, Dorea formicigenerans, Roseburia inulinivorans, Blautia* sp. YHC-4, *Parasutterella excrementihominis, Sutterella wadsworthensis, Bacteroides caccae*, and any other suitable microorganisms or phage vector (e.g., bacteriophage, virus, etc.).

In another variation, for subjects who exhibit an anemia condition (and/or other suitable microorganism-related conditions), a probiotic therapy, prebiotic therapy, and/or other suitable consumable can be associated with (e.g., include) a combination of any one or more of: *Flavonifractor plautii, Blautia luti, Collinsella aerofaciens, Subdoligranulum variabile, Dorea formicigenerans, Blautia* sp. YHC-4, *Faecalibacterium prausnitzii, Roseburia inulinivorans* and any other suitable microorganisms or phage vector (e.g., bacteriophage, virus, etc.).

In another variation, for subjects who exhibit an alcohol consumption condition (and/or other suitable microorganism-related conditions), a probiotic therapy, prebiotic therapy, and/or other suitable consumable can be associated with (e.g., include) a combination of any one or more of: *Collinsella aerofaciens, Parabacteroides distasonis, Odoribacter splanchnicus, Faecalibacterium prausnitzii, Blautia luti, Subdoligranulum variabile, Bacteroides thetaiotaomicron, Parabacteroides merdae, Roseburia inulinivorans, Flavonifractor plautii, Streptococcus thermophilus, Sutterella wadsworthensis, Roseburia hominis*, and any other suitable microorganisms or phage vector (e.g., bacteriophage, virus, etc.).

In another variation, for subjects who exhibit an extreme physical exercise condition (e.g., habit) (and/or other suitable microorganism-related conditions), a probiotic therapy, prebiotic therapy, and/or other suitable consumable can be associated with (e.g., include) a combination of any one or more of: *Bacteroides vulgatus, Parabacteroides merdae, Bacteroides caccae, Collinsella aerofaciens, Phascolarctobacterium faecium, Bacteroides fragilis, Parabacteroides distasonis, Flavonifractor plautii, Megamonas funiformis, Roseburia inulinivorans* and any other suitable microorganisms or phage vector (e.g., bacteriophage, virus, etc.).

In another variation, for subjects who exhibit a moderate physical exercise condition (and/or other suitable microorganism-related conditions), a probiotic therapy, prebiotic therapy, and/or other suitable consumable can be associated with (e.g., include) a combination of any one or more of: *Bacteroides vulgatus, Bacteroides caccae, Parabacteroides merdae, Phascolarctobacterium faecium, Parabacteroides distasonis, Flavonifractor plautii, Bacteroides fragilis, Parasutterella excrementihominis, Blautia* sp. YHC-4, *Collinsella aerofaciens, Faecalibacterium prausnitzii* and any other suitable microorganisms or phage vector (e.g., bacteriophage, virus, etc.).

In another variation, for subjects who exhibit a menopause condition (and/or other suitable microorganism-related conditions), a probiotic therapy, prebiotic therapy, and/or other suitable consumable can be associated with (e.g., include) a combination of any one or more of: *Bifidobacteria bifidum, Bifidobacteria infantis, Lactobacillus rhamnosus, Lactococcus lactis, Lactobacillus plantarum, Lactobacillus acidophilus, Lactobacillus casei, Bacillus polyfermenticus*, Lactobacillaceae (Family), Clostridia (Class) Clostridiales (Order) and any other suitable microorganisms or phage vector (e.g., bacteriophage, virus, etc.).

In another variation, for subjects who exhibit a probiotics-related condition (e.g., associated with food habits and/or diet, etc.) (and/or other suitable microorganism-related conditions), a probiotic therapy, prebiotic therapy, and/or other suitable consumable can be associated with (e.g., include) a combination of any one or more of: *Blautia luti, Flavonifractor plautii, Collinsella aerofaciens, Blautia glucerasea, Erysipelatoclostridium ramosum, Dialister propionicifaciens, Blautia* sp. YHC-4 and any other suitable microorganisms or phage vector (e.g., bacteriophage, virus, etc.).

In another variation, for subjects who exhibit a Lyme disease condition, a probiotic therapy, prebiotic therapy, and/or other suitable consumable can be associated with (e.g., include) a combination of any one or more of: *Blautia luti, Parabacteroides merdae* and any other suitable microorganisms or phage vector (e.g., bacteriophage, virus, etc.).

In another variation, microbiome datasets (e.g., based on composition or diversity of recognizable patterns of relative abundance in microorganisms that are present in subject microbiome) can be used as a diagnostic tool using bioinformatics pipelines and characterization describe above. However, probiotic therapies and/or other suitable therapies can include any suitable combination of microorganisms associated with any suitable taxa described herein.

Probiotics and/or other suitable consumables can be provided at dosages of 0.1 million to 10 billion CFUs (and/or other suitable dosages), such as determined from a therapy model that predicts positive adjustment of a patient's microbiome in response to the therapy. In a specific example, a subject can be instructed to ingest capsules including the probiotic formulation according to a regimen tailored to one or more of his/her: physiology (e.g., body mass index, weight, height), demographics (e.g., gender, age), severity of dysbiosis, sensitivity to medications, and any other suitable factor. For subjects who exhibit a microorganism-related condition, associated-microorganisms (e.g., corresponding to correlated microbiome composition features) can provide a dataset based on composition and/or diversity of recognizable patterns of relative abundance in microorganisms that are present in subject microbiome, and can be used as a diagnostic tool using bioinformatics pipelines and characterization describe above.

3.5 Processing a User Biological Sample.

The method 100 can additionally or alternatively include Block S150, which recites: processing one or more biological samples from a user (e.g., subject). Block S150 can function to facilitate generation of a microbiome dataset for the subject, such as for use in deriving inputs for the characterization process (e.g., for generating a microorganism-related characterization for the user, etc.). As such, Block S150 can include receiving, processing, and/or analyzing one or more biological samples from one or more users (e.g., multiple biological samples for the same user over time, different biological samples for different users, etc.). In Block S150, the biological sample is preferably generated from the subject and/or an environment of the subject in a non-invasive manner. In variations, non-invasive manners of sample reception can use any one or more of: a permeable substrate (e.g., a swab configured to wipe a region of a subject's body, toilet paper, a sponge, etc.), a non-permeable substrate (e.g., a slide, tape, etc.) a container (e.g., vial, tube, bag, etc.) configured to receive a sample from a region of a subject's body, and any other suitable sample-reception element. In a specific example, the biological sample can be collected from one or more of the subject's nose, skin, genitals, mouth, and gut in a non-invasive manner (e.g., using a swab and a vial). However, the biological sample can additionally or alternatively be received in a semi-invasive manner or an invasive manner. In variations, invasive manners of sample reception can use any one or more of: a needle, a syringe, a biopsy element, a lance, and any other suitable instrument for collection of a sample in a semi-invasive or invasive manner. In specific examples, samples can include blood samples, plasma/serum samples (e.g., to enable extraction of cell-free DNA), and tissue samples.

In the above variations and examples, the biological sample can be taken from the body of the subject without facilitation by another entity (e.g., a caretaker associated with a subject, a health care professional, an automated or semi-automated sample collection apparatus, etc.), or can alternatively be taken from the body of the subject with the assistance of another entity. In one example, where the biological sample is taken from the subject without facilitation by another entity in the sample extraction process, a sample-provision kit can be provided to the subject. In the example, the kit can include one or more swabs for sample acquisition, one or more containers configured to receive the swab(s) for storage, instructions for sample provision and setup of a user account, elements configured to associate the sample(s) with the subject (e.g., barcode identifiers, tags, etc.), and a receptacle that allows the sample(s) from the subject to be delivered to a sample processing operation (e.g., by a mail delivery system). In another example, where the biological sample is extracted from the subject with the help of another entity, one or more samples can be collected in a clinical or research setting from the subject (e.g., during a clinical appointment). The biological sample can, however, be received from the subject in any other suitable manner.

Furthermore, processing and analyzing the biological sample (e.g., to generate a user microbiome dataset; etc.) from the subject is preferably performed in a manner similar to that of one of the embodiments, variations, and/or examples of sample reception described in relation to Block S110 above, and/or any other suitable portions of the method 100. As such, reception and processing of the biological sample in Block S150 can be performed for the subject using similar processes as those for receiving and processing biological samples used to generate the characterization process and/or the therapy model of the method 100, in order to provide consistency of process. However, biological sample reception and processing in Block S150 can alternatively be performed in any other suitable manner.

3.6 Determining a Microorganism-Related Characterization.

The method 100 can additionally or alternatively include Block S160, which recites: determining, with the characterization process, a microorganism-related characterization (e.g., human behavior characterization, disease-related characterization, etc.) for the user based upon processing one or more microbiome dataset (e.g., user microorganism sequence dataset, microbiome composition dataset, microbiome functional diversity dataset; processing of the microbiome dataset to extract microbiome features; etc.) derived from the biological sample of the user. Block S160 can function to characterize one or more microorganism-related conditions for a user, such as through extracting features from microbiome-derived data of the subject, and using the features as inputs into an embodiment, variation, or example of the characterization process described in Block S130 above. In an example, Block S160 can include generating a microorganism-related characterization (e.g., human behavior characterization, disease-related characterization, etc.) for the user based on user microbiome features and a microorganism-related condition characterization model (e.g., generated in Block S130). Microorganism-related characterizations can be for any number and/or combination of microorganism-related conditions (e.g., a combination of microorganism-related conditions, a single microorganism-related condition, and/or other suitable microorganism-related conditions; etc.). Microorganism-related characterizations can include one or more of: diagnoses (e.g., presence or absence of a microorganism-related condition; etc.); risk (e.g., risk scores for developing and/or the presence of a microorganism-related condition; information regarding microorganism-related characterizations (e.g., symptoms, signs, triggers, associated conditions, etc.); comparisons (e.g., comparisons with other subgroups, populations, users, historic health statuses of the user such as historic microbiome compositions and/or functional diversities; comparisons associated with microorganism-related conditions; etc.), and/or any other suitable data.

In a variation, microorganism-related characterization (e.g., human behavior characterization, disease-related characterization, etc.) can include determining one or more microorganism-related profiles (e.g., human behavior profiles, disease-related profiles, etc.) describing human behaviors and/or disease-related conditions for the user (e.g., known to affect the user; predicted to affect the user, such as based on microbiome features, supplementary data, etc.). Microorganism-related profiles and/or other characterizations can be associated with (e.g., correlated with, etc.) one or more of: family history, age, gender, weight, height, other demographic characteristics, and/or any other suitable supplementary data.

In another variation, a microorganism-related characterization (e.g., human behavior characterization, disease-related characterization, etc.) can include a microbiome diversity score (e.g., in relation to microbiome composition, function, etc.) associated with (e.g., correlated with; negatively correlated with; positively correlated with; etc.) a microbiome diversity score correlated with the microorganism-related condition. In an example, the method 100 can include promoting a diet-related therapy (e.g., probiotics; dietary regimen modifications such as alcohol consumption reduction and/or caffeine consumption reduction; etc.) operable to improve the microbiome diversity score for improving a state of the microorganism-related condition, such as based on a microorganism-related characterization (e.g., including the microbiome diversity score for the user) and/or diet-related supplementary data collected from the user. In examples, the microorganism-related characterization (e.g., human behavior characterization, disease-related characterization, etc.) can include microbiome diversity scores over time (e.g., calculated for a plurality of biological samples of the user collected over time), comparisons to microbiome diversity scores for other users, and/or any other suitable type of microbiome diversity score. However, processing microbiome diversity scores (e.g., determining microbiome diversity scores; using microbiome diversity scores to determine and/or provide therapies; etc.) can be performed in any suitable manner.

Determining a microorganism-related characterization (e.g., human behavior characterization, disease-related characterization, etc.) in Block S160 preferably includes identifying features and/or combinations of features associated with the microbiome composition and/or functional features of the subject, inputting the features into the characterization process, and receiving an output that characterizes the subject as belonging to one or more of: a behavioral group, a gender group, a dietary group, a disease-state group, and any other suitable group capable of being identified by the characterization process. Block S160 can additionally or alternatively include generation of and/or output of a confidence metric associated with the characterization of the subject. For instance, a confidence metric can be derived from the number of features used to generate the characterization, relative weights or rankings of features used to generate the characterization, measures of bias in the characterization process, and/or any other suitable parameter associated with aspects of the characterization process. However, leveraging user microbiome features can be performed in any suitable manner to generate any suitable microorganism-related characterizations.

In some variations, features extracted from the microbiome dataset of the subject can be supplemented with supplementary features (e.g., extracted from supplementary data collected for the user; such as survey-derived features, medical history-derived features, sensor data, etc.), where such data, the user microbiome data, and/or other suitable data can be used to further refine the characterization process of Block S130, Block S160, and/or other suitable portions of the method 100.

Determining a microorganism-related characterization (e.g., human behavior characterization, disease-related characterization, etc.) preferably includes extracting and applying user microbiome features (e.g., user microbiome composition diversity features; user microbiome functional diversity features; etc.) for the user (e.g., based on a user microbiome dataset), characterization models, and/or other suitable components, such as by employing approaches described in Block S130, and/or by employing any suitable approaches described herein.

Figure 6:
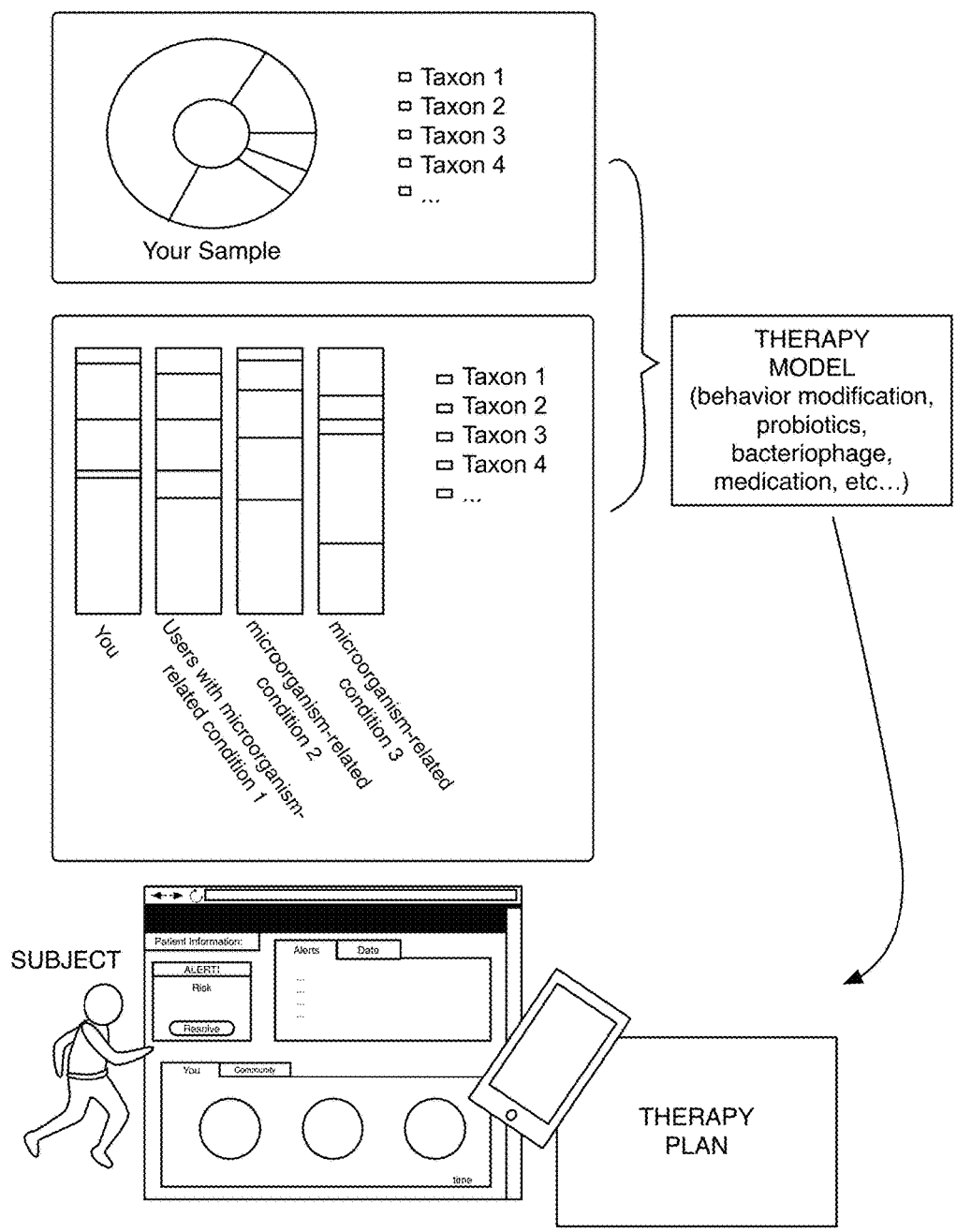
FIG. 6 depicts examples of notification provision.

In variations, as shown in FIG. 6, Block S160 can include presenting microorganism-related characterizations (e.g., information extracted from the characterizations, etc.), such as at a web interface, a mobile application, and/or any other suitable interface, but presentation of information can be performed in any suitable manner. However, the microbiome dataset of the subject can additionally or alternatively be used in any other suitable manner to enhance the models of the method 100, and Block S160 can be performed in any suitable manner.

3.7 Promoting a Therapy.

Figure 5:
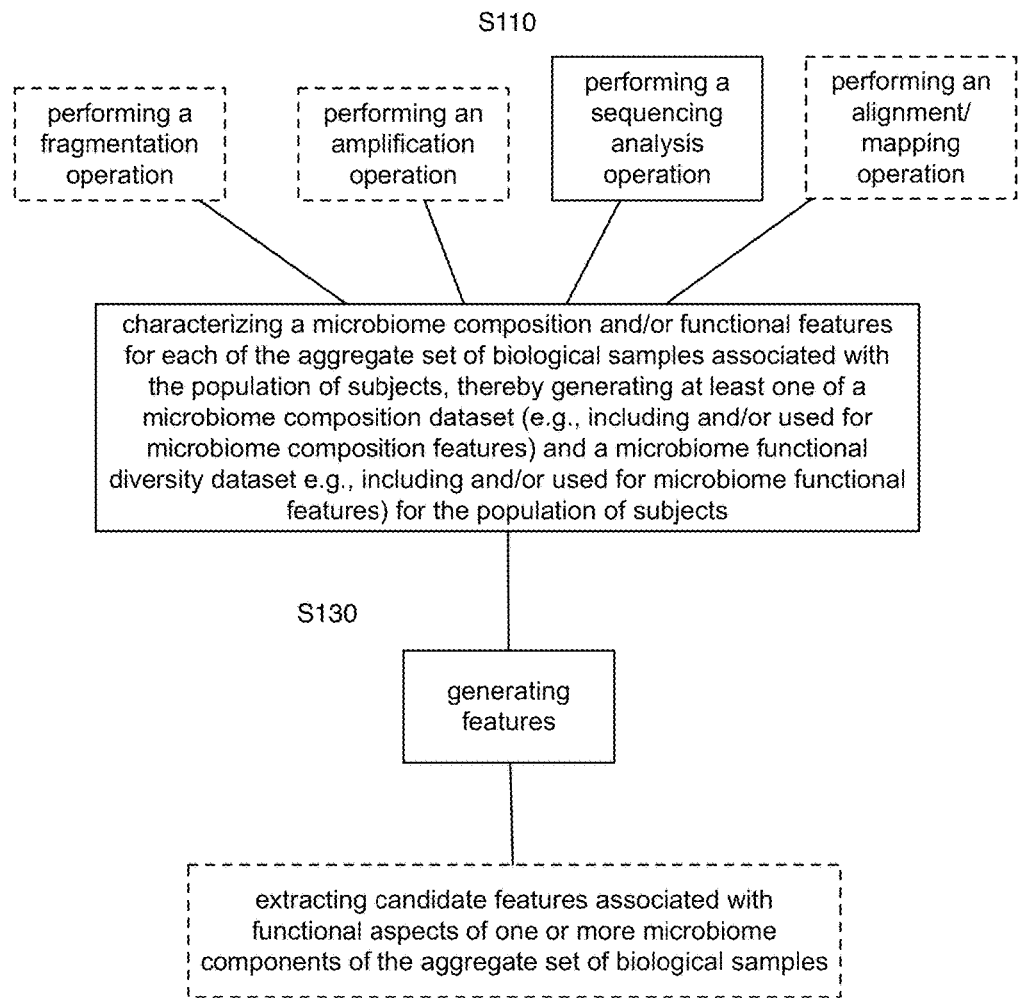
FIG. 5 depicts variations of sample processing in an embodiment of a method.
Figure 9:
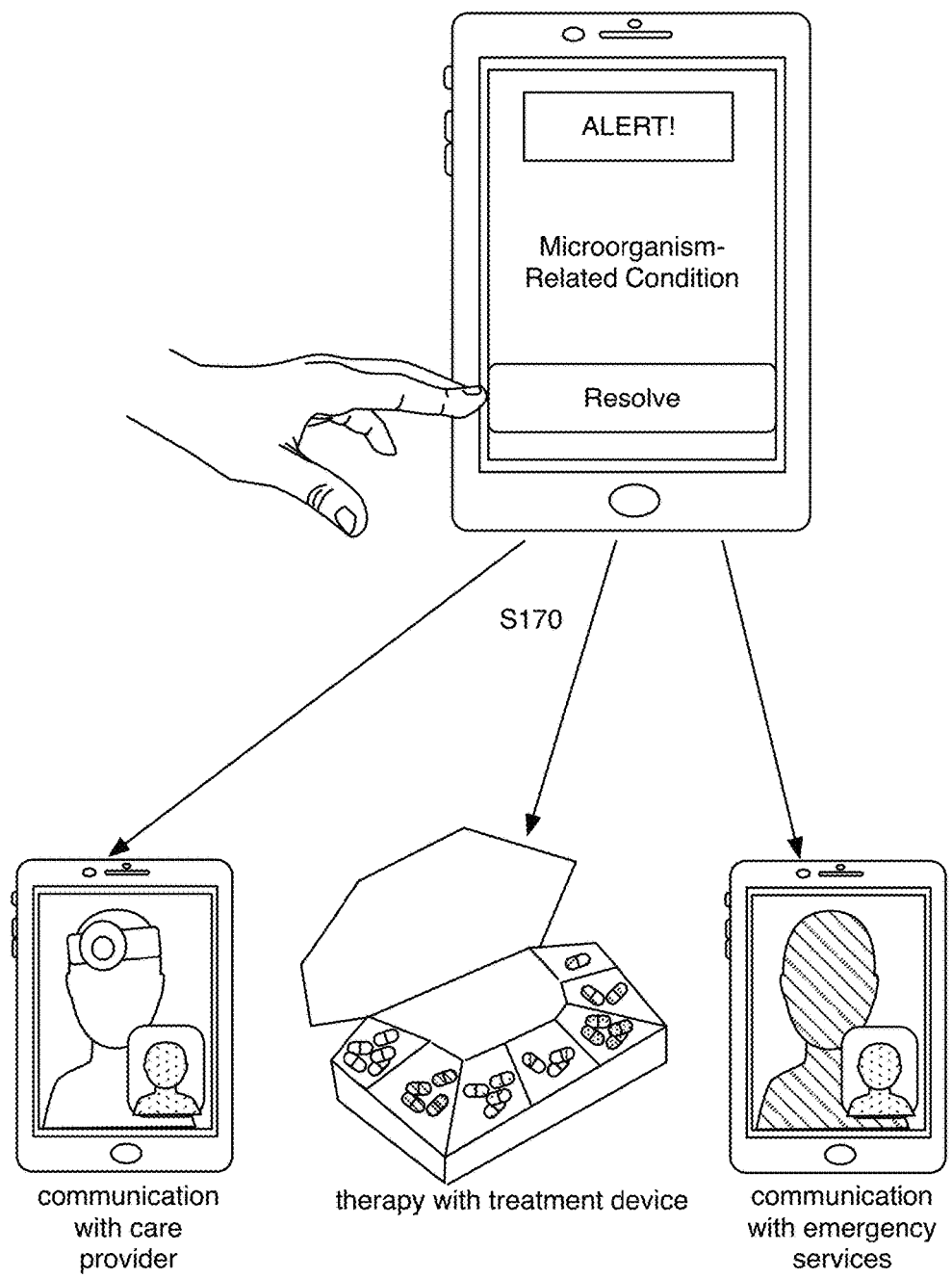
FIG. 9 depicts promoting a therapy in an embodiment of a method.

As shown in FIG. 9, the method 100 can additionally or alternatively include Block S170, which recites: promoting (e.g., providing, facilitating provision of, etc.) a therapy for the microorganism-related condition to the user (e.g., based upon the microorganism-related characterization and/or a therapy model). Block S170 can function to recommend or provide a personalized therapy to the subject, in order to shift the microbiome composition and/or functional diversity of a user toward a desired equilibrium state (and/or otherwise improving a state of the microorganism-related condition, etc.). Block S170 can include provision of a customized therapy to the subject according to their microbiome composition and functional features, as shown in FIG. 5, where the customized therapy can include a formulation of microorganisms configured to correct dysbiosis characteristic of subjects having the identified characterization. As such, outputs of Block S140 can be used to directly promote a customized therapy formulation and regimen (e.g., dosage, usage instructions) to the subject based upon a trained therapy model. Additionally or alternatively, therapy provision can include recommendation of available therapeutic measures configured to shift microbiome composition and/or functional features toward a desired state. In variations, therapies can include any one or more of: consumables, topical therapies (e.g., lotions, ointments, antiseptics, etc.), medication (e.g., cancer-related medication, anemia-related medication, Lyme disease-related medication, medications associated with any suitable medication type and/or dosage, etc.), bacteriophages, environmental treatments, behavioral modification (e.g., diet modification therapies, stress-reduction therapies, physical activity-related therapies, etc.), diagnostic procedures, other medical-related procedures, and/or any other suitable therapies associated with microorganism-related conditions. Consumables can include any one or more of: food and/or beverage items (e.g., probiotic and/or prebiotic food and/or beverage items, etc.), nutritional supplements (e.g., vitamins, minerals, fiber, fatty acids, amino acids, prebiotics, probiotics, etc.), consumable medications, and/or any other suitable therapeutic measure.

For example, a combination of commercially available probiotic supplements can include a suitable probiotic therapy for the subject according to an output of the therapy model. In another example, the method 100 can include determining a microorganism-related condition risk for the user for the microorganism-related condition based on a microorganism-related characterization (e.g., human behavior characterization, disease-related characterization, etc.) model (e.g., and/or user microbiome features); and promoting a therapy to the user based on the microorganism-related condition risk.

In a variation, promoting a therapy can include promoting a diagnostic procedure (e.g., for facilitating detection of microorganism-related conditions such as human behavior conditions and/or disease-related conditions, which can motivate subsequent promotion of other therapies, such as for modulation of a user microbiome for improving a user health state associated with one or more microorganism-related conditions; etc.). Diagnostic procedures can include any one or more of: medical history analyses, imaging examinations, cell culture tests, antibody tests, skin prick testing, patch testing, blood testing, challenge testing, performing portions of the method 100, and/or any other suitable procedures for facilitating the detecting (e.g., observing, predicting, etc.) of microorganism-related conditions. Additionally or alternatively, diagnostic device-related information and/or other suitable diagnostic information can be processed as part of a supplementary dataset (e.g., in relation to Block S120, where such data can be used in determining and/or applying characterization models, therapy models, and/or other suitable models; etc.), and/or collected, used, and/or otherwise processed in relation to any suitable portions of the method 100 (e.g., administering diagnostic procedures for users for monitoring therapy efficacy in relation to Block S180; etc.)

In another variation, Block S170 can include promoting a bacteriophage-based therapy. In more detail, one or more populations (e.g., in terms of colony forming units) of bacteriophages specific to a certain bacteria (or other microorganism) represented in the subject can be used to downregulate or otherwise eliminate populations of the certain bacteria. As such, bacteriophage-based therapies can be used to reduce the size(s) of the undesired population(s) of bacteria represented in the subject. Complementarily, bacteriophage-based therapies can be used to increase the relative abundances of bacterial populations not targeted by the bacteriophage(s) used.

In another variation, therapy provision in Block S170 can include provision of notifications to a subject regarding the recommended therapy, other forms of therapy, microorganism-related characterizations, and/or other suitable data. In a specific example, providing a therapy to a user can include providing therapy recommendations (e.g., substantially concurrently with providing information derived from a microorganism-related characterization for a user; etc.) and/or other suitable therapy-related information (e.g., therapy efficacy; comparisons to other individual users, subgroups of users, and/or populations of users; therapy comparisons; historic therapies and/or associated therapy-related information; psychological therapy guides such as for cognitive behavioral therapy; etc.), such as through presenting notifications at a web interface (e.g., through a user account associated with and identifying a user; etc.). Notifications can be provided to a subject by way of an electronic device (e.g., personal computer, mobile device, tablet, wearable, head-mounted wearable computing device, wrist-mounted wearable computing device, etc.) that executes an application, web interface, and/or messaging client configured for notification provision. In one example, a web interface of a personal computer or laptop associated with a subject can provide access, by the subject, to a user account of the subject, where the user account includes information regarding the user's microorganism-related characterization (e.g., human behavior characterization, disease-related characterization, etc.), detailed characterization of aspects of the user's microbiome (e.g., in relation to correlations with microorganism-related conditions; etc.), and/or notifications regarding suggested therapeutic measures (e.g., generated in Blocks S140 and/or S170, etc.). In another example, an application executing at a personal electronic device (e.g., smart phone, smart watch, head-mounted smart device) can be configured to provide notifications (e.g., at a display, haptically, in an auditory manner, etc.) regarding therapy suggestions generated by the therapy model of Block S170. Notifications and/or probiotic therapies can additionally or alternatively be provided directly through an entity associated with a subject (e.g., a caretaker, a spouse, a significant other, a healthcare professional, etc.). In some further variations, notifications can additionally or alternatively be provided to an entity (e.g., healthcare professional) associated with a subject, such as where the entity is able to facilitate provision of the therapy (e.g., by way of prescription, by way of conducting a therapeutic session, through a digital telemedicine session using optical and/or audio sensors of a computing device, etc.). Promoting notifications and/or other suitable therapies can, however, be performed in any suitable manner.

3.8 Monitoring Therapy Effectiveness.

Figure 7:
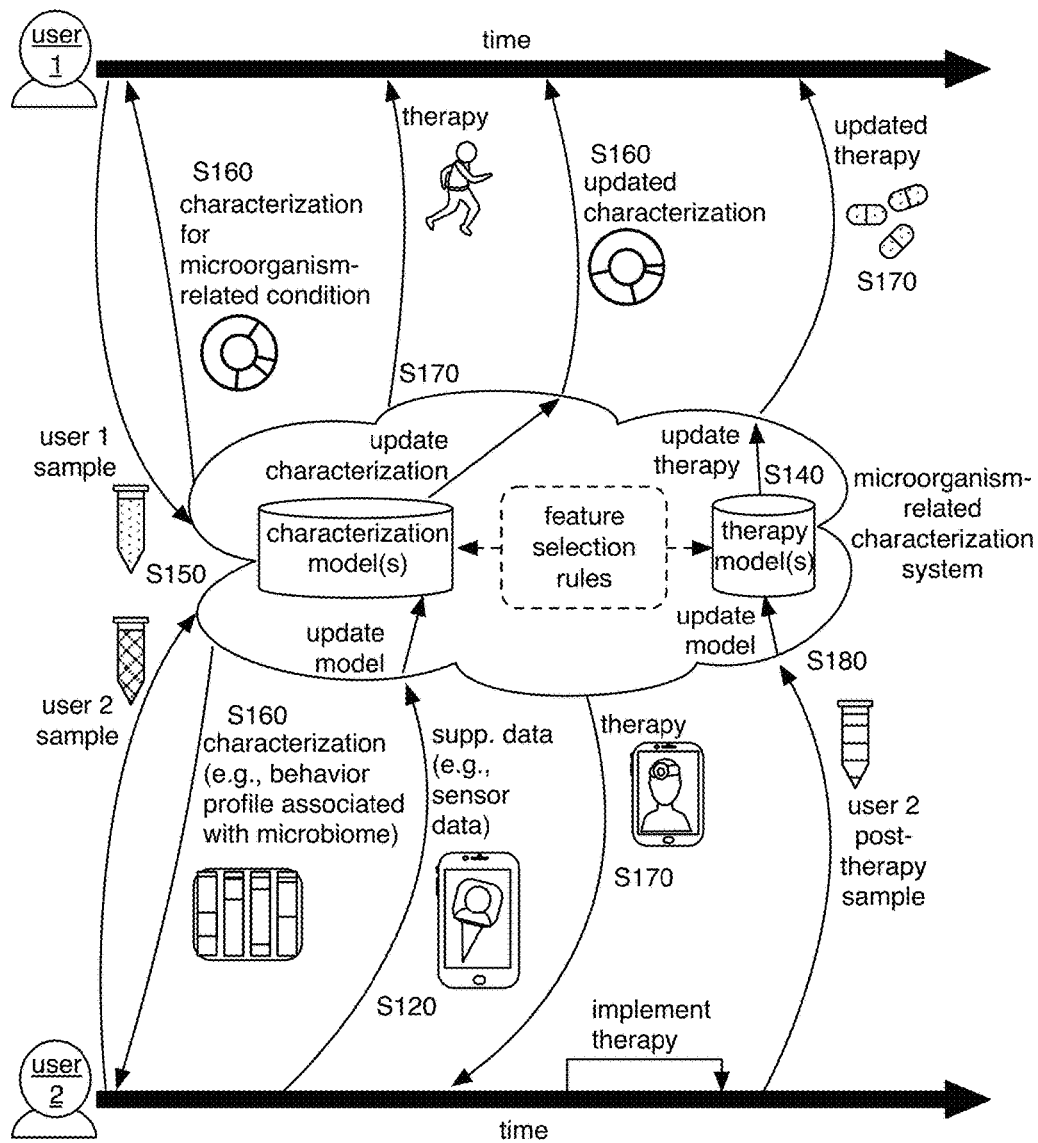
FIG. 7 depicts a schematic representation of variations of an embodiment of the method.

As shown in FIG. 7, the method can additionally or alternatively include Block S180, which recites: monitoring effectiveness of the therapy for the subject, based upon processing biological samples, to assess microbiome composition and/or functional features for the subject at a set of time points associated with the probiotic therapy. Block S180 can function to gather additional data regarding positive effects, negative effects, and/or lack of effectiveness of a probiotic therapy suggested by the therapy model for subjects of a given characterization. Monitoring of a subject during the course of a therapy promoted by the therapy model (e.g., by receiving and analyzing biological samples from the subject throughout therapy, by receiving survey-derived data from the subject throughout therapy) can thus be used to generate a therapy-effectiveness model for each characterization provided by the characterization process of Block S130, and each recommended therapy measure provided in Blocks S140 and S170.

In Block S180, the subject can be prompted to provide additional biological samples at one or more key time points of a therapy regimen that incorporates the therapy, and the additional biological sample(s) can be processed and analyzed (e.g., in a manner similar to that described in relation to Block S120) to generate metrics characterizing modulation of the subject's microbiome composition and/or functional features. For instance, metrics related to one or more of: a change in relative abundance of one or more taxonomic groups represented in the subject's microbiome at an earlier time point, a change in representation of a specific taxonomic group of the subject's microbiome, a ratio between abundance of a first taxonomic group of bacteria and abundance of a second taxonomic group of bacteria of the subject's microbiome, a change in relative abundance of one or more functional families in a subject's microbiome, and any other suitable metrics can be used to assess therapy effectiveness from changes in microbiome composition and/or functional features. Additionally or alternatively, survey-derived data from the subject, pertaining to experiences of the subject while on the therapy (e.g., experienced side effects, personal assessment of improvement, behavioral modifications, symptom improvement, etc.) can be used to determine effectiveness of the therapy in Block S180. For example, the method 100 can include receiving a post-therapy biological sample from the user; collecting a supplementary dataset from the user, where the supplementary dataset describes user adherence to a therapy (e.g., a determined and promoted therapy) and/or other suitable user characteristics (e.g., behaviors, conditions, etc.); generating a post-therapy microbiome characterization of the first user in relation to the microorganism-related condition based on the microorganism-related condition characterization model and the post-therapy biological sample; and promoting an updated therapy to the user for the microorganism-related condition based on the post-therapy microbiome characterization (e.g., based on a comparison between the post-therapy microbiome characterization and a pre-therapy microbiome characterization; etc.) and/or the user adherence to the therapy (e.g., modifying the therapy based on positive or negative results for the user microbiome in relation to the microorganism-related condition; etc.). Additionally or alternatively, other suitable data (e.g., supplementary data describing user behavior associated with the human behavior condition; supplementary data describing a disease-related condition such as observed symptoms; etc.) can be used in determining a post-therapy characterization (e.g., degree of change from pre- to post-therapy in relation to the microorganism-related condition; etc.), updated therapies (e.g., determining an updated therapy based on effectiveness and/or adherence to the promoted therapy, etc.). Therapy effectiveness, processing of additional biological samples (e.g., to determine additional microorganism-related characterizations, therapies, etc.), and/or other suitable aspects associated with continued biological sample collection, processing, and analysis in relation to microorganism-related conditions can be performed at any suitable time and frequency for generating, updating, and/or otherwise processing models (e.g., characterization models, therapy models, etc.), and/or for any other suitable purpose (e.g., as inputs associated with other portions of the method 100). However, Block S180 can be performed in any suitable manner.

The method 100 can, however, include any other suitable blocks or steps configured to facilitate reception of biological samples from subjects, processing of biological samples from subjects, analyzing data derived from biological samples, and generating models that can be used to provide customized diagnostics and/or probiotic-based therapeutics according to specific microbiome compositions and/or functional features of subjects.

The method 100 and/or system of the embodiments can be embodied and/or implemented at least in part as a machine configured to receive a computer-readable medium storing computer-readable instructions. The instructions can be executed by computer-executable components integrated with the application, applet, host, server, network, website, communication service, communication interface, hardware/firmware/software elements of a patient computer or mobile device, or any suitable combination thereof. Other systems and methods of the embodiments can be embodied and/or implemented at least in part as a machine configured to receive a computer-readable medium storing computer-readable instructions. The instructions can be executed by computer-executable components integrated by computer-executable components integrated with apparatuses and networks of the type described above. The computer-readable medium can be stored on any suitable computer readable media such as RAMs, ROMs, flash memory, EEPROMs, optical devices (CD or DVD), hard drives, floppy drives, or any suitable device. The computer-executable component can be a processor, though any suitable dedicated hardware device can (alternatively or additionally) execute the instructions.

The FIGURES illustrate the architecture, functionality and operation of possible implementations of systems, methods and computer program products according to preferred embodiments, example configurations, and variations thereof. In this regard, each block in the flowchart or block diagrams may represent a module, segment, step, or portion of code, which includes one or more executable instructions for implementing the specified logical function(s). It should also be noted that, in some alternative implementations, the functions noted in the block can occur out of the order noted in the FIGURES. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

As a person skilled in the art will recognize from the previous detailed description and from the figures and claims, modifications and changes can be made to the embodiments of the invention without departing from the scope of this invention as defined in the following claims.

We claim:

1. A method for characterizing a human behavior condition associated with microorganisms, the method comprising:
   collecting samples from a set of subjects, wherein the samples comprise microorganism nucleic acids associated with the human behavior condition;
   generating a microorganism sequence dataset for the set of subjects based on the microorganism nucleic acids;
   determining at least one of a set of microbiome composition diversity features and a set of microbiome functional diversity features associated with the set of subjects, based on the microorganism sequence dataset;
   collecting supplementary data associated with the human behavior condition for the set of subjects;
   generating a behavior characterization model based on the supplementary data and the at least one of the set of microbiome composition diversity features and the set of microbiome functional diversity features, wherein the behavior characterization model is associated with the human behavior condition;
   generating a human behavior characterization of the human behavior condition for a user based on the behavior characterization model; and
   providing a therapy to the user for the human behavior condition based on the human behavior characterization.

2. The method of claim 1, wherein generating the microorganism sequence dataset comprises:
   identifying a primer type compatible with a genetic target associated with the human behavior condition; and
   generating the microorganism sequence dataset for the set of subjects based on the primer type and the microorganism nucleic acids, and
   wherein the therapy enables selective modulation of a microbiome of the user in relation to at least one of a population size of a desired taxon and a desired microbiome function.

3. The method of claim 2, wherein generating the microorganism sequence dataset comprises performing experimental methods to generate at least one of metagenomic and metatranscriptomic libraries from the microorganism nucleic acids based on the experimental methods, and performing metagenomics and metatranscriptomics analysis to identify genetic targets associated with the human behavior condition.

4. The method of claim 2, wherein generating the microorganism sequence dataset comprises performing amplification operations, comprising singleplex and multiplex amplifications, directly from the microorganism nucleic acids using the primer type compatible with the genetic target associated with the human behavior condition.

5. The method of claim 4, wherein generating the microorganism sequence dataset based on the primer type and the microorganism nucleic acids comprises:
   fragmenting the microorganism nucleic acids; and
   performing multiplex amplification with the fragmented microorganism nucleic acids based on the primer type compatible with the genetic target associated with the human behavior condition.

6. The method of claim 1, further comprising after providing the therapy:
   collecting a post-therapy sample from the user;
   collecting a supplementary dataset from the user, wherein the supplementary dataset describes user behavior associated with the human behavior condition;
   generating a post-therapy human behavior characterization of the human behavior condition for the user based on post-therapy microbiome features derived from the post-therapy sample; and
   promoting an updated therapy to the user for the human behavior condition based on the post-therapy human behavior characterization and the supplementary dataset.

7. The method of claim 6, wherein the human behavior condition comprises at least one of a caffeine consumption condition, an alcohol consumption condition, a menopause condition, an exercise condition, and a probiotics condition, and wherein promoting the updated therapy to the user comprises promoting at least one of a probiotic therapy and a prebiotic therapy to the user based on the post-therapy human behavior characterization and the supplementary dataset, and wherein the at least one of the probiotic therapy and the prebiotic therapy is associated with at least one of: *Collinsella aerofaciens, Parabacteroides distasonis, Odoribacter splanchnicus, Faecalibacterium prausnitzii, Blautia luti, Subdoligranulum variabile, Bacteroides thetaiotaomicron, Parabacteroides merdae, Roseburia inulinivorans, Flavonifractor plautii, Streptococcus thermophilus, Sutterella wadsworthensis, Roseburia hominis, Bacteroides vulgatus, Bacteroides caccae, Phascolarctobacterium faecium, Bacteroides fragilis, Megamonas funiformis, Parasutterella excrementihominis, Blautia* sp. YHC-4, *Bifidobacteria bifidum, Bifidobacteria infantis, Lactobacillus rhamnosus, Lactococcus lactis, Lactobacillus plantarum, Lactobacillus acidophilus, Lactobacillus casei, Bacillus polyfermenticus,* Lactobacillaceae (Family), Clostridia (Class) Clostridiales (Order), *Blautia glucerasea, Erysipelatoclostridium ramosum, Dialister propionicifaciens.*

8. The method of claim 1, wherein generating the human behavior characterization of the human behavior condition based on the behavior characterization model comprises applying at least one of a machine learning approach, a parameter optimization approach, a statistical test, and a dimension reduction approach, wherein the at least one of the set of microbiome composition diversity features and the set of microbiome functional diversity features is associated with microorganisms collected at least at one of a gut site, a skin site, a nose site, a mouth site, and a genitals site.

9. The method of claim 8, wherein generating the human behavior characterization comprises generating the human behavior characterization based on the behavior characterization model and a set of user microbiome features for the user, wherein the set of user microbiome features is associated with at least one of: presence of a microbiome feature from the set of user microbiome features, absence of the microbiome feature from the set of user microbiome features, relative abundance of different taxonomic groups associated with the human behavior condition, a ratio between at least two microbiome features associated with the different taxonomic groups, interactions between the different taxonomic groups, and phylogenetic distance between the different taxonomic groups.

10. The method of claim 1, wherein the human behavior condition comprises a caffeine consumption condition, wherein the set of microbiome composition diversity features is associated with at least one of *Acidaminococcus*

(genus), Actinobacteria (Class), Actinobacteria (Phylum), Actinomycetales (Order), *Alistipes putredinis* (Species), *Allisonella* (genus), *Allisonella histaminiformans* (species), *Anaerotruncus* (Genus), Bacillales (order), Bacteroidaceae (Family), Bacteroidales (Order), *Bacteroides* (Genus), *Bacteroides acidifaciens* (Species), *Bacteroides coprocola* (species), *Bacteroides fragilis* (Species), *Bacteroides massiliensis* (species), *Bacteroides thetaiotaomicron* (Species), *Bacteroides vulgatus* (Species), Bacteroidetes (Phylum) and Proteobacteria (Phylum), Bacteroidia (Class), Betaproteobacteria (Class), *Blautia faecis* (Species), *Blautia luti* (Species), Burkholderiales (Order), *Butyricimonas* (Genus), *Butyricimonas* sp. JCM 18677 (species), *Butyricimonas virosa* (species), *Catenibacterium* (Genus), *Catenibacterium mitsuokai* (species), *Cloacibacillus* (genus), *Cloacibacillus evryensis* (species), Clostridia (Class), Clostridiales (Order), *Clostridium* (Genus), *Collinsella* (Genus), *Collinsella aerofaciens* (species), Coriobacteriaceae (Family), Coriobacteriales (Order), Deltaproteobacteria (Class), *Desulfovibrio* (genus), *Desulfovibrio piger* (species), Desulfovibrionaceae (family), Desulfovibrionales (order), *Dialister invisus* (species), *Dorea* (Genus), *Dorea formicigenerans* (Species), *Dorea longicatena* (species), *Eggerthella* (Genus), *Enterobacter* (Genus), *Enterorhabdus* (genus), *Erysipelatoclostridium ramosum* (Species), Erysipelotrichaceae (Family), Erysipelotrichales (Order), Erysipelotrichia (Class), Euryarchaeota (phylum), *Faecalibacterium* (Genus), *Faecalibacterium prausnitzii* (Species), *Finegoldia* (Genus), Firmicutes (Phylum), Flavobacteriia (Class), *Flavonifractor plautii* (Species), *Fusicatenibacter saccharivorans* (species), *Fusobacterium periodonticum* (species), *Fusobacterium* sp. CM21 (species), *Fusobacterium* sp. CM22 (species), Gammaproteobacteria (Class), *Haemophilus* (Genus), *Haemophilus parainfluenzae* (Species), *Howardella* (genus), *Howardella ureilytica* (species), *Kluyvera* (Genus), *Lachnospira* (genus), Methanobacteria (Class), Methanobacteriaceae (family), Methanobacteriales (order), *Methanobrevibacter* (Genus), *Methanobrevibacter smithii* (Species), *Moryella* (Genus), Negativicutes (Class), *Oscillospira* (Genus), *Parabacteroides merdae* (Species), *Parvimonas* (genus), *Parvimonas micra* (species), *Peptococcus* (genus), *Peptostreptococcus stomatis* (species), *Phascolarctobacterium* (Genus), *Prevotella* sp. WAL 2039G (species), Prevotellaceae (family), Puniceicoccales (Order), *Roseburia* (Genus), *Rothia dentocariosa* (species), Ruminococcaceae (Family), *Sarcina* (Genus), *Selenomonas* (genus), Staphylococcaceae (family), *Staphylococcus* (genus), *Staphylococcus* sp. C912 (species), *Subdoligranulum* (Genus), *Subdoligranulum variabile* (Species), Sutterellaceae (Family), Synergistaceae (family), Synergistales (order), Synergistetes (phylum), Synergistia (class), *Veillonella* (Genus), *Veillonella* sp. MSA12 (species), and *Collinsella aerofaciens* (Species), and wherein the set of microbiome functional diversity features is associated with at least one of Metabolism (KEGG2), Transport and Catabolism (KEGG2), Environmental Adaptation (KEGG2), Glycan Biosynthesis and Metabolism (KEGG2), Signaling Molecules and Interaction (KEGG2), Cellular Processes and Signaling (KEGG2), Translation (KEGG2), Metabolism of Other Amino Acids (KEGG2), Poorly Characterized (KEGG2), Carbohydrate Metabolism (KEGG2), Cell Motility (KEGG2), Transcription (KEGG2), Genetic Information Processing (KEGG2), Membrane Transport (KEGG2), Infectious Diseases (KEGG2), Lipid Metabolism (KEGG2), Replication and Repair (KEGG2), Nervous System (KEGG2), Energy Metabolism (KEGG2), Enzyme Families (KEGG2), Nucleotide Metabolism (KEGG2), Nitrogen metabolism (KEGG3), Ribosome Biogenesis (KEGG3), Pores ion channels (KEGG3), Membrane and intracellular structural molecules (KEGG3), Phenylalanine metabolism (KEGG3), Ascorbate and aldarate metabolism (KEGG3), Plant-pathogen interaction (KEGG3), Lysosome (KEGG3), Glycosaminoglycan degradation (KEGG3), Aminoacyl-tRNA biosynthesis (KEGG3), Lipopolysaccharide biosynthesis proteins (KEGG3), Geraniol degradation (KEGG3), Translation proteins (KEGG3), Other glycan degradation (KEGG3), Citrate cycle (TCA cycle) (KEGG3), Other ion-coupled transporters (KEGG3), Biosynthesis and biodegradation of secondary metabolites (KEGG3), Carbon fixation pathways in prokaryotes (KEGG3), Peptidoglycan biosynthesis (KEGG3), Glutathione metabolism (KEGG3), Toluene degradation (KEGG3), Cell motility and secretion (KEGG3), Glycerophospholipid metabolism (KEGG3), Inorganic ion transport and metabolism (KEGG3), Thiamine metabolism (KEGG3), Energy metabolism (KEGG3), Glycosphingolipid biosynthesis—ganglio series (KEGG3), RNA polymerase (KEGG3), Polycyclic aromatic hydrocarbon degradation (KEGG3), Cytoskeleton proteins (KEGG3), Inositol phosphate metabolism (KEGG3), Cellular antigens (KEGG3), Glycosphingolipid biosynthesis—globo series (KEGG3), Penicillin and cephalosporin biosynthesis (KEGG3), Ubiquinone and other terpenoid-quinone biosynthesis (KEGG3), Peroxisome (KEGG3), Pantothenate and CoA biosynthesis (KEGG3), Base excision repair (KEGG3), Others (KEGG3), Terpenoid backbone biosynthesis (KEGG3), Ribosome biogenesis in eukaryotes (KEGG3), Type II diabetes mellitus (KEGG3), Amino acid metabolism (KEGG3), Oxidative phosphorylation (KEGG3), Bacterial chemotaxis (KEGG3), Lysine biosynthesis (KEGG3), Pentose and glucuronate interconversions (KEGG3), Signal transduction mechanisms (KEGG3), Chromosome (KEGG3), Sporulation (KEGG3), Sulfur metabolism (KEGG3), Ribosome (KEGG3), Phenylalanine, tyrosine and tryptophan biosynthesis (KEGG3), Amino acid related enzymes (KEGG3), Sphingolipid metabolism (KEGG3), Valine, leucine and isoleucine degradation (KEGG3), Function unknown (KEGG3), D-Alanine metabolism (KEGG3), Glycosyltransferases (KEGG3), Transcription factors (KEGG3), Taurine and hypotaurine metabolism (KEGG3), Glyoxylate and dicarboxylate metabolism (KEGG3), Transporters (KEGG3), Other transporters (KEGG3), Aminobenzoate degradation (KEGG3), Butirosin and neomycin biosynthesis (KEGG3), Carbohydrate metabolism (KEGG3), Translation factors (KEGG3), ABC transporters (KEGG3), Replication, recombination and repair proteins (KEGG3), Bacterial toxins (KEGG3), Nucleotide excision repair (KEGG3), Cell division (KEGG3), Nicotinate and nicotinamide metabolism (KEGG3), Amino sugar and nucleotide sugar metabolism (KEGG3), Glycerolipid metabolism (KEGG3), Biosynthesis of vancomycin group antibiotics (KEGG3), Type I diabetes mellitus (KEGG3), DNA repair and recombination proteins (KEGG3), Lipid metabolism (KEGG3), Retinol metabolism (KEGG3), Glutamatergic synapse (KEGG3), Primary immunodeficiency (KEGG3), Photosynthesis (KEGG3), Ethylbenzene degradation (KEGG3), Cysteine and methionine metabolism (KEGG3), Methane metabolism (KEGG3), Photosynthesis proteins (KEGG3), Lysine degradation (KEGG3), Biotin metabolism (KEGG3), Tuberculosis (KEGG3), Cell cycle—*Caulobacter* (KEGG3), Fructose and mannose metabolism (KEGG3), Galactose metabolism (KEGG3), Benzoate degradation (KEGG3), beta-Alanine metabolism (KEGG3), Protein folding and associated processing (KEGG3), Pyrimidine metabolism (KEGG3), Valine, leucine and isoleucine biosynthesis (KEGG3), Homologous recombination (KEGG3), Starch and sucrose metabolism (KEGG3), Limonene and pinene degradation (KEGG3), Protein export (KEGG3), Chaperones and folding catalysts (KEGG3), Folate biosynthesis (KEGG3).

11. The method of claim 1, wherein the human behavior condition comprises an alcohol consumption condition, wherein the set of microbiome composition diversity features is associated with at least one of *Collinsella aerofaciens* (Species), *Parabacteroides distasonis* (Species), *Odoribacter splanchnicus* (Species), *Faecalibacterium prausnitzii* (Species), *Blautia luti* (Species), *Subdoligranulum variabile* (Species), *Bacteroides thetaiotaomicron* (Species), *Parabacteroides merdae* (Species), *Roseburia inulinivorans* (Species), *Flavonifractor plautii* (Species), *Streptococcus thermophilus* (Species), *Sutterella wadsworthensis* (Species), *Roseburia hominis* (Species), Clostridiales Family XIII. Incertae Sedis (Family), Coriobacteriaceae (Family), Acidaminococcaceae (Family), Lactobacillaceae (Family), Prevotellaceae (Family), Sutterellaceae (Family), Desulfovibrionaceae (Family), Enterobacteriaceae (Family), Clostridiales Family XI. Incertae Sedis (Family), Verrucomicrobiaceae (Family), Oscillospiraceae (Family), Coriobacteriales (Order), Selenomonadales (Order), Burkholderiales (Order), Desulfovibrionales (Order), Enterobacteriales (Order), Verrucomicrobiales (Order), Actinobacteria (Class), Negativicutes (Class), Betaproteobacteria (Class), Deltaproteobacteria (Class), Verrucomicrobiae (Class), Gammaproteobacteria (Class), Actinobacteria (Phylum), Proteobacteria (Phylum) and Verrucomicrobia (Phylum), Acidobacteria (phylum), Bacteroidetes (phylum), Candidatus Saccharibacteria (phylum), Chloroflexi (phylum), Deinococcus-Thermus (phylum), Euryarchaeota (phylum), Fibrobacteres (phylum), Streptophyta (phylum), Synergistetes (phylum), Verrucomicrobia (phylum), Acidobacteriia (class), Bacteroidia (class), Cytophagia (class), Deinococci (class), Erysipelotrichia (class), Fibrobacteria (class), Flavobacteriia (class), Methanobacteria (class), Sphingobacteriia (class), Synergistia (class), Actinomycetales (order), Anaeroplasmatales (order), Bacillales (order), Bacteroidales (order), Bifidobacteriales (order), Caulobacterales (order), Erysipelotrichales (order), Fibrobacterales (order), Flavobacteriales (order), Methanobacteriales (order), Mycoplasmatales (order), Neisseriales (order), Pasteurellales (order), Pseudomonadales (order), Rhizobiales (order), Rhodospirillales (order), Solanales (order), Sphingobacteriales (order), Sphingomonadales (order), Synergistales (order), Thermales (order), Thermoanaerobacterales (order), Actinomycetaceae (family), Aerococcaceae (family), Anaeroplasmataceae (family), Bacillaceae (family), Bacteroidaceae (family), Bifidobacteriaceae (family), Bradyrhizobiaceae (family), Carnobacteriaceae (family), Caulobacteraceae (family), Clostridiaceae (family), Comamonadaceae (family), Dermabacteraceae (family), Dietziaceae (family), Erysipelotrichaceae (family), Fibrobacteraceae (family), Flavobacteriaceae (family), Fusobacteriaceae (family), Lachnospiraceae (family), Methanobacteriaceae (family), Methylobacteriaceae (family), Microbacteriaceae (family), Micrococcaceae (family), Mycoplasmataceae (family), Neisseriaceae (family), Nocardiaceae (family), Oxalobacteraceae (family), Pasteurellaceae (family), Peptococcaceae (family), Peptostreptococcaceae (family), Planococcaceae (family), Porphyromonadaceae (family), Propionibacteriaceae (family), Pseudomonadaceae (family), Rhodobacteraceae (family), Rhodospirillaceae (family), Rikenellaceae (family), Ruminococcaceae (family), Sphingobacteriaceae (family), Sphingomonadaceae (family), Staphylococcaceae (family), Synergistaceae (family), Thermaceae (family), Thermoanaerobacteraceae (family), Veillonellaceae (family), *Abiotrophia* (genus), *Acetanaerobacterium* (genus), *Achromobacter* (genus), *Acidaminococcus* (genus), *Actinobaculum* (genus), *Actinomyces* (genus), *Adlercreutzia* (genus), *Aerococcus* (genus), *Akkermansia* (genus), *Alistipes* (genus), *Alloprevotella* (genus), *Anaeroplasma* (genus), *Anaerostipes* (genus), *Anaerotruncus* (genus), *Aquabacterium* (genus), *Asaccharospora* (genus), *Atopobium* (genus), *Bacillus* (genus), *Bacteroides* (genus), *Barnesiella* (genus), *Bifidobacterium* (genus), *Blautia* (genus), *Brachybacterium* (genus), *Bradyrhizobium* (genus), *Brevundimonas* (genus), *Burkholderia* (genus), *Butyricimonas* (genus), *Butyrivibrio* (genus), *Candidatus Saccharimonas* (genus), *Candidatus Soleaferrea* (genus), *Candidatus Stoquefichus* (genus), *Catonella* (genus), *Caulobacter* (genus), *Cellulosilyticum* (genus), *Chryseobacterium* (genus), *Clostridium* (genus), *Collinsella* (genus), *Coprobacillus* (genus), *Coprothermobacter* (genus), *Cronobacter* (genus), *Cruoricaptor* (genus), *Delftia* (genus), *Desulfovibrio* (genus), *Dialister* (genus), *Dielma* (genus), *Dorea* (genus), *Eggerthella* (genus), *Eisenbergiella* (genus), *Enterobacter* (genus), *Enterorhabdus* (genus), *Epulopiscium* (genus), *Eremococcus* (genus), *Erysipelatoclostridium* (genus), *Faecalibacterium* (genus), *Flavobacterium* (genus), *Flavonifractor* (genus), *Fusicatenibacter* (genus), *Fusobacterium* (genus), *Gelria* (genus), *Gordonibacter* (genus), *Granulicatella* (genus), *Haemophilus* (genus), *Herbaspirillum* (genus), *Hespellia* (genus), *Holdemania* (genus), *Intestinibacter* (genus), *Klebsiella* (genus), *Kluyvera* (genus), *Lachnospira* (genus), *Lactobacillus* (genus), *Lactonifactor* (genus), *Megamonas* (genus), *Megasphaera* (genus), *Methanosphaera* (genus), *Methylobacterium* (genus), *Moraxella* (genus), *Moryella* (genus), *Mycoplasma* (genus), *Neisseria* (genus), *Odoribacter* (genus), *Oscillibacter* (genus), *Pantoea* (genus), *Papillibacter* (genus), *Parabacteroides* (genus), *Parvimonas* (genus), *Pasteurella* (genus), *Pedobacter* (genus), *Pelomonas* (genus), *Peptoclostridium* (genus), *Peptococcus* (genus), *Phascolarctobacterium* (genus), *Planomicrobium* (genus), *Porphyromonas* (genus), *Prevotella* (genus), *Propionibacterium* (genus), *Pseudobutyrivibrio* (genus), *Pseudoclavibacter* (genus), *Pseudoflavonifractor* (genus), *Pseudomonas* (genus), *Ralstonia* (genus), *Rhodobacter* (genus), *Rhodococcus* (genus), *Romboutsia* (genus), *Roseburia* (genus), *Roseomonas* (genus), *Rothia* (genus), *Sarcina* (genus), *Selenomonas* (genus), *Senegalimassilia* (genus), *Shuttleworthia* (genus), *Sphingobacterium* (genus), *Sphingomonas* (genus), *Staphylococcus* (genus), *Stomatobaculum* (genus), *Streptobacillus* (genus), *Streptococcus* (genus), *Subdoligranulum* (genus), *Succinatimonas* (genus), *Sutterella* (genus), *Syntrophococcus* (genus), *Terrisporobacter* (genus), *Tessaracoccus* (genus), *Thalassospira* (genus), *Turicibacter* (genus), *Varibaculum* (genus), *Veillonella* (genus), *Abiotrophia defectiva* (species), *Achromobacter xylosoxidans* (species), *Acidaminococcus intestini* (species), *Acidaminococcus* sp. D21 (species), *Acinetobacter* sp. 511B (species), *Acinetobacter* sp. S2 (2009) (species), *Actinobaculum schaalii* (species), *Actinomyces meyeri* (species), *Actinomyces odontolyticus* (species), *Actinomyces* sp. oral strain Hal-1065 (species), *Actinomyces* sp. oral taxon 175 (species), *Actinomyces viscosus* (species), *Adlercreutzia equolifaciens* (species), *Aerosphaera taetra* (species), *Akkermansia muciniphila* (species), *Alistipes finegoldii* (species), *Alistipes indistinctus* (species), *Alistipes putredinis* (species), *Alistipes shahii* (species), *Alistipes* sp. 627

(species), *Alistipes* sp. EBA6-25cl2 (species), *Alistipes* sp. HGB5 (species), *Alistipes* sp. RMA 9912 (species), *Anaerococcus hydrogenalis* (species), *Anaerococcus* sp. 9401487 (species), *Anaeroglobus geminatus* (species), *Anaerostipes hadrus* (species), *Anaerostipes* sp. 5_1_63FAA (species), *Anaerotruncus colihominis* (species), *Anaerovibrio* sp. 765 (species), *Arcanobacterium* sp. NML 06501 (species), *Asaccharospora irregularis* (species), *Atopobium* sp. F0209 (species), *Atopobium* sp. S3PFAA1-4 (species), *Bacteroides acidifaciens* (species), *Bacteroides* caccae (species), *Bacteroides* chinchillae (species), *Bacteroides* dorei (species), *Bacteroides* eggerthii (species), *Bacteroides* finegoldii (species), *Bacteroides fragilis* (species), *Bacteroides massiliensis* (species), *Bacteroides* nordii (species), *Bacteroides* ovatus (species), *Bacteroides* plebeius (species), *Bacteroides* salyersiae (species), *Bacteroides* sp. 35AE37 (species), *Bacteroides* sp. AR20 (species), *Bacteroides* sp. AR29 (species), *Bacteroides* sp. D22 (species), *Bacteroides* sp. DJF_B097 (species), *Bacteroides* sp. EBA5-17 (species), *Bacteroides* sp. J1511 (species), *Bacteroides* sp. S-17 (species), *Bacteroides* sp. SLC1-38 (species), *Bacteroides* sp. XB12B (species), *Bacteroides* stercoris (species), *Bacteroides uniformis* (species), *Bacteroides* vulgatus (species), *Barnesiella intestinihominis* (species), *Bergeyella* sp. AF14 (species), *Bifidobacterium adolescentis* (species), *Bifidobacterium breve* (species), *Bifidobacterium* kashiwanohense (species), *Bifidobacterium longum* (species), *Bifidobacterium pseudocatenulatum* (species), *Bifidobacterium* sp. MSX5B (species), *Bifidobacterium* stercoris (species), *Bilophila* sp. 4_1_30 (species), *Bilophila wadsworthia* (species), *Blautia coccoides* (species), *Blautia faecis* (species), *Blautia* sp. YHC-4 (species), *Blautia stercoris* (species), *Blautia wexlerae* (species), *Brachybacterium* sp. NIO-27 (species), *Brevundimonas* sp. FXJ8.080 (species), *Butyricimonas* sp. JCM 18676 (species), *Butyricimonas* sp. JCM 18677 (species), *Butyricimonas virosa* (species), *Butyrivibrio crossotus* (species), *Campylobacter gracilis* (species), *Campylobacter* sp. FOBRC15 (species), *Capnocytophaga sputigena* (species), *Catonella morbi* (species), *Chryseobacterium hominis* (species), *Coprobacillus* sp. D6 (species), *Corynebacterium canis* (species), *Corynebacterium* sp. (species), *Cronobacter sakazakii* (species), *Cruoricaptor ignavus* (species), *Delftia* sp. BN-SKY3 (species), *Desulfovibrio piger* (species), *Dialister invisus* (species), *Dialister micraerophilus* (species), *Dialister propionicifaciens* (species), *Dialister* sp. E2_20 (species), *Dialister* sp. S4-23 (species), *Dielma fastidiosa* (species), *Dorea formicigenerans* (species), *Dorea longicatena* (species), *Eggerthella lenta* (species), *Eggerthella* sp. HGA1 (species), *Eisenbergiella tayi* (species), *Enterococcus faecalis* (species), *Eremococcus coleocola* (species), *Erysipelatoclostridium ramosum* (species), *Faecalibacterium* sp. canine oral taxon 147 (species), *Finegoldia magna* (species), *Finegoldia* sp. S9 AA1-5 (species), *Flavobacterium ceti* (species), *Fusicatenibacter saccharivorans* (species), *Fusobacterium mortiferum* (species), *Fusobacterium periodonticum* (species), *Fusobacterium ulcerans* (species), *Gemella sanguinis* (species), *Gemella* sp. 933-88 (species), *Gordonibacter pamelaeae* (species), *Granulicatella elegans* (species), *Haemophilus parainfluenzae* (species), *Herbaspirillum huttiense* (species), *Herbaspirillum seropedicae* (species), *Holdemania filiformis* (species), *Intestinimonas butyriciproducens* (species), *Janibacter* sp. M3-5 (species), *Klebsiella* sp. SOR89 (species), *Kluyvera georgiana* (species), *Kocuria* sp. FXJ6.339 (species), *Kocuria* sp. M1-36 (species), *Lachnoanaerobaculum* sp. MSX33 (species), *Lachnospira pectinoschiza* (species), *Lactobacillus johnsonii* (species), *Lactobacillus* sp. 7_1_47FAA (species), *Lactobacillus* sp. Akhmroi (species), *Lactonifactor longoviformis* (species), *Leptotrichia hofstadii* (species), *Leptotrichia hongkongensis* (species), *Leptotrichia shahii* (species), *Megamonas funiformis* (species), *Megamonas rupellensis* (species), *Methylobacterium* sp. PDD-23b-14 (species), *Mogibacterium* sp. CM96 (species), *Mycobacterium* sp. KNUC297 (species), *Neisseria* sp. CCUG45853 (species), *Neisseria* sp. SMC-A9199 (species), *Olsenella* sp. S9 HS-6 (species), *Pantoea* sp. CWB304 (species), *Parabacteroides johnsonii* (species), *Parabacteroides* sp. 157 (species), *Paraprevotella clara* (species), *Parvimonas* sp. oral taxon 393 (species), *Pasteurella pneumotropica* (species), *Pedobacter heparinus* (species), *Pelomonas aquatica* (species), *Peptoclostridium difficile* (species), *Peptoniphilus* sp. gpac148 (species), *Peptoniphilus* sp. oral taxon 375 (species), *Peptoniphilus* sp. oral taxon 836 (species), *Peptoniphilus* sp. S3PFAA2-10 (species), *Phascolarctobacterium* sp. 377 (species), *Phascolarctobacterium succinatutens* (species), *Porphyromonas* uenonis (species), *Prevotella disiens* (species), *Prevotella intermedia* (species), *Prevotella oulorum* (species), *Prevotella* sp. WAL 2039G (species), *Propionibacterium acnes* (species), *Propionibacterium* sp. KPL1844 (species), *Pseudoflavonifractor capillosus* (species), *Pseudomonas brenneri* (species), *Pseudomonas* sp. GmFRB023 (species), *Pseudomonas* sp. KB23 (species), *Roseburia* faecis (species), *Roseburia intestinalis* (species), *Roseburia* sp. 11SE39 (species), *Roseburia* sp. DJF_RR73 (species), *Rothia dentocariosa* (species), *Rothia mucilaginosa* (species), *Selenomonas* sp. CM52 (species), *Slackia exigua* (species), *Sphingobacterium spiritivorum* (species), *Sphingomonas* sp. 24T (species), *Sphingomonas* sp. 540 (species), *Staphylococcus* sp. C912 (species), *Staphylococcus* sp. L10 (species), *Stenotrophomonas* sp. KITS-1 (species), *Stenotrophomonas* sp. UYSO33 (species), *Streptococcus dysgalactiae* (species), *Streptococcus equinus* (species), *Streptococcus gordonii* (species), *Streptococcus parasanguinis* (species), *Streptococcus* sp. 2011_Oral_MS_A3 (species), *Streptococcus* sp. BS35a (species), *Streptococcus* sp. oral taxon G59 (species), *Succinatimonas hippei* (species), *Sutterella* sp. 252 (species), *Terrisporobacter glycolicus* (species), *Tessaracoccus* sp. IPBSL-7 (species), *Tessaracoccus* sp. SL014B-79A (species), *Turicibacter sanguinis* (species), *Veillonella atypica* (species), *Veillonella rogosae* (species), *Veillonella* sp. 6_1_27 (species), *Veillonella* sp. AS16 (species), *Veillonella* sp. oral taxon 780 (species), and wherein the set of microbiome functional diversity features is associated with at least one of Metabolism (KEGG2), Energy Metabolism (KEGG2), Xenobiotics Biodegradation and Metabolism (KEGG2), Environmental Adaptation (KEGG2), Cell Motility (KEGG2), Lipid Metabolism (KEGG2), Carbohydrate Metabolism (KEGG2), Enzyme Families (KEGG2), Nervous System (KEGG2), Transport and Catabolism (KEGG2), Poorly Characterized (KEGG2), Signaling Molecules and Interaction (KEGG2), Selenocompound metabolism (KEGG3), Propanoate metabolism (KEGG3), Fatty acid biosynthesis (KEGG3), Primary immunodeficiency (KEGG3), Phenylalanine metabolism (KEGG3), Carbon fixation pathways in prokaryotes (KEGG3), Oxidative phosphorylation (KEGG3), Plant-pathogen interaction (KEGG3), Pyruvate metabolism (KEGG3), Nitrogen metabolism (KEGG3), Inositol phosphate metabolism (KEGG3), Ascorbate and aldarate metabolism (KEGG3), Lipid biosynthesis proteins (KEGG3), Penicillin and cephalosporin biosynthesis (KEGG3), Bacterial chemotaxis (KEGG3), Type I diabetes mellitus (KEGG3), Biosynthesis and biodegradation of secondary metabolites (KEGG3), General function prediction only (KEGG3), Butanoate metabolism (KEGG3), Biosynthesis of vancomycin group antibiotics (KEGG3), Glyoxylate and dicarboxylate metabolism (KEGG3), Geraniol degradation (KEGG3), Polycyclic aromatic hydrocarbon degradation (KEGG3), Others (KEGG3), Other transporters (KEGG3), Huntington's disease (KEGG3), Biosynthesis of siderophore group nonribosomal peptides (KEGG3), Citrate cycle (TCA cycle) (KEGG3), Lysosome (KEGG3), Secretion system (KEGG3), Glutamatergic synapse (KEGG3), Energy metabolism (KEGG3), Protein kinases (KEGG3), Pentose and glucuronate interconversions (KEGG3), Nicotinate and nicotinamide metabolism (KEGG3), Ribosome Biogenesis (KEGG3), Fatty acid metabolism (KEGG3), Chromosome (KEGG3), Cysteine and methionine metabolism (KEGG3), Glycerophospholipid metabolism (KEGG3), Riboflavin metabolism (KEGG3), Terpenoid backbone biosynthesis (KEGG3), Aminobenzoate degradation (KEGG3), Amino acid metabolism (KEGG3), Fructose and mannose metabolism (KEGG3), Glycosaminoglycan degradation (KEGG3), Chloroalkane and chloroalkene degradation (KEGG3), Pores ion channels (KEGG3), Carbon fixation in photosynthetic organisms (KEGG3), Benzoate degradation (KEGG3), Sulfur metabolism (KEGG3), Lipoic acid metabolism (KEGG3), Biosynthesis of unsaturated fatty acids (KEGG3), Tryptophan metabolism (KEGG3).

12. The method of claim 1, wherein the human behavior condition comprises a probiotics condition, wherein the set of microbiome composition diversity features is associated with at least one of *Blautia luti* (Species), *Flavonifractor plautii* (Species), *Collinsella aerofaciens* (Species), *Blautia glucerasea* (Species), *Erysipelatoclostridium ramosum* (Species), *Dialister propionicifaciens* (Species), *Blautia* sp. YHC-4 (Species), *Bifidobacterium* (Genus), *Oscillospira* (Genus), *Dialister* (Genus), *Intestinimonas* (Genus), *Moryella* (Genus), *Collinsella* (Genus), *Bacteroides* (Genus), *Finegoldia* (Genus), *Dorea* (Genus), *Peptoniphilus* (Genus), *Subdoligranulum* (Genus), *Anaerotruncus* (Genus), *Corynebacterium* (Genus), *Roseburia* (Genus), *Porphyromonas* (Genus), *Flavonifractor* (Genus), *Faecalibacterium* (Genus), *Lactobacillus* (Genus), *Anaerococcus* (Genus), *Pseudoflavonifractor* (Genus), *Phascolarctobacterium* (Genus), *Sarcina* (Genus), Bifidobacteriaceae (Family), Oscillospiraceae (Family), Bacteroidaceae (Family), Veillonellaceae (Family), Ruminococcaceae (Family), Lactobacillaceae (Family), Coriobacteriaceae (Family), Clostridiales Family XI. Incertae Sedis (Family), Streptococcaceae (Family), Corynebacteriaceae (Family), Prevotellaceae (Family), Flavobacteriaceae (Family), Bifidobacteriales (Order), Bacteroidales (Order), Clostridiales (Order), Coriobacteriales (Order), Actinomycetales (Order), Actinobacteria (Class), Bacteroidia (Class), Clostridia (Class), Actinobacteria (Phylum), Bacteroidetes (Phylum), Firmicutes (Phylum), Proteobacteria (Phylum), Acidobacteria (phylum), Actinobacteria (phylum), Actinobacteria (phylum), Bacteroidetes (phylum), Bacteroidetes (phylum), Candidatus Saccharibacteria (phylum), Chloroflexi (phylum), Cyanobacteria (phylum), Cyanobacteria (phylum), Euryarchaeota (phylum), Firmicutes (phylum), Firmicutes (phylum), Lentisphaerae (phylum), Proteobacteria (phylum), Proteobacteria (phylum), Streptophyta (phylum), Streptophyta (phylum), Tenericutes (phylum), Tenericutes (phylum), Verrucomicrobia (phylum), Acidobacteriia (class), Acidobacteriia (class), Actinobacteria (class), Actinobacteria (class), Alphaproteobacteria (class), Anaerolineae (class), Bacteroidia (class), Bacteroidia (class), Betaproteobacteria (class), Clostridia (class), Clostridia (class), Deltaproteobacteria (class), Deltaproteobacteria (class), Epsilonproteobacteria (class), Erysipelotrichia (class), Flavobacteriia (class), Gammaproteobacteria (class), Lentisphaeria (class), Methanobacteria (class), Mollicutes (class), Mollicutes (class), Negativicutes (class), Opitutae (class), Verrucomicrobiae (class), Acholeplasmatales (order), Actinomycetales (order), Anaerolineales (order), Bacillales (order), Bacteroidales (order), Bacteroidales (order), Bifidobacteriales (order), Bifidobacteriales (order), Burkholderiales (order), Campylobacterales (order), Clostridiales (order), Clostridiales (order), Coriobacteriales (order), Desulfovibrionales (order), Desulfovibrionales (order), Enterobacteriales (order), Erysipelotrichales (order), Flavobacteriales (order), Methanobacteriales (order), Mycoplasmatales (order), Puniceicoccales (order), Rhodospirillales (order), Selenomonadales (order), Solanales (order), Solanales (order), Verrucomicrobiales (order), Acholeplasmataceae (family), Acidaminococcaceae (family), Actinomycetaceae (family), Anaerolineaceae (family), Bacillaceae (family), Bacillaceae (family), Bacteroidaceae (family), Bacteroidaceae (family), Bifidobacteriaceae (family), Bifidobacteriaceae (family), Brevibacteriaceae (family), Brevibacteriaceae (family), Brevibacteriaceae (family), Campylobacteraceae (family), Carnobacteriaceae (family), Carnobacteriaceae (family), Clostridiaceae (family), Clostridiales Family XI. Incertae Sedis (family), Coriobacteriaceae (family), Corynebacteriaceae (family), Desulfovibrionaceae (family), Desulfovibrionaceae (family), Enterobacteriaceae (family), Enterococcaceae (family), Enterococcaceae (family), Erysipelotrichaceae (family), Eubacteriaceae (family), Flavobacteriaceae (family), Lachnospiraceae (family), Lactobacillaceae (family), Leuconostocaceae (family), Methanobacteriaceae (family), Microbacteriaceae (family), Moraxellaceae (family), Mycoplasmataceae (family), Oscillospiraceae (family), Oscillospiraceae (family), Peptostreptococcaceae (family), Phyllobacteriaceae (family), Porphyromonadaceae (family), Prevotellaceae (family), Propionibacteriaceae (family), Propionibacteriaceae (family), Pseudomonadaceae (family; e.g., genital site), Rhodospirillaceae (family), Ruminococcaceae (family), Ruminococcaceae (family), Streptococcaceae (family), Sutterellaceae (family), Veillonellaceae (family), Verrucomicrobiaceae (family), Victivallaceae (family), *Abiotrophia* (genus), *Acholeplasma* (genus), *Acidaminococcus* (genus), *Adlercreutzia* (genus), *Adlercreutzia* (genus), *Akkermansia* (genus), *Allisonella* (genus), *Alloprevotella* (genus; e.g., genital site), *Anaerobacter* (genus), *Anaerococcus* (genus), *Anaerofilum* (genus), *Anaerofustis* (genus), *Anaerosporobacter* (genus), *Anaerotruncus* (genus), *Anaerotruncus* (genus), *Anaerovibrio* (genus), *Asteroleplasma* (genus), *Bacillus* (genus), *Bacteroides* (genus), *Bacteroides* (genus), *Barnesiella* (genus), *Barnesiella* (genus), *Bifidobacterium* (genus), *Bifidobacterium* (genus), *Bilophila* (genus), *Bilophila* (genus), *Brevibacterium* (genus), *Brevibacterium* (genus), *Brevibacterium* (genus), *Butyricicoccus* (genus), *Butyricimonas* (genus), *Butyricimonas* (genus), *Campylobacter* (genus), *Candidatus Soleaferrea* (genus), *Citrobacter* (genus), *Collinsella* (genus), *Collinsella* (genus), *Coprobacillus* (genus), *Corynebacterium* (genus), *Desulfovibrio* (genus), *Dialister* (genus), *Dialister* (genus), *Dielma* (genus), *Dielma* (genus), *Dolosigranulum* (genus), *Dorea* (genus), *Dorea* (genus), *Dysgonomonas* (genus), *Eggerthella* (genus), *Eggerthella* (genus), *Eisenbergiella* (genus), *Eisenbergiella* (genus), *Enterobacter* (genus; e.g., genital site), *Enterobacter* (genus), *Enterobacter* (genus), *Enterococcus* (genus), *Enterococcus* (genus), *Enterorhabdus* (genus), *Erysipelatoclostridium* (genus), *Eubac-* terium (genus), *Faecalibacterium* (genus), *Faecalibacterium* (genus), *Fastidiosipila* (genus), *Finegoldia* (genus), *Flavonifractor* (genus), *Fusicatenibacter* (genus), *Fusicatenibacter* (genus), *Gardnerella* (genus), *Gemella* (genus), *Gordonibacter* (genus), *Gordonibacter* (genus), *Granulicatella* (genus), *Hespellia* (genus), *Hespellia* (genus), *Holdemania* (genus), *Holdemania* (genus), *Howardella* (genus), *Howardella* (genus), *Intestinibacter* (genus), *Intestinibacter* (genus), *Intestinimonas* (genus), *Intestinimonas* (genus), *Klebsiella* (genus), *Lachnospira* (genus), *Lactobacillus* (genus), *Lactobacillus* (genus), *Lactococcus* (genus), *Lactonifactor* (genus), *Leuconostoc* (genus), *Marvinbryantia* (genus), *Megasphaera* (genus), *Megasphaera* (genus), *Methanobrevibacter* (genus), *Mitsuokella* (genus), *Mogibacterium* (genus), *Moraxella* (genus), *Moryella* (genus), *Moryella* (genus), *Murdochiella* (genus), *Odoribacter* (genus), *Odoribacter* (genus), *Oscillibacter* (genus), *Oscillospira* (genus), *Oscillospira* (genus), *Papillibacter* (genus), *Parabacteroides* (genus), *Parabacteroides* (genus), *Parasutterella* (genus), *Parvibacter* (genus), *Parvimonas* (genus), *Pasteurella* (genus), *Peptoniphilus* (genus), *Phascolarctobacterium* (genus), *Phascolarctobacterium* (genus), *Photobacterium* (genus), *Phyllobacterium* (genus), *Porphyromonas* (genus), *Prevotella* (genus), *Propionibacterium* (genus; e.g., genital site), *Propionibacterium* (genus), *Pseudoclavibacter* (genus), *Pseudoflavonifractor* (genus), *Pseudoflavonifractor* (genus), *Pseudomonas* (genus; e.g., genital site), *Psychrobacter* (genus), *Robinsoniella* (genus), *Robinsoniella* (genus), *Romboutsia* (genus), *Roseburia* (genus), *Roseburia* (genus), *Sarcina* (genus), *Sarcina* (genus), *Shuttleworthia* (genus), *Slackia* (genus), *Streptococcus* (genus), *Subdoligranulum* (genus), *Subdoligranulum* (genus), *Sutterella* (genus), *Sutterella* (genus), *Syntrophococcus* (genus), *Terrisporobacter* (genus), *Terrisporobacter* (genus), *Thalassospira* (genus), *Turicella* (genus), *Turicibacter* (genus), *Varibaculum* (genus), *Veillonella* (genus), *Victivallis* (genus), *Abiotrophia defectiva* (species), *Acidaminococcus fermentans* (species), *Acidaminococcus intestini* (species), *Acidaminococcus* sp. D21 (species), *Acinetobacter* sp. p-1 (species), *Adlercreutzia equolifaciens* (species), *Adlercreutzia equolifaciens* (species), *Akkermansia muciniphila* (species), *Alistipes finegoldii* (species), *Alistipes putredinis* (species), *Alistipes putredinis* (species), *Alistipes shahii* (species), *Alistipes* sp. HGB5 (species), *Alistipes* sp. NML05A004 (species), *Alistipes* sp. RMA 9912 (species), *Alistipes* sp. RMA 9912 (species), *Allisonella histaminiformans* (species), *Anaerococcus murdochii* (species), *Anaerococcus* sp. 8404299 (species), *Anaerococcus* sp. 9401487 (species), *Anaerococcus* sp. 9402080 (species), *Anaerococcus* sp. S9 PR-16 (species; e.g., genital site), *Anaerofustis stercorihominis* (species), *Anaerostipes butyraticus* (species), *Anaerostipes* sp. 3_2_56FAA (species), *Anaerostipes* sp. 3_2_56FAA (species), *Anaerostipes* sp. 494a (species), *Anaerostipes* sp. 5_1_63FAA (species), *Anaerostipes* sp. 5_1_63FAA (species), *Anaerotruncus colihominis* (species), *Anaerotruncus* sp. NML 070203 (species), *Arthrobacter* sp. (species), *Bacillus* sp. DHT-33 (species), *Bacteroides clarus* (species), *Bacteroides finegoldii* (species), *Bacteroides massiliensis* (species), *Bacteroides massiliensis* (species), *Bacteroides* nordii (species), *Bacteroides* plebeius (species), *Bacteroides* plebeius (species), *Bacteroides* sp. AR20 (species), *Bacteroides* sp. AR20 (species), *Bacteroides* sp. AR29 (species), *Bacteroides* sp. AR29 (species), *Bacteroides* sp. C13EG172 (species), *Bacteroides* sp. D22 (species), *Bacteroides* sp. D22 (species), *Bacteroides* sp. EBA5-17 (species), *Bacteroides* sp. SLC1-38 (species), *Bacteroides* sp. XB12B (species), *Bacteroides* sp. XB12B (species), *Bacteroides* stercoris (species), *Bacteroides* thetaiotaomicron (species), *Bacteroides* thetaiotaomicron (species), *Bacteroides* thetaiotaomicron (species), *Bacteroides uniformis* (species), *Bacteroides* vulgatus (species), *Bacteroides* vulgatus (species), *Barnesiella intestinihominis* (species), *Barnesiella intestinihominis* (species), *Barnesiella* sp. 177 (species), *Barnesiella viscericola* (species), *Bifidobacterium adolescentis* (species), *Bifidobacterium animalis* (species), *Bifidobacterium choerinum* (species), *Bifidobacterium* kashiwanohense (species), *Bifidobacterium longum* (species), *Bifidobacterium merycicum* (species), *Bifidobacterium merycicum* (species), *Bifidobacterium pseudocatenulatum* (species), *Bifidobacterium* sp. (species), *Bifidobacterium stercoris* (species), *Bifidobacterium stercoris* (species), *Bifidobacterium tsurumiense* (species), *Bilophila* sp. 4_1_30 (species), *Bilophila wadsworthia* (species), *Blautia faecis* (species), *Blautia glucerasea* (species), *Blautia glucerasea* (species), *Blautia glucerasea* (species), *Blautia hydrogenotrophica* (species), *Blautia hydrogenotrophica* (species), *Blautia luti* (species), *Blautia luti* (species), *Blautia* sp. Ser8 (species), *Blautia* sp. Ser8 (species), *Blautia* sp. YHC-4 (species), *Blautia* sp. YHC-4 (species), *Blautia wexlerae* (species), *Brevibacterium paucivorans* (species), *Butyricicoccus pullicaecorum* (species), *Butyricimonas virosa* (species), *Butyrivibrio* crossotus (species), *Campylobacter hominis* (species), *Catenibacterium mitsuokai* (species), *Citrobacter* sp. BW4 (species), *Collinsella aerofaciens* (species), *Collinsella aerofaciens* (species), *Collinsella intestinalis* (species), *Coprobacillus* sp. D6 (species), *Corynebacterium canis* (species), *Corynebacterium* epidermidicanis (species), *Corynebacterium* epidermidicanis (species), *Corynebacterium freiburgense* (species), *Corynebacterium mastitidis* (species), *Corynebacterium ulcerans* (species), *Desulfovibrio piger* (species), *Dialister invisus* (species), *Dialister micraerophilus* (species), *Dialister propionicifaciens* (species), *Dialister* sp. S4-23 (species), *Dialister succinatiphilus* (species), *Dielma fastidiosa* (species), *Dielma fastidiosa* (species), *Dolosigranulum pigrum* (species), *Dorea formicigenerans* (species), *Dorea formicigenerans* (species), *Dorea longicatena* (species), *Dorea longicatena* (species), *Dysgonomonas capnocytophagoides* (species), *Dysgonomonas oryzarvi* (species), *Eggerthella sinensis* (species), *Eggerthella* sp. HGA1 (species), *Eggerthella* sp. HGA1 (species), *Eisenbergiella tayi* (species), *Eisenbergiella tayi* (species), *Enterobacter* sp. BS2-1 (species; e.g., genital site), *Enterobacter* sp. BS2-1 (species), *Enterococcus* sp. C6I11 (species), *Enterococcus* sp. SI-4 (species), *Enterococcus ureasiticus* (species), *Erysipelatoclostridium ramosum* (species), *Erysipelatoclostridium ramosum* (species), *Eubacterium callanderi* (species), *Eubacterium* sp. SA11 (species), *Facklamia languida* (species), *Faecalibacterium prausnitzii* (species), *Faecalibacterium prausnitzii* (species), *Faecalibacterium* sp. canine oral taxon 147 (species), *Finegoldia* sp. S8 F7 (species; e.g., genital site), *Finegoldia* sp. S9 AA1-5 (species), *Flavonifractor plautii* (species), *Flavonifractor plautii* (species), *Fusicatenibacter saccharivorans* (species), *Fusicatenibacter saccharivorans* (species), *Fusobacterium mortiferum* (species), *Fusobacterium* sp. CM21 (species), *Fusobacterium varium* (species), *Gardnerella vaginalis* (species), *Gemella morbillorum* (species), *Gemella sanguinis* (species), *Gemella* sp. 933-88 (species), *Gemella* sp. 933-88 (species), *Gordonibacter pamelaeae* (species), *Gordonibacter pamelaeae* (species), *Granulicatella adiacens* (species), *Haemophilus influenzae* (species), *Holdemania filiformis* (species), *Holdemania filiformis* (species), *Howardella ureilytica* (species), *Howardella* ureilytica (species), *Intestinimonas butyriciproducens* (species), *Klebsiella* sp. SOR89 (species), *Lachnospira pectinoschiza* (species), *Lachnospira pectinoschiza* (species), *Lactobacillus* crispatus (species), *Lactobacillus* crispatus (species), *Lactobacillus delbrueckii* (species), *Lactobacillus fornicalis* (species), *Lactobacillus plantarum* (species), *Lactobacillus rhamnosus* (species), *Lactobacillus ruminis* (species), *Lactobacillus* ruminis (species), *Lactobacillus salivarius* (species), *Lactobacillus* sp. 7_1_47FAA (species; e.g., genital site), *Lactobacillus* sp. 7_1_47FAA (species), *Lactobacillus* sp. 7_1_47FAA (species), *Lactobacillus* sp. 7_1_47FAA (species), *Lactobacillus* sp. BL302 (species), *Lactobacillus* sp. S16 (species), *Lactobacillus* sp. TAB-22 (species), *Lactobacillus* sp. TAB-26 (species), *Lactobacillus* sp. TAB-30 (species), *Lactococcus* sp. MH5-2 (species), *Lactonifactor longoviformis* (species), *Lactonifactor longoviformis* (species), *Leuconostoc* sp. C714 (species), *Megasphaera elsdenii* (species), *Megasphaera* sp. S6-MB2 (species), *Methanobrevibacter smithii* (species), *Mitsuokella* sp. TM-10 (species), *Moraxella* sp. BB37 (species), *Moraxella* sp. BBN2P-02d (species), *Murdochiella asaccharolytica* (species), *Neisseria macacae* (species; e.g., genital site), *Neisseria* mucosa (species), *Neisseria* mucosa (species), *Odoribacter splanchnicus* (species), *Odoribacter splanchnicus* (species), *Parabacteroides distasonis* (species), *Parabacteroides goldsteinii* (species), *Parabacteroides merdae* (species), *Parabacteroides merdae* (species), *Parasutterella excrementihominis* (species), *Parvibacter caecicola* (species), *Parvimonas* sp. oral taxon 393 (species), *Pasteurella pneumotropica* (species), *Pediococcus* sp. MFC1 (species), *Peptococcus niger* (species), *Peptoniphilus* sp. 2002-2300004 (species), *Peptoniphilus* sp. gpac018A (species), *Peptoniphilus* sp. oral taxon 836 (species), *Phascolarctobacterium faecium* (species), *Phascolarctobacterium faecium* (species), *Photobacterium* sp. CAIM 866 (species), *Porphyromonas bennonis* (species), *Porphyromonas* sp. 2026 (species), *Porphyromonas* sp. 2026 (species), *Prevotella bivia* (species), *Prevotella buccalis* (species), *Prevotella disiens* (species), *Prevotella oris* (species), *Prevotella* sp. BV3C7 (species), *Prevotella timonensis* (species), *Pseudoclavibacter bifida* (species), *Pseudoclavibacter* sp. *Timone* (species), *Pseudoflavonifractor capillosus* (species), *Pseudoflavonifractor capillosus* (species), *Robinsoniella peoriensis* (species), *Roseburia faecis* (species), *Roseburia* faecis (species), *Roseburia hominis* (species), *Roseburia intestinalis* (species), *Roseburia inulinivorans* (species), *Roseburia inulinivorans* (species), *Roseburia* sp. 11SE39 (species), *Roseburia* sp. 11SE39 (species), *Roseburia* sp. 499 (species), *Slackia* sp. NATTS (species), *Slackia* sp. NATTS (species), *Staphylococcus* sp. WB18-16 (species), *Streptococcus* equinus (species), *Streptococcus* sp. 2011_Oral_MS_A3 (species; e.g., genital site), *Streptococcus* sp. 2011_Oral_MS_A3 (species), *Streptococcus* sp. oral taxon G59 (species; e.g., genital site), *Streptococcus* sp. oral taxon G63 (species), *Streptococcus thermophilus* (species), *Streptococcus thermophilus* (species), *Subdoligranulum variabile* (species), *Subdoligranulum variabile* (species), *Sutterella* sp. 252 (species), *Sutterella wadsworthensis* (species), *Turicella otitidis* (species), *Turicibacter sanguinis* (species), *Varibaculum cambriense* (species), *Veillonella* sp. 2011_Oral_VSA_D3 (species), *Veillonella* sp. AS16 (species), *Veillonella* sp. CM60 (species), and wherein the set of microbiome functional diversity features is associated with at least one of Carbohydrate Metabolism (KEGG2), Metabolism (KEGG2), Translation (KEGG2), Transport and Catabolism (KEGG2), Cellular Processes and Signaling (KEGG2), Genetic Information Processing (KEGG2), Glycan Biosynthesis and Metabolism (KEGG2), Environmental Adaptation (KEGG2), Signaling Molecules and Interaction (KEGG2), Metabolism of Other Amino Acids (KEGG2), Replication and Repair (KEGG2), Neurodegenerative Diseases (KEGG2), Biosynthesis of Other Secondary Metabolites (KEGG2), Energy Metabolism (KEGG2), Enzyme Families (KEGG2), Cell Motility (KEGG2), Poorly Characterized (KEGG2), Nucleotide Metabolism (KEGG2), Metabolic Diseases (KEGG2), Amino Acid Metabolism (KEGG2), Ribosome Biogenesis (KEGG3), Amyotrophic lateral sclerosis (ALS) (KEGG3), Nitrogen metabolism (KEGG3), Aminoacyl-tRNA biosynthesis (KEGG3), Amino sugar and nucleotide sugar metabolism (KEGG3), Glycosaminoglycan degradation (KEGG3), Other glycan degradation (KEGG3), Inositol phosphate metabolism (KEGG3), Lysosome (KEGG3), Ascorbate and aldarate metabolism (KEGG3), Type II diabetes mellitus (KEGG3), Huntington's disease (KEGG3), Translation proteins (KEGG3), Peptidoglycan biosynthesis (KEGG3), Fructose and mannose metabolism (KEGG3), Glycosphingolipid biosynthesis—ganglio series (KEGG3), Nucleotide excision repair (KEGG3), Pentose and glucuronate interconversions (KEGG3), Nicotinate and nicotinamide metabolism (KEGG3), Pores ion channels (KEGG3), Biosynthesis and biodegradation of secondary metabolites (KEGG3), Glycosphingolipid biosynthesis—globo series (KEGG3), Ribosome biogenesis in eukaryotes (KEGG3), Membrane and intracellular structural molecules (KEGG3), Penicillin and cephalosporin biosynthesis (KEGG3), Other ion-coupled transporters (KEGG3), Glycerophospholipid metabolism (KEGG3), Polycyclic aromatic hydrocarbon degradation (KEGG3), Lipopolysaccharide biosynthesis proteins (KEGG3), Lipoic acid metabolism (KEGG3), Geraniol degradation (KEGG3), Cell motility and secretion (KEGG3), Glyoxylate and dicarboxylate metabolism (KEGG3), Plant-pathogen interaction (KEGG3), Amino acid related enzymes (KEGG3), Galactose metabolism (KEGG3), Ribosome (KEGG3), Taurine and hypotaurine metabolism (KEGG3), Toluene degradation (KEGG3), Sphingolipid metabolism (KEGG3), Terpenoid backbone biosynthesis (KEGG3), Insulin signaling pathway (KEGG3), Others (KEGG3), DNA repair and recombination proteins (KEGG3), Oxidative phosphorylation (KEGG3), Base excision repair (KEGG3), Chromosome (KEGG3), Replication, recombination and repair proteins (KEGG3), Cellular antigens (KEGG3), RNA polymerase (KEGG3), Pantothenate and CoA biosynthesis (KEGG3), Cytoskeleton proteins (KEGG3), Amino acid metabolism (KEGG3), Lipid metabolism (KEGG3), Carbon fixation pathways in prokaryotes (KEGG3), Ubiquinone and other terpenoid-quinone biosynthesis (KEGG3), Homologous recombination (KEGG3), Peroxisome (KEGG3), Tuberculosis (KEGG3), Thiamine metabolism (KEGG3), Citrate cycle (TCA cycle) (KEGG3), Other transporters (KEGG3), Phosphonate and phosphinate metabolism (KEGG3), Cyanoamino acid metabolism (KEGG3), Lipopolysaccharide biosynthesis (KEGG3), Phenylalanine metabolism (KEGG3), Mismatch repair (KEGG3), Signal transduction mechanisms (KEGG3), Secretion system (KEGG3), Cysteine and methionine metabolism (KEGG3), Bisphenol degradation (KEGG3), Energy metabolism (KEGG3), Proteasome (KEGG3), Aminobenzoate degradation (KEGG3), Butanoate metabolism (KEGG3), Pentose phosphate pathway (KEGG3), Purine metabolism (KEGG3), Tyrosine metabolism (KEGG3), Biosynthesis of unsaturated fatty acids (KEGG3), Bacterial motility proteins (KEGG3), Inorganic ion transport and metabolism (KEGG3), D-Alanine metabolism (KEGG3), Sulfur metabolism (KEGG3), Pyrimidine metabolism (KEGG3), Streptomycin biosynthesis (KEGG3), Translation factors (KEGG3), Lysine biosynthesis (KEGG3), Valine, leucine and isoleucine degradation (KEGG3), General function prediction only (KEGG3), Protein processing in endoplasmic reticulum (KEGG3), Carbon fixation in photosynthetic organisms (KEGG3), Phosphatidylinositol signaling system (KEGG3), Bacterial chemotaxis (KEGG3), Phenylpropanoid biosynthesis (KEGG3), ABC transporters (KEGG3), Phosphotransferase system (PTS) (KEGG3), Bacterial toxins (KEGG3), Pyruvate metabolism (KEGG3), Ubiquitin system (KEGG3), Carbohydrate metabolism (KEGG3), Phenylalanine, tyrosine and tryptophan biosynthesis (KEGG3), Epithelial cell signaling in *Helicobacter pylori* infection (KEGG3), Photosynthesis (KEGG3), Polyketide sugar unit biosynthesis (KEGG3), DNA replication (KEGG3), RNA degradation (KEGG3) and Peptidases (KEGG3).

13. The method of claim 1, wherein the human behavior condition comprises a moderate physical exercise condition, wherein the set of microbiome composition diversity features is associated with at least one of Negativicutes (class), Clostridia (class), Bacteroidia (class), Verrucomicrobiae (class), Clostridiaceae (family), Bacteroidaceae (family), Acidaminococcaceae (family), Ruminococcaceae (family), Prevotellaceae (family), Oscillospiraceae (family), Bifidobacteriaceae (family), Lactobacillaceae (family), Coriobacteriaceae (family), Verrucomicrobiaceae (family), Veillonellaceae (family), *Clostridium* (genus), *Bacteroides* (genus), *Parabacteroides* (genus), *Bilophila* (genus), *Moryella* (genus), *Bifidobacterium* (genus), *Faecalibacterium* (genus), *Phascolarctobacterium* (genus), *Acidaminococcus* (genus), *Marvinbryantia* (genus), *Blautia* (genus), *Parasutterella* (genus), *Sarcina* (genus), *Akkermansia* (genus), Selenomonadales (order), Clostridiales (order), Bacteroidales (order), Bifidobacteriales (order), Coriobacteriales (order), Verrucomicrobiales (order), Bacteroidetes (phylum), Firmicutes (phylum), Verrucomicrobia (phylum), *Bacteroides* vulgatus (species), *Bacteroides* caccae (species), *Parabacteroides merdae* (species), *Phascolarctobacterium faecium* (species), *Parabacteroides distasonis* (species), *Flavonifractor plautii* (species), *Bacteroides fragilis* (species), *Parasutterella excrementihominis* (species), *Blautia* sp. YHC-4 (species), *Collinsella aerofaciens* (species), *Faecalibacterium prausnitzii* (species), and wherein the set of microbiome functional diversity features is associated with at least one of Translation (KEGG2), Cellular Processes and Signaling (KEGG2), Metabolism (KEGG2), Carbohydrate Metabolism (KEGG2), Replication and Repair (KEGG2), Cell Growth and Death (KEGG2), Signaling Molecules and Interaction (KEGG2), Environmental Adaptation (KEGG2), Poorly Characterized (KEGG2), Nucleotide Metabolism (KEGG2), Biosynthesis of Other Secondary Metabolites (KEGG2), Glycan Biosynthesis and Metabolism (KEGG2), Transport and Catabolism (KEGG2), Metabolism of Terpenoids and Polyketides (KEGG2), Cell Motility (KEGG2), Lipid Metabolism (KEGG2), Ribosome Biogenesis (KEGG3), Inorganic ion transport and metabolism (KEGG3), Amino acid metabolism (KEGG3), Ribosome (KEGG3), Amino acid related enzymes (KEGG3), Aminoacyl-tRNA biosynthesis (KEGG3), Ribosome biogenesis in eukaryotes (KEGG3), Galactose metabolism (KEGG3), RNA polymerase (KEGG3), Terpenoid backbone biosynthesis (KEGG3), Other ion-coupled transporters (KEGG3), Peptidoglycan biosynthesis (KEGG3), Translation factors (KEGG3), Homologous recombination (KEGG3), Phosphatidylinositol signaling system (KEGG3), DNA repair and recombination proteins (KEGG3), Amino sugar and nucleotide sugar metabolism (KEGG3), Biotin metabolism (KEGG3), Bacterial toxins (KEGG3), Others (KEGG3), Translation proteins (KEGG3), Pyrimidine metabolism (KEGG3), Other transporters (KEGG3), Alzheimer's disease (KEGG3), Tuberculosis (KEGG3), Sphingolipid metabolism (KEGG3), Other glycan degradation (KEGG3), Function unknown (KEGG3), Cell cycle—*Caulobacter* (KEGG3), Protein export (KEGG3), Glycosphingolipid biosynthesis—globo series (KEGG3), Nitrogen metabolism (KEGG3), Fructose and mannose metabolism (KEGG3), Carbohydrate metabolism (KEGG3), Nicotinate and nicotinamide metabolism (KEGG3), Pentose and glucuronate interconversions (KEGG3), Glyoxylate and dicarboxylate metabolism (KEGG3), Nucleotide excision repair (KEGG3), Plant-pathogen interaction (KEGG3), Chromosome (KEGG3), Mismatch repair (KEGG3), D-Alanine metabolism (KEGG3), DNA replication proteins (KEGG3), Photosynthesis proteins (KEGG3), Lysosome (KEGG3), Glycosaminoglycan degradation (KEGG3), Penicillin and cephalosporin biosynthesis (KEGG3), Photosynthesis (KEGG3), Vitamin metabolism (KEGG3), Ascorbate and aldarate metabolism (KEGG3), Base excision repair (KEGG3), Prenyltransferases (KEGG3), Biosynthesis of siderophore group nonribosomal peptides (KEGG3), Pantothenate and CoA biosynthesis (KEGG3), One carbon pool by folate (KEGG3), Pores ion channels (KEGG3), Bisphenol degradation (KEGG3), Starch and sucrose metabolism (KEGG3), DNA replication (KEGG3), Primary immunodeficiency (KEGG3), Membrane and intracellular structural molecules (KEGG3), Glycosphingolipid biosynthesis—ganglio series (KEGG3), Lipopolysaccharide biosynthesis proteins (KEGG3), Cyanoamino acid metabolism (KEGG3), Cell motility and secretion (KEGG3), Riboflavin metabolism (KEGG3), Drug metabolism—other enzymes (KEGG3), Glycosyltransferases (KEGG3), Taurine and hypotaurine metabolism (KEGG3), Sulfur metabolism (KEGG3), Biosynthesis and biodegradation of secondary metabolites (KEGG3).

14. The method of claim 1, wherein the human behavior condition comprises an extreme physical exercise condition, wherein the set of microbiome composition diversity features is associated with at least one of Negativicutes (class), Clostridia (class), Bacteroidia (class), Verrucomicrobiae (class), Deltaproteobacteria (class), Gammaproteobacteria (class), Clostridiaceae (family), Bacteroidaceae (family), Oscillospiraceae (family), Acidaminococcaceae (family), Veillonellaceae (family), Ruminococcaceae (family), Prevotellaceae (family), Bifidobacteriaceae (family), Lactobacillaceae (family), Verrucomicrobiaceae (family), Streptococcaceae (family), Desulfovibrionaceae (family), Porphyromonadaceae (family), Coriobacteriaceae (family), *Clostridium* (genus), *Bacteroides* (genus), *Parabacteroides* (genus), *Bilophila* (genus), *Marvinbryantia* (genus), *Bifidobacterium* (genus), *Akkermansia* (genus), *Acidaminococcus* (genus), *Megamonas* (genus), *Lachnospira* (genus), *Faecalibacterium* (genus), *Phascolarctobacterium* (genus), *Pseudobutyrivibrio* (genus), *Roseburia* (genus), *Anaerotruncus* (genus), *Veillonella* (genus), *Sarcina* (genus), *Parasutterella* (genus), Selenomonadales (order), Clostridiales (order), Bacteroidales (order), Bifidobacteriales (order), Verrucomicrobiales (order), Desulfovibrionales (order), Bacteroidetes (phylum), Firmicutes (phylum), Verrucomicrobia (phylum), *Bacteroides* vulgatus (species), *Parabacteroides merdae* (species), *Bacteroides caccae* (species), *Collinsella aerofaciens* (species), *Phascolarctobacterium faecium* (species), *Bacteroides fragilis* (species), *Parabacte-* roides distasonis (species), *Flavonifractor plautii* (species), *Megamonas funiformis* (species), *Roseburia inulinivorans* (species), and wherein the set of microbiome functional diversity features is associated with at least one of Translation (KEGG2), Cellular Processes and Signaling (KEGG2), Metabolism (KEGG2), Biosynthesis of Other Secondary Metabolites (KEGG2), Replication and Repair (KEGG2), Cell Growth and Death (KEGG2), Carbohydrate Metabolism (KEGG2), Poorly Characterized (KEGG2), Signaling Molecules and Interaction (KEGG2), Transport and Catabolism (KEGG2), Glycan Biosynthesis and Metabolism (KEGG2), Nucleotide Metabolism (KEGG2), Energy Metabolism (KEGG2), Environmental Adaptation (KEGG2), Metabolism of Terpenoids and Polyketides (KEGG2), Lipid Metabolism (KEGG2), Metabolism of Other Amino Acids (KEGG2), Inorganic ion transport and metabolism (KEGG3), Ribosome Biogenesis (KEGG3), Aminoacyl-tRNA biosynthesis (KEGG3), Amino acid related enzymes (KEGG3), Amino acid metabolism (KEGG3), Ribosome (KEGG3), Other transporters (KEGG3), RNA polymerase (KEGG3), Biotin metabolism (KEGG3), Sphingolipid metabolism (KEGG3), Phosphatidylinositol signaling system (KEGG3), Galactose metabolism (KEGG3), Ribosome biogenesis in eukaryotes (KEGG3), Other glycan degradation (KEGG3), Other ion-coupled transporters (KEGG3), Glycosphingolipid biosynthesis—globo series (KEGG3), Amino sugar and nucleotide sugar metabolism (KEGG3), Homologous recombination (KEGG3), DNA repair and recombination proteins (KEGG3), Terpenoid backbone biosynthesis (KEGG3), Translation factors (KEGG3), Carbohydrate metabolism (KEGG3), Pentose and glucuronate interconversions (KEGG3), Lysosome (KEGG3), Peptidoglycan biosynthesis (KEGG3), Pyrimidine metabolism (KEGG3), Alzheimer's disease (KEGG3), Nitrogen metabolism (KEGG3), Translation proteins (KEGG3), Glycosaminoglycan degradation (KEGG3), Others (KEGG3), Protein export (KEGG3), Function unknown (KEGG3), Starch and sucrose metabolism (KEGG3), Cell cycle—*Caulobacter* (KEGG3), Bacterial toxins (KEGG3), Tuberculosis (KEGG3), Cyanoamino acid metabolism (KEGG3), Glyoxylate and dicarboxylate metabolism (KEGG3), D-Alanine metabolism (KEGG3), Photosynthesis proteins (KEGG3), Mismatch repair (KEGG3), Photosynthesis (KEGG3), Nicotinate and nicotinamide metabolism (KEGG3), Base excision repair (KEGG3), Biosynthesis of siderophore group nonribosomal peptides (KEGG3), Nucleotide excision repair (KEGG3), Glycosphingolipid biosynthesis—ganglio series (KEGG3), Pores ion channels (KEGG3), Phenylpropanoid biosynthesis (KEGG3), Chromosome (KEGG3), Penicillin and cephalosporin biosynthesis (KEGG3), Bisphenol degradation (KEGG3), Pantothenate and CoA biosynthesis (KEGG3), DNA replication proteins (KEGG3), Prenyltransferases (KEGG3), Vitamin metabolism (KEGG3), Plant-pathogen interaction (KEGG3), DNA replication (KEGG3), Lipopolysaccharide biosynthesis proteins (KEGG3), Propanoate metabolism (KEGG3), Membrane and intracellular structural molecules (KEGG3), Insulin signaling pathway (KEGG3), Arginine and proline metabolism (KEGG3), Fructose and mannose metabolism (KEGG3), Polyketide sugar unit biosynthesis (KEGG3), Benzoate degradation (KEGG3), Cell motility and secretion (KEGG3), One carbon pool by folate (KEGG3), Cell division (KEGG3), Oxidative phosphorylation (KEGG3), Streptomycin biosynthesis (KEGG3), Sulfur metabolism (KEGG3), Butanoate metabolism (KEGG3), Biosynthesis and biodegradation of secondary metabolites (KEGG3), Phenylalanine metabolism (KEGG3), Primary immunodeficiency (KEGG3), Biosynthesis of vancomycin group antibiotics (KEGG3), Carbon fixation in photosynthetic organisms (KEGG3), Glycosyltransferases (KEGG3), Drug metabolism—other enzymes (KEGG3), Tryptophan metabolism (KEGG3).

15. The method of claim 1, wherein the human behavior condition comprises a menopause condition, wherein the set of microbiome composition diversity features is associated with at least one of Lactobacillaceae (Family), Clostridia (Class), Clostridiales (Order), Actinobacteria (phylum), Bacteroidetes (phylum), Firmicutes (phylum), Fusobacteria (phylum), Proteobacteria (phylum), Actinobacteria (class), Bacteroidia (class), Flavobacteriia (class), Fusobacteriia (class), Gammaproteobacteria (class), Negativicutes (class), Actinomycetales (order), Bacteroidales (order), Flavobacteriales (order), Fusobacteriales (order), Pasteurellales (order), Selenomonadales (order), Bacteroidaceae (family), Clostridiales Family XI. Incertae Sedis (family), Corynebacteriaceae (family), Flavobacteriaceae (family), Lachnospiraceae (family), Pasteurellaceae (family), Propionibacteriaceae (family), Staphylococcaceae (family), Streptococcaceae (family), *Asaccharospora* (genus), *Bacteroides* (genus), *Blautia* (genus), *Capnocytophaga* (genus), *Corynebacterium* (genus), *Faecalibacterium* (genus), *Haemophilus* (genus), *Propionibacterium* (genus), *Roseburia* (genus), *Staphylococcus* (genus), *Streptococcus* (genus), *Anaerococcus* sp. 8404299 (species), *Asaccharospora irregularis* (species), *Bacteroides* vulgatus (species), *Blautia wexlerae* (species), *Faecalibacterium prausnitzii* (species), *Haemophilus influenzae* (species), *Parabacteroides distasonis* (species), *Veillonella rogosae* (species), *Veillonella* sp. CM60 (species).

16. A method for characterizing a disease-related condition associated with microorganisms, the method comprising:
    collecting a sample from a user, wherein the sample comprises microorganism nucleic acids associated with the disease-related condition;
    determining a microorganism sequence dataset based on the microorganism nucleic acids of the sample;
    determining at least one of a set of microbiome composition diversity features and a set of microbiome functional diversity features for the user, based on the microorganism sequence dataset;
    generating a disease-related characterization for the user based on a disease characterization model and the at least one of the set of microbiome composition diversity features and the set of microbiome functional diversity features; and
    providing a therapy to the user for the disease-related condition based on the disease-related characterization.

17. The method of claim 16, wherein providing the therapy to the user comprises promoting a diagnostic procedure for the disease-related condition based on the disease-related characterization, wherein the diagnostic procedure comprises at least one of: a medical history analysis, a blood test, an imaging exam, a cell culture test, and an antibody test.

18. The method of claim 16, wherein generating the disease-related characterization based on the disease characterization model comprises applying at least one of a machine learning approach, a parameter optimization approach, a statistical test, and a dimension reduction approach, wherein the at least one of the set of microbiome composition diversity features and the set of microbiome functional diversity features is associated with microorganisms collected at least at one of a gut site, a skin site, a nose site, a mouth site, and a genitals site.

19. The method of claim 16, wherein the disease-related condition comprises at least one of a cancer condition, an anemia condition, and a Lyme disease condition, wherein providing the therapy comprises promoting at least one of a probiotic therapy and a prebiotic therapy to the user based on the disease-related characterization, and wherein the at least one of the probiotic therapy and the prebiotic therapy is associated with at least one of: *Blautia luti, Collinsella aerofaciens, Flavonifractor plautii, Subdoligranulum variabile, Faecalibacterium prausnitzii, Dorea formicigenerans, Roseburia inulinivorans, Blautia* sp. YHC-4, *Parasutterella excrementihominis, Sutterella wadsworthensis, Bacteroides caccae, Parabacteroides merdae.*

20. The method of claim 16, wherein the disease-related condition comprises a cancer condition, wherein the set of microbiome composition diversity features is associated with at least one of *Blautia luti* (Species), *Collinsella aerofaciens* (Species), *Flavonifractor plautii* (Species), *Subdoligranulum variabile* (Species), *Faecalibacterium prausnitzii* (Species), *Dorea formicigenerans* (Species), *Roseburia inulinivorans* (Species), *Blautia* sp. YHC-4 (Species), *Parasutterella excrementihominis* (Species), *Sutterella wadsworthensis* (Species), *Bacteroides caccae* (Species), *Moryella* (Genus), *Collinsella* (Genus), *Subdoligranulum* (Genus), *Dorea* (Genus), *Terrisporobacter* (Genus), *Parabacteroides* (Genus), *Bifidobacterium* (Genus), *Faecalibacterium* (Genus), *Bacteroides* (Genus), *Lachnospira* (Genus), *Pseudobutyrivibrio* (Genus), *Erysipelatoclostridium* (Genus), Coriobacteriaceae (Family), Porphyromonadaceae (Family), Bifidobacteriaceae (Family), Ruminococcaceae (Family), Bacteroidaceae (Family), Oscillospiraceae (Family), Sutterellaceae (Family), Flavobacteriaceae (Family), Coriobacteriales (Order), Bacteroidales (Order), Clostridiales (Order), Bifidobacteriales (Order), Burkholderiales (Order), Flavobacteriales (Order), Actinobacteria (Class), Bacteroidia (Class), Clostridia (Class), Betaproteobacteria (Class), Flavobacteriia (Class), Actinobacteria (phylum), Firmicutes (phylum), Alphaproteobacteria (class), Bacilli (class), Actinomycetales (order), Bacillales (order), Rhodospirillales (order), Acidaminococcaceae (family), Corynebacteriaceae (family), Staphylococcaceae (family), *Acidaminococcus* (genus), *Bilophila* (genus), *Corynebacterium* (genus), *Flavonifractor* (genus), *Intestinibacter* (genus), *Intestinimonas* (genus), *Lactonifactor* (genus), *Staphylococcus* (genus), *Streptococcus* (genus), *Bacteroides* sp. AR20 (species), *Bilophila* sp. 4_1_30 (species), and wherein the set of microbiome functional diversity features is associated with at least one of Metabolism (KEGG2), Transport and Catabolism (KEGG2), Glycan Biosynthesis and Metabolism (KEGG2), Lipid Metabolism (KEGG2), Carbohydrate Metabolism (KEGG2), Biosynthesis of Other Secondary Metabolites (KEGG2), Poorly Characterized (KEGG2), Cellular Processes and Signaling (KEGG2), Environmental Adaptation (KEGG2), Translation (KEGG2), Replication and Repair (KEGG2), Signaling Molecules and Interaction (KEGG2), Phosphatidylinositol signaling system (KEGG3), Ion channels (KEGG3), Lipoic acid metabolism (KEGG3), Phosphonate and phosphinate metabolism (KEGG3), Glycosaminoglycan degradation (KEGG3), Inorganic ion transport and metabolism (KEGG3), Lysosome (KEGG3), Lipopolysaccharide biosynthesis proteins (KEGG3), Membrane and intracellular structural molecules (KEGG3), Ribosome Biogenesis (KEGG3), Plant-pathogen interaction (KEGG3), Huntington's disease (KEGG3), Penicillin and cephalosporin biosynthesis (KEGG3), Ascorbate and aldarate metabolism (KEGG3), Cell motility and secretion (KEGG3), Pores ion channels (KEGG3), Function unknown (KEGG3), Sphingolipid metabolism (KEGG3), Pentose and glucuronate interconversions (KEGG3), Others (KEGG3), Other glycan degradation (KEGG3), Glycosphingolipid biosynthesis—globo series (KEGG3), Glycosphingolipid biosynthesis—ganglio series (KEGG3), Chromosome (KEGG3), Inositol phosphate metabolism (KEGG3), Biotin metabolism (KEGG3), Sulfur metabolism (KEGG3), Amino acid metabolism (KEGG3), Biosynthesis and biodegradation of secondary metabolites (KEGG3), Phenylalanine metabolism (KEGG3), Carbohydrate metabolism (KEGG3), D-Alanine metabolism (KEGG3), Glyoxylate and dicarboxylate metabolism (KEGG3), Streptomycin biosynthesis (KEGG3), RNA polymerase (KEGG3), Amino acid related enzymes (KEGG3), Glycosyltransferases (KEGG3), MAPK signaling pathway—yeast (KEGG3), Peptidoglycan biosynthesis (KEGG3), Terpenoid backbone biosynthesis (KEGG3), Amino sugar and nucleotide sugar metabolism (KEGG3), Other transporters (KEGG3), Geraniol degradation (KEGG3), Vitamin metabolism (KEGG3), Taurine and hypotaurine metabolism (KEGG3), Pyrimidine metabolism (KEGG3), Thiamine metabolism (KEGG3), Ribosome (KEGG3), Homologous recombination (KEGG3) and Translation proteins (KEGG3).

21. The method of claim 16, wherein the disease-related condition comprises an anemia condition, wherein the set of microbiome composition diversity features is associated with at least one of *Flavonifractor plautii* (Species), *Blautia luti* (Species), *Collinsella aerofaciens* (Species), *Subdoligranulum variabile* (Species), *Dorea formicigenerans* (Species), *Blautia* sp. YHC-4 (Species), *Faecalibacterium prausnitzii* (Species), *Roseburia inulinivorans* (Species), *Subdoligranulum* (Genus), *Terrisporobacter* (Genus), *Dorea* (Genus), *Collinsella* (Genus), *Sarcina* (Genus), *Clostridium* (Genus), *Marvinbryantia* (Genus), *Moryella* (Genus), *Lactobacillus* (Genus), *Bacteroides* (Genus), *Eggerthella* (Genus), *Kluyvera* (Genus), *Faecalibacterium* (Genus), *Thalassospira* (Genus), Lactobacillaceae (Family), Coriobacteriaceae (Family), Clostridiaceae (Family), Ruminococcaceae (Family), Bacteroidaceae (Family), Flavobacteriaceae (Family), Oscillospiraceae (Family), Rhodospirillaceae (Family), Enterobacteriaceae (Family), Porphyromonadaceae (Family), Coriobacteriales (Order), Bacteroidales (Order), Flavobacteriales (Order), Clostridiales (Order), Rhodospirillales (Order), Enterobacteriales (Order), Selenomonadales (Order), Actinobacteria (Class), Bacteroidia (Class), Clostridia (Class), Flavobacteriia (Class), Alphaproteobacteria (Class), Negativicutes (Class), Actinobacteria (Phylum), Bacteroidetes (Phylum), Firmicutes (Phylum), Acidaminococcaceae (family), *Odoribacter* (genus), *Phascolarctobacterium* (genus), *Flavonifractor plautii* (species), and wherein the set of microbiome functional diversity features is associated with at least one of Metabolism (KEGG2), Translation (KEGG2), Carbohydrate Metabolism (KEGG2), Replication and Repair (KEGG2), Cellular Processes and Signaling (KEGG2), Signaling Molecules and Interaction (KEGG2), Nucleotide Metabolism (KEGG2), Poorly Characterized (KEGG2), Glycan Biosynthesis and Metabolism (KEGG2), Metabolism of Other Amino Acids (KEGG2), Environmental Adaptation (KEGG2), Cell Growth and Death (KEGG2), Biosynthesis of Other Secondary Metabolites (KEGG2), Transport and Catabolism (KEGG2), Lipid Metabolism (KEGG2), Signal Transduction (KEGG2), Ribosome Biogenesis (KEGG3), Amino acid metabolism (KEGG3), Ion channels (KEGG3), Pentose and glucuronate interconversions (KEGG3), Ribosome biogenesis in eukaryotes (KEGG3), Others (KEGG3), Inorganic ion transport and metabolism (KEGG3), Amino acid related enzymes (KEGG3), Ascorbate and aldarate metabolism (KEGG3), Peptidoglycan biosynthesis (KEGG3), Aminoacyl-tRNA biosynthesis (KEGG3), Translation proteins (KEGG3), Ribosome (KEGG3), Chromosome (KEGG3), MAPK signaling pathway—yeast (KEGG3), Terpenoid backbone biosynthesis (KEGG3), RNA polymerase (KEGG3), Nicotinate and nicotinamide metabolism (KEGG3), Penicillin and cephalosporin biosynthesis (KEGG3), Homologous recombination (KEGG3), Lipoic acid metabolism (KEGG3), DNA repair and recombination proteins (KEGG3), Biosynthesis and biodegradation of secondary metabolites (KEGG3), Translation factors (KEGG3), Glyoxylate and dicarboxylate metabolism (KEGG3), Phosphatidylinositol signaling system (KEGG3), Pyrimidine metabolism (KEGG3), Other ion-coupled transporters (KEGG3), Taurine and hypotaurine metabolism (KEGG3), Cell motility and secretion (KEGG3), Carbohydrate metabolism (KEGG3), Function unknown (KEGG3), D-Alanine metabolism (KEGG3), Fructose and mannose metabolism (KEGG3), Plant-pathogen interaction (KEGG3), Vitamin metabolism (KEGG3), Phosphonate and phosphinate metabolism (KEGG3), Lipopolysaccharide biosynthesis proteins (KEGG3), Amino sugar and nucleotide sugar metabolism (KEGG3), Galactose metabolism (KEGG3), Other transporters (KEGG3), Membrane and intracellular structural molecules (KEGG3), Nucleotide excision repair (KEGG3), Pores ion channels (KEGG3), Sphingolipid metabolism (KEGG3), Protein export (KEGG3), Cell cycle—*Caulobacter* (KEGG3), Bisphenol degradation (KEGG3), Cysteine and methionine metabolism (KEGG3), Mismatch repair (KEGG3), Huntington's disease (KEGG3), Bacterial toxins (KEGG3), Nitrogen metabolism (KEGG3), Other glycan degradation (KEGG3), Lysosome (KEGG3), Phenylalanine metabolism (KEGG3), Cyanoamino acid metabolism (KEGG3), Glycosaminoglycan degradation (KEGG3), Nucleotide metabolism (KEGG3), Glycosphingolipid biosynthesis—globo series (KEGG3) and Pantothenate and CoA biosynthesis (KE-G3).

22. The method of claim 16, wherein the disease-related condition comprises a Lyme disease condition, wherein the set of microbiome composition diversity features is associated with at least one of *Blautia luti* (Species), *Parabacteroides merdae* (Species), *Dorea* (Genus), *Subdoligranulum* (Genus), *Collinsella* (Genus), *Parabacteroides* (Genus), *Sarcina* (Genus), *Roseburia* (Genus), *Oscillospira* (Genus), *Bacteroides* (Genus), *Clostridium* (Genus), Oscillospiraceae (Family), Coriobacteriaceae (Family), Bacteroidaceae (Family), Ruminococcaceae (Family), Lactobacillaceae (Family), Fibrobacteraceae (Family), Clostridiaceae (Family), Porphyromonadaceae (Family), Coriobacteriales (Order), Bacteroidales (Order), Clostridiales (Order), Fibrobacterales (Order), Actinobacteria (Class), Bacteroidia (Class), Clostridia (Class), Fibrobacteria (Class), Actinobacteria (Phylum), Bacteroidetes (Phylum), Firmicutes (Phylum), Fibrobacteres (Phylum), Euryarchaeota (phylum), Fusobacteria (phylum), Tenericutes (phylum), Verrucomicrobia (phylum), Deltaproteobacteria (class), Flavobacteriia (class), Fusobacteriia (class), Methanobacteria (class), Mollicutes (class), Negativicutes (class), Verrucomicrobiae (class), Anaeroplasmatales (order), Bacillales (order), Bifidobacteriales (order), Burkholderiales (order), Desulfovibrionales (order), Enterobacteriales (order), Flavobacteriales (order), Fusobacteriales (order), Methanobacteriales (order), Rhizobiales (order), Rhodospirillales (order), Selenomonadales (order), Thermoanaerobacterales (order), Verrucomicrobiales (order), Acidaminococcaceae (family), Anaeroplasmataceae (family), Bacillaceae (family), Bifidobacteriaceae (family), Carnobacteriaceae (family), Catabacteriaceae (family), Clostridiales Family XIII. Incertae Sedis (family), Desulfovibrionaceae (family), Enterobacteriaceae (family), Enterococcaceae (family), Eubacteriaceae (family), Flavobacteriaceae (family), Fusobacteriaceae (family), Lachnospiraceae (family), Leptotrichiaceae (family), Leuconostocaceae (family), Methanobacteriaceae (family), Micrococcaceae (family), Rhodospirillaceae (family), Rikenellaceae (family), Streptococcaceae (family), Sutterellaceae (family), Thermoanaerobacteraceae (family), Veillonellaceae (family), Verrucomicrobiaceae (family), *Actinobacillus* (genus), *Actinomyces* (genus), *Adlercreutzia* (genus), *Akkermansia* (genus), *Alistipes* (genus), *Anaerofilum* (genus), *Anaerofustis* (genus), *Anaerotruncus* (genus), *Bacillus* (genus), *Barnesiella* (genus), *Bifidobacterium* (genus), *Bilophila* (genus), *Butyricicoccus* (genus), *Butyricimonas* (genus), *Candidatus Soleaferrea* (genus), *Catabacter* (genus), *Citrobacter* (genus), *Coprobacillus* (genus), *Coprobacter* (genus), *Dialister* (genus), *Dielma* (genus), *Eggerthella* (genus), *Eisenbergiella* (genus), *Enterococcus* (genus), *Enterorhabdus* (genus), *Eubacterium* (genus), *Faecalibacterium* (genus), *Flavonifractor* (genus), *Fusicatenibacter* (genus), *Fusobacterium* (genus), *Gelria* (genus), *Gordonibacter* (genus), *Granulicatella* (genus), *Haemophilus* (genus), *Helcococcus* (genus), *Hespellia* (genus), *Holdemania* (genus), *Howardella* (genus), *Intestinimonas* (genus), *Kluyvera* (genus), *Lachnospira* (genus), *Lactobacillus* (genus), *Lactonifactor* (genus), *Marvinbryantia* (genus), *Megasphaera* (genus), *Methanobrevibacter* (genus), *Moryella* (genus), *Odoribacter* (genus), *Oscillibacter* (genus), *Parasutterella* (genus), *Parvimonas* (genus), *Phascolarctobacterium* (genus), *Pseudoflavonifractor* (genus), *Pseudomonas* (genus), *Robinsoniella* (genus), *Romboutsia* (genus), *Shuttleworthia* (genus), *Sutterella* (genus), *Syntrophococcus* (genus), *Terrisporobacter* (genus), *Thalassospira* (genus), *Actinobacillus porcinus* (species), *Actinomyces* sp. ICM54 (species), *Adlercreutzia equolifaciens* (species), *Akkermansia muciniphila* (species), *Alistipes finegoldii* (species), *Alistipes putredinis* (species), *Alistipes* sp. EBA6-25cl2 (species), *Alistipes* sp. NML05A004 (species), *Alistipes* sp. RMA9912 (species), *Anaerococcus vaginalis* (species), *Anaerofustis stercorihominis* (species), *Anaerosporobacter mobilis* (species), *Anaerostipes* sp. 3_2_56FAA (species), *Anaerostipes* sp. 494a (species), *Anaerostipes* sp. 5_1_63FAA (species), *Anaerotruncus colihominis* (species), *Bacteroides acidifaciens* (species), *Bacteroides caccae* (species), *Bacteroides finegoldii* (species), *Bacteroides fragilis* (species), *Bacteroides massiliensis* (species), *Bacteroides ovatus* (species), *Bacteroides* sp. AR20 (species), *Bacteroides* sp. AR29 (species), *Bacteroides* sp. D22 (species), *Bacteroides* sp. EBA5-17 (species), *Bacteroides* sp. SLC1-38 (species), *Bacteroides* sp. XB12B (species), *Bacteroides stercoris* (species), *Bacteroides thetaiotaomicron* (species), *Bacteroides uniformis* (species), *Bacteroides vulgatus* (species), *Barnesiella intestinihominis* (species), *Bifidobacterium kashiwanohense* (species), *Bifidobacterium longum* (species), *Bifidobacterium stercoris* (species), *Bilophila* sp. 4_1_30 (species), *Bilophila wadsworthia* (species), *Blautia faecis* (species), *Blautia glucerasea* (species), *Blautia producta* (species), *Blautia* sp. Ser8 (species), *Blautia* sp. YHC-4 (species), *Blautia stercoris* (species), *Blautia wexlerae* (species), *Butyricicoccus pullicaecorum* (species), *Butyrivibrio crossotus* (species), *Collinsella aerofaciens* (species), *Coproba-* cillus sp. D6 (species), *Coprobacter fastidiosus* (species), *Corynebacterium canis* (species), *Desulfovibrio piger* (species), *Dielma fastidiosa* (species), *Dorea formicigenerans* (species), *Dorea longicatena* (species), *Eggerthella lenta* (species), *Eggerthella sinensis* (species), *Eggerthella* sp. HGA1 (species), *Eisenbergiella tayi* (species), *Enterococcus* sp. C6I11 (species), *Enterococcus* sp. SI-4 (species), *Erysipelatoclostridium ramosum* (species), *Eubacterium callanderi* (species), *Faecalibacterium prausnitzii* (species), *Faecalibacterium* sp. canine oral taxon 147 (species), *Fastidiosipila sanguinis* (species), *Flavonifractor plautii* (species), *Fusicatenibacter saccharivorans* (species), *Fusobacterium periodonticum* (species), *Fusobacterium* sp. CM21 (species), *Fusobacterium* sp. CM22 (species), *Gordonibacter pamelaeae* (species), *Granulicatella adiacens* (species), *Holdemania filiformis* (species), *Howardella ureilytica* (species), *Klebsiella* sp. SOR89 (species), *Kluyvera georgiana* (species), *Lachnospira pectinoschiza* (species), *Lactobacillus fornicalis* (species), *Lactobacillus salivarius* (species), *Lactobacillus* sp. BL302 (species), *Lactobacillus* sp. TAB-30 (species), *Lactonifactor longoviformis* (species), *Megasphaera genomosp.* C1 (species), *Methanobrevibacter smithii* (species), *Odoribacter splanchnicus* (species), *Parabacteroides distasonis* (species), *Parasutterella excrementihominis* (species), *Parvimonas micra* (species), *Peptostreptococcus stomatis* (species), *Phascolarctobacterium faecium* (species), *Phascolarctobacterium succinatutens* (species), *Porphyromonas* sp. 2026 (species), *Prevotella timonensis* (species), *Propionibacterium propionicum* (species), *Pseudoflavonifractor capillosus* (species), *Robinsoniella peoriensis* (species), *Roseburia faecis* (species), *Roseburia hominis* (species), *Roseburia inulinivorans* (species), *Roseburia* sp. 11SE39 (species), *Roseburia* sp. 499 (species), *Streptococcus* sp. 11aTha1 (species), *Streptococcus* sp. 2011_Oral_MS_A3 (species), *Subdoligranulum variabile* (species), *Sutterella wadsworthensis* (species), and wherein the set of microbiome functional diversity features is associated with at least one of Metabolism (KEGG2), Carbohydrate Metabolism (KEGG2), Translation (KEGG2), Transport and Catabolism (KEGG2), Environmental Adaptation (KEGG2), Glycan Biosynthesis and Metabolism (KEGG2), Signaling Molecules and Interaction (KEGG2), Genetic Information Processing (KEGG2), Lipid Metabolism (KEGG2), Cellular Processes and Signaling (KEGG2), Neurodegenerative Diseases (KEGG2), Biosynthesis of Other Secondary Metabolites (KEGG2), Metabolism of Cofactors and Vitamins (KEGG2), Metabolism of Other Amino Acids (KEGG2), Enzyme Families (KEGG2), Nucleotide Metabolism (KEGG2), Replication and Repair (KEGG2), Pentose and glucuronate interconversions (KEGG3), Ascorbate and aldarate metabolism (KEGG3), MAPK signaling pathway—yeast (KEGG3), Ribosome Biogenesis (KEGG3), Fructose and mannose metabolism (KEGG3), Lipoic acid metabolism (KEGG3), Bisphenol degradation (KEGG3), Huntington's disease (KEGG3), Phosphonate and phosphinate metabolism (KEGG3), Translation proteins (KEGG3), Other glycan degradation (KEGG3), Sphingolipid metabolism (KEGG3), Inorganic ion transport and metabolism (KEGG3), Plant-pathogen interaction (KEGG3), Lysosome (KEGG3), Others (KEGG3), Ribosome biogenesis in eukaryotes (KEGG3), Carbohydrate metabolism (KEGG3), Glycosphingolipid biosynthesis—globo series (KEGG3), Amino acid metabolism (KEGG3), Amino acid related enzymes (KEGG3), Glycosaminoglycan degradation (KEGG3), Peptidoglycan biosynthesis (KEGG3), Thiamine metabolism (KEGG3), Galactose metabolism (KEGG3), RNA polymerase (KEGG3), Phosphatidylinositol signaling system (KEGG3), Ion channels (KEGG3), Inositol phosphate metabolism (KEGG3), Aminoacyl-tRNA biosynthesis (KEGG3), Cyanoamino acid metabolism (KEGG3), Terpenoid backbone biosynthesis (KEGG3), Phenylpropanoid biosynthesis (KEGG3), Membrane and intracellular structural molecules (KEGG3), Lipopolysaccharide biosynthesis proteins (KEGG3), Taurine and hypotaurine metabolism (KEGG3), Amino sugar and nucleotide sugar metabolism (KEGG3), D-Alanine metabolism (KEGG3), Penicillin and cephalosporin biosynthesis (KEGG3), Cell motility and secretion (KEGG3), Glyoxylate and dicarboxylate metabolism (KEGG3), Other transporters (KEGG3), Chromosome (KEGG3), Other ion-coupled transporters (KEGG3), Pores ion channels (KEGG3), Pentose phosphate pathway (KEGG3), Toluene degradation (KEGG3), Signal transduction mechanisms (KEGG3), Biosynthesis and biodegradation of secondary metabolites (KEGG3), Cysteine and methionine metabolism (KEGG3), Photosynthesis proteins (KEGG3), Glycosphingolipid biosynthesis—ganglio series (KEGG3), Photosynthesis (KEGG3), Replication, recombination and repair proteins (KEGG3), Pantothenate and CoA biosynthesis (KEGG3), Ubiquinone and other terpenoid-quinone biosynthesis (KEGG3), Ribosome (KEGG3), Geraniol degradation (KEGG3), Energy metabolism (KEGG3), Phenylalanine metabolism (KEGG3), Bacterial chemotaxis (KEGG3), Bacterial toxins (KEGG3), Limonene and pinene degradation (KEGG3), DNA repair and recombination proteins (KEGG3), Peroxisome (KEGG3), Nucleotide excision repair (KEGG3), Citrate cycle (TCA cycle) (KEGG3), Type II diabetes mellitus (KEGG3).

* * * * *